United States Patent
Wang et al.

(10) Patent No.: US 8,221,322 B2
(45) Date of Patent: Jul. 17, 2012

(54) SYSTEMS AND METHODS TO IMPROVE CLARITY IN ULTRASOUND IMAGES

(75) Inventors: Yanwei Wang, Woodinville, WA (US); Fuxing Yang, Woodinville, WA (US); Susannah Helen Bloch, Seattle, WA (US); Stephen Dudycha, Bothell, WA (US); Gerald McMorrow, Redmond, WA (US)

(73) Assignee: Verathon Inc., Bothell, WA (US)

( * ) Notice: Subject to any disclaimer, the term of this patent is extended or adjusted under 35 U.S.C. 154(b) by 722 days.

(21) Appl. No.: 11/680,380

(22) Filed: Feb. 28, 2007

(65) Prior Publication Data

US 2007/0232908 A1    Oct. 4, 2007

Related U.S. Application Data

(63) Continuation-in-part of application No. 11/213,284, filed on Aug. 26, 2005, and a continuation-in-part of application No. 11/119,355, filed on Apr. 29, 2005, and a continuation-in-part of application No. 10/701,955, filed on Nov. 5, 2003, which is a continuation-in-part of application No. 10/443,126, filed on May 20, 2003, application No. 11/680,380, which is a continuation-in-part of application No. 11/061,867, filed on Feb. 17, 2005, and a continuation-in-part of application No. 11/222,360, filed on Sep. 8, 2005, and a continuation-in-part of application No. 11/061,867, filed on Feb. 17, 2005, and a continuation-in-part of application No. 10/704,966, filed on Nov. 10, 2004, and a continuation-in-part of application No.

(Continued)

(51) Int. Cl.
*A61B 8/00* (2006.01)

(52) U.S. Cl. ........ 600/437; 600/439; 600/447; 600/441; 600/443

(58) Field of Classification Search .......... 600/437–439, 600/441–447; 73/602, 607; 378/62
See application file for complete search history.

(56) References Cited

U.S. PATENT DOCUMENTS 3,613,069 A    10/1971    Cary, Jr. et al. ............... 340/3 R
(Continued)

FOREIGN PATENT DOCUMENTS

EP    0 271 214    6/1988
(Continued)

OTHER PUBLICATIONS

Baker, A., et al.: "Distortion and High-Frequency Generation Due to Nonlinear Propagation of Short Ultrasonic Pulses from a Plane Circular Piston", Journal of Acoustical Society of America, vol. 92, No. 3, pp. 1699-1705, Sep. 1992.

(Continued)

*Primary Examiner* — Brian Casler
*Assistant Examiner* — Joel Lamprecht
(74) *Attorney, Agent, or Firm* — Scott Born; Foster Pepper PLLC

(57) ABSTRACT

Systems, methods, and devices for image clarity of ultrasound-based images are described wherein motion sections are compensated with the still sections of the region of interest. Velocity map analysis of regions-of-interest is determined to compensate for instrument motion from motions attributable to structures within the region of interest. Methods include image processing algorithms applied to collected echogenic data sets and the dispensers that use apply air-expunged sonic coupling mediums.

2 Claims, 44 Drawing Sheets

Related U.S. Application Data

10/607,919, filed on Jun. 27, 2005, and a continuation-in-part of application No. PCT/US03/24368, filed on Aug. 1, 2003, and a continuation-in-part of application No. PCT/US03/14785, filed on May 9, 2003, which is a continuation of application No. 10/165,556, filed on Jun. 7, 2002, application No. 11/680,380, which is a continuation-in-part of application No. 10/888,735, filed on Jul. 9, 2004, and a continuation-in-part of application No. 10/633,186, filed on Jul. 31, 2003.

(60) Provisional application No. 60/882,888, filed on Dec. 29, 2006, provisional application No. 60/828,614, filed on Oct. 6, 2006, provisional application No. 60/760,677, filed on Jan. 20, 2006, provisional application No. 60/778,634, filed on Mar. 1, 2006, provisional application No. 60/566,127, filed on Apr. 30, 2004, provisional application No. 60/545,576, filed on Feb. 17, 2004, provisional application No. 60/566,818, filed on Apr. 30, 2004, provisional application No. 60/423,881, filed on Nov. 5, 2002, provisional application No. 60/400,624, filed on Aug. 2, 2002.

(56) References Cited

U.S. PATENT DOCUMENTS

| | | | |
|---|---|---|---|
| 4,431,007 A | 2/1984 | Amazeen et al. | 128/660 |
| 4,556,066 A | 12/1985 | Semrow | 128/660 |
| 4,757,821 A | 7/1988 | Snyder | |
| 4,771,205 A | 9/1988 | Mequio | 310/334 |
| 4,821,210 A | 4/1989 | Rumbaugh | 364/518 |
| 4,844,080 A | 7/1989 | Frass et al. | |
| 4,926,871 A | 5/1990 | Ganguly et al. | 128/660.07 |
| 5,058,591 A | 10/1991 | Companion et al. | 128/661.03 |
| 5,060,515 A | 10/1991 | Kanda et al. | 73/602 |
| 5,078,149 A | 1/1992 | Katsumata et al. | 128/662.03 |
| 5,125,410 A | 6/1992 | Misono et al. | 128/662.06 |
| 5,148,809 A | 9/1992 | Biegeleisen-Knight et al. | 128/660.07 |
| 5,151,856 A | 9/1992 | Halmann et al. | 364/413.03 |
| 5,159,931 A | 11/1992 | Pini | 128/660.07 |
| 5,197,019 A | 3/1993 | Delon-Martin et al. | 364/563 |
| 5,235,985 A | 8/1993 | McMorrow et al. | 128/660.07 |
| 5,265,614 A | 11/1993 | Hayakawa et al. | 128/602.03 |
| 5,299,577 A | 4/1994 | Brown et al. | |
| 5,381,794 A | 1/1995 | Tei et al. | 128/662.03 |
| 5,432,310 A | 7/1995 | Stoeger | 200/82 R |
| 5,435,310 A | 7/1995 | Sheehan et al. | 128/653.1 |
| 5,465,721 A | 11/1995 | Kishimoto et al. | 128/660.07 |
| 5,473,555 A | 12/1995 | Potter | 364/724.1 |
| 5,487,388 A | 1/1996 | Rello et al. | 128/660.09 |
| 5,503,152 A | 4/1996 | Oakley et al. | 128/661.01 |
| 5,503,153 A | 4/1996 | Liu et al. | |
| 5,526,816 A | 6/1996 | Arditi | 128/662.02 |
| 5,553,618 A | 9/1996 | Suzuki et al. | |
| 5,575,286 A | 11/1996 | Weng et al. | 128/653.1 |
| 5,575,291 A | 11/1996 | Hayakawa et al. | 128/662.03 |
| 5,577,506 A | 11/1996 | Dias | |
| 5,588,435 A | 12/1996 | Weng et al. | 128/660.07 |
| 5,601,084 A | 2/1997 | Sheehan et al. | 128/661.04 |
| 5,605,155 A | 2/1997 | Chalana et al. | 128/660.07 |
| 5,615,680 A | 4/1997 | Sano | |
| 5,644,513 A | 7/1997 | Rudin et al. | 364/572 |
| 5,645,077 A | 7/1997 | Foxlin | 128/774 |
| 5,697,525 A | 12/1997 | O'Reilly et al. | |
| 5,698,549 A | 12/1997 | Steers et al. | 514/211 |
| 5,724,101 A | 3/1998 | Haskin | 348/441 |
| 5,735,282 A | 4/1998 | Hossack | 128/662.03 |
| 5,738,097 A | 4/1998 | Beach et al. | 128/661.09 |
| 5,776,063 A | 7/1998 | Dittrich et al. | 600/408 |
| 5,782,767 A | 7/1998 | Pretlow, III | 600/443 |
| 5,806,521 A | 9/1998 | Morimoto et al. | 128/661.01 |
| 5,841,889 A | 11/1998 | Seyed-Bolorforosh | 382/128 |
| 5,846,202 A | 12/1998 | Ramamurthy et al. | 600/450 |
| 5,851,186 A | 12/1998 | Wood et al. | 600/437 |
| 5,873,829 A | 2/1999 | Kamiyama et al. | 600/443 |
| 5,892,843 A | 4/1999 | Zhou et al. | 382/176 |
| 5,898,793 A | 4/1999 | Karron et al. | 382/131 |
| 5,903,664 A | 5/1999 | Hartley et al. | 382/154 |
| 5,908,390 A | 6/1999 | Matsushima | 600/447 |
| 5,913,823 A | 6/1999 | Hedberg et al. | 600/443 |
| 5,928,151 A | 7/1999 | Hossack et al. | 600/443 |
| 5,945,770 A | 8/1999 | Hanafy | 310/322 |
| 5,964,710 A | 10/1999 | Ganguly et al. | 600/449 |
| 5,971,923 A | 10/1999 | Finger | 600/437 |
| 5,972,023 A | 10/1999 | Tanner et al. | 606/219 |
| 5,980,459 A | 11/1999 | Chiao et al. | 600/447 |
| 5,993,390 A | 11/1999 | Savord et al. | 600/437 |
| 6,008,813 A | 12/1999 | Lauer et al. | 345/424 |
| 6,030,344 A | 2/2000 | Guracar et al. | |
| 6,042,545 A | 3/2000 | Hossack et al. | 600/443 |
| 6,048,312 A | 4/2000 | Ishrak et al. | |
| 6,063,033 A | 5/2000 | Haider et al. | 600/447 |
| 6,064,906 A | 5/2000 | Langberg et al. | 600/518 |
| 6,071,242 A | 6/2000 | Lin | 600/456 |
| 6,102,858 A | 8/2000 | Hatfield et al. | 600/443 |
| 6,106,465 A | 8/2000 | Napolitano et al. | 600/443 |
| 6,110,111 A | 8/2000 | Barnard | 600/438 |
| 6,117,080 A | 9/2000 | Schwartz | 600/443 |
| 6,122,538 A | 9/2000 | Sliwa, Jr. et al. | 600/407 |
| 6,123,669 A | 9/2000 | Kanda | 600/443 |
| 6,126,598 A | 10/2000 | Entrekin et al. | 600/437 |
| 6,142,942 A | 11/2000 | Clark | 600/443 |
| 6,146,330 A | 11/2000 | Tujino et al. | 600/443 |
| 6,148,095 A | 11/2000 | Prause et al. | 382/131 |
| 6,151,404 A | 11/2000 | Pieper | 382/128 |
| 6,159,150 A | 12/2000 | Yale et al. | 600/437 |
| 6,171,248 B1 | 1/2001 | Hossack et al. | 600/459 |
| 6,193,657 B1 | 2/2001 | Drapkin | 600/437 |
| 6,200,266 B1 | 3/2001 | Shokrollahi et al. | |
| 6,210,327 B1 | 4/2001 | Brackett et al. | 600/437 |
| 6,213,949 B1 | 4/2001 | Ganguly et al. | 600/449 |
| 6,213,951 B1 | 4/2001 | Krishnan et al. | 600/458 |
| 6,222,948 B1 | 4/2001 | Hossack et al. | 382/294 |
| 6,233,480 B1 | 5/2001 | Hochman et al. | 600/476 |
| 6,238,344 B1 | 5/2001 | Gamelsky et al. | 600/437 |
| 6,248,070 B1 | 6/2001 | Kanda et al. | 600/443 |
| 6,254,539 B1 | 7/2001 | Pang et al. | |
| 6,264,609 B1 | 7/2001 | Herrington et al. | 600/443 |
| 6,272,469 B1 | 8/2001 | Koritzinsky et al. | 705/2 |
| 6,277,073 B1 | 8/2001 | Bolorforosh et al. | 600/437 |
| 6,286,513 B1 | 9/2001 | Au et al. | 128/898 |
| 6,302,845 B2 | 10/2001 | Shi et al. | 600/438 |
| 6,309,353 B1 | 10/2001 | Cheng et al. | |
| 6,325,758 B1 | 12/2001 | Carol et al. | 600/439 |
| 6,338,716 B1 | 1/2002 | Hossack et al. | 600/459 |
| 6,343,936 B1 | 2/2002 | Kaufman et al. | 434/262 |
| 6,346,124 B1 | 2/2002 | Geiser et al. | 660/450 |
| 6,350,239 B1 | 2/2002 | Ohad et al. | 600/437 |
| 6,359,190 B1 | 3/2002 | Ter-Ovanesyan et al. | 604/361 |
| 6,360,027 B1 | 3/2002 | Hossack et al. | 382/294 |
| 6,375,616 B1 | 4/2002 | Soferman et al. | 600/443 |
| 6,400,848 B1 | 6/2002 | Gallagher | 382/254 |
| 6,402,762 B2 | 6/2002 | Hunter et al. | 606/130 |
| 6,406,431 B1 | 6/2002 | Barnard et al. | 600/443 |
| 6,409,665 B1 | 6/2002 | Scott et al. | |
| 6,440,071 B1 | 8/2002 | Slayton et al. | 600/437 |
| 6,440,072 B1 | 8/2002 | Schuman et al. | 600/437 |
| 6,443,894 B1 | 9/2002 | Sumanaweera et al. | 600/443 |
| 6,468,218 B1 | 10/2002 | Chen et al. | 600/443 |
| 6,485,423 B2 | 11/2002 | Angelsen et al. | 600/458 |
| 6,491,631 B2 | 12/2002 | Chiao et al. | 600/443 |
| 6,494,841 B1 | 12/2002 | Thomas et al. | 600/447 |
| 6,503,204 B1 | 1/2003 | Sumanaweera et al. | 600/459 |
| 6,511,325 B1 | 1/2003 | Lalka et al. | 434/272 |
| 6,511,426 B1 | 1/2003 | Hossack et al. | 600/437 |
| 6,511,427 B1 | 1/2003 | Sliwa, Jr. et al. | 600/438 |
| 6,515,657 B1 | 2/2003 | Zanelli | 345/419 |
| 6,524,249 B2 | 2/2003 | Moehring et al. | 600/438 |
| 6,535,759 B1 | 3/2003 | Epstein et al. | 600/547 |

| | | | |
|---|---|---|---|
| 6,540,679 B2 | 4/2003 | Slayton et al. | 600/439 |
| 6,544,179 B1 | 4/2003 | Schmiesing et al. | 600/447 |
| 6,545,678 B1 | 4/2003 | Ohazama | 345/427 |
| 6,551,246 B1 | 4/2003 | Ustuner et al. | 600/447 |
| 6,565,512 B1 | 5/2003 | Ganguly et al. | 600/449 |
| 6,569,097 B1 | 5/2003 | McMorrow et al. | 600/437 |
| 6,569,101 B2 | 5/2003 | Quistgaard et al. | 600/459 |
| 6,575,907 B1 | 6/2003 | Soferman et al. | 600/438 |
| 6,585,647 B1 | 7/2003 | Winder | 600/437 |
| 6,610,013 B1 * | 8/2003 | Fenster et al. | 600/439 |
| 6,611,141 B1 | 8/2003 | Schulz et al. | 324/226 |
| 6,622,560 B2 | 9/2003 | Song et al. | 73/606 |
| 6,628,743 B1 | 9/2003 | Drummond et al. | 378/8 |
| 6,643,533 B2 | 11/2003 | Knoplioch et al. | 600/407 |
| 6,650,927 B1 | 11/2003 | Keidar | 600/424 |
| 6,676,605 B2 | 1/2004 | Barnard et al. | 600/449 |
| 6,682,473 B1 | 1/2004 | Matsuura et al. | 600/29 |
| 6,688,177 B2 | 2/2004 | Wiesauer | 73/618 |
| 6,695,780 B1 | 2/2004 | Nahum et al. | 600/437 |
| 6,705,993 B2 | 3/2004 | Ebbini et al. | 600/443 |
| 6,716,175 B2 | 4/2004 | Geiser et al. | 600/450 |
| 6,752,762 B1 | 6/2004 | DeJong et al. | 600/458 |
| 6,755,787 B2 | 6/2004 | Hossack et al. | 600/447 |
| 6,768,811 B2 | 7/2004 | Dinstein et al. | 382/128 |
| 6,780,152 B2 | 8/2004 | Ustuner et al. | 600/443 |
| 6,788,620 B2 | 9/2004 | Shiraishi et al. | 367/152 |
| 6,801,643 B2 | 10/2004 | Pieper | 382/128 |
| 6,822,374 B1 | 11/2004 | Smith et al. | 310/334 |
| 6,825,838 B2 | 11/2004 | Smith et al. | 345/419 |
| 6,831,394 B2 | 12/2004 | Baumgartner et al. | 310/334 |
| 6,868,594 B2 | 3/2005 | Gururaja | 29/25.35 |
| 6,884,217 B2 | 4/2005 | McMorrow et al. | 600/443 |
| 6,903,813 B2 | 6/2005 | Jung et al. | 356/73 |
| 6,905,467 B2 | 6/2005 | Bradley et al. | 600/437 |
| 6,905,468 B2 | 6/2005 | McMorrow et al. | 600/443 |
| 6,911,912 B2 | 6/2005 | Roe | 340/573.1 |
| 6,936,009 B2 | 8/2005 | Venkataramani et al. | 600/459 |
| 6,939,301 B2 | 9/2005 | Abdelhak | 600/437 |
| 6,951,540 B2 | 10/2005 | Ebbini et al. | 600/437 |
| 6,954,406 B2 | 10/2005 | Jones | 367/152 |
| 6,961,405 B2 | 11/2005 | Scherch | 378/65 |
| 6,962,566 B2 | 11/2005 | Quistgaard et al. | 600/437 |
| 6,970,091 B2 | 11/2005 | Roe | 340/573.1 |
| 7,004,904 B2 | 2/2006 | Chalana et al. | 600/443 |
| 7,025,725 B2 | 4/2006 | Dione et al. | 600/443 |
| 7,041,059 B2 | 5/2006 | Chalana et al. | 600/437 |
| 7,042,386 B2 | 5/2006 | Woodford et al. | |
| 7,087,022 B2 | 8/2006 | Chalana et al. | 600/449 |
| 7,141,020 B2 | 11/2006 | Poland et al. | 600/447 |
| 7,142,905 B2 | 11/2006 | Slayton et al. | 600/427 |
| 7,177,677 B2 | 2/2007 | Kaula et al. | 600/546 |
| 7,189,205 B2 | 3/2007 | McMorrow et al. | 600/437 |
| 7,201,715 B2 * | 4/2007 | Burdette et al. | 600/3 |
| 7,215,277 B2 | 5/2007 | Woodford et al. | |
| 7,255,678 B2 | 8/2007 | Mehi et al. | |
| 7,301,636 B2 | 11/2007 | Jung et al. | 356/402 |
| 7,382,907 B2 | 6/2008 | Luo et al. | 382/128 |
| 7,450,746 B2 | 11/2008 | Yang et al. | 382/131 |
| 7,520,857 B2 | 4/2009 | Chalana et al. | 600/446 |
| 7,611,466 B2 | 11/2009 | Chalana et al. | 600/443 |
| 2001/0031920 A1 | 10/2001 | Kaufman et al. | 600/431 |
| 2002/0005071 A1 | 1/2002 | Song et al. | 73/606 |
| 2002/0016545 A1 | 2/2002 | Quistgaard et al. | 600/437 |
| 2002/0072671 A1 | 6/2002 | Chenal et al. | 600/450 |
| 2002/0102023 A1 | 8/2002 | Yamauchi et al. | 382/199 |
| 2002/0133075 A1 | 9/2002 | Abdelhak | 600/443 |
| 2002/0147399 A1 | 10/2002 | Mao et al. | 600/458 |
| 2002/0165448 A1 | 11/2002 | Ben-Haim et al. | 600/424 |
| 2003/0055336 A1 | 3/2003 | Buck et al. | 600/453 |
| 2003/0142587 A1 | 7/2003 | Zeitzew | 367/127 |
| 2003/0174872 A1 | 9/2003 | Chalana et al. | 382/128 |
| 2003/0181806 A1 | 9/2003 | Medan et al. | 600/411 |
| 2003/0216646 A1 | 11/2003 | Angelsen et al. | 600/437 |
| 2003/0229281 A1 | 12/2003 | Barnard et al. | 600/438 |
| 2004/0006266 A1 | 1/2004 | Ustuner et al. | 600/47 |
| 2004/0024302 A1 | 2/2004 | Chalana et al. | 600/407 |
| 2004/0034305 A1 | 2/2004 | Song et al. | 600/447 |
| 2004/0054280 A1 | 3/2004 | McMorrow et al. | 600/437 |
| 2004/0076317 A1 | 4/2004 | Roberts | 328/128 |
| 2004/0106869 A1 | 6/2004 | Tepper | 600/443 |
| 2004/0127796 A1 | 7/2004 | Chalana et al. | 600/449 |
| 2004/0127797 A1 | 7/2004 | Barnard et al. | 600/449 |
| 2004/0267123 A1 | 12/2004 | McMorrow et al. | 600/443 |
| 2005/0135707 A1 | 6/2005 | Turek et al. | 382/294 |
| 2005/0174324 A1 | 8/2005 | Liberty et al. | 345/156 |
| 2005/0193820 A1 | 9/2005 | Sheljaskow et al. | 73/649 |
| 2005/0212757 A1 | 9/2005 | Marvit et al. | 345/156 |
| 2005/0215896 A1 | 9/2005 | McMorrow et al. | 600/437 |
| 2005/0228276 A1 | 10/2005 | He et al. | 600/437 |
| 2005/0240126 A1 | 10/2005 | Foley et al. | |
| 2005/0253806 A1 | 11/2005 | Liberty et al. | 345/156 |
| 2006/0025689 A1 | 2/2006 | Chalana et al. | 600/456 |
| 2006/0064010 A1 | 3/2006 | Cannon, Jr. et al. | 600/434 |
| 2006/0078501 A1 | 4/2006 | Goertz et al. | 424/9.52 |
| 2006/0079712 A1 | 4/2006 | McMorrow et al. | 600/443 |
| 2006/0111633 A1 | 5/2006 | McMorrow et al. | 600/437 |
| 2006/0235301 A1 | 10/2006 | Chalana et al. | 600/443 |
| 2007/0004983 A1 | 1/2007 | Chalana et al. | 600/443 |
| 2007/0232908 A1 | 10/2007 | Wang et al. | 600/437 |
| 2007/0276247 A1 | 11/2007 | Chalana et al. | 600/447 |
| 2007/0276254 A1 | 11/2007 | Yang et al. | 600/463 |
| 2008/0139938 A1 | 6/2008 | Yang et al. | 600/445 |
| 2008/0146932 A1 | 6/2008 | Chalana et al. | 600/447 |
| 2008/0242985 A1 | 10/2008 | Chalana et al. | 600/443 |
| 2008/0249414 A1 | 10/2008 | Yang et al. | 600/445 |
| 2008/0262356 A1 | 10/2008 | Chalana et al. | 600/447 |
| 2009/0062644 A1 | 3/2009 | McMorrow et al. | 600/437 |
| 2009/0088660 A1 | 4/2009 | McMorrow et al. | 600/546 |
| 2009/0105585 A1 | 4/2009 | Wang et al. | 600/437 |
| 2009/0112089 A1 | 4/2009 | Barnard et al. | 600/443 |
| 2009/0264757 A1 | 10/2009 | Yang et al. | 600/443 |

FOREIGN PATENT DOCUMENTS

| | | |
|---|---|---|
| EP | 1 030 187 | 8/2000 |
| EP | 1 076 318 | 2/2001 |
| GB | 2 391 625 | 2/2004 |
| JP | 7-171149 | 7/1995 |
| JP | 2000-210286 | 8/2000 |
| JP | 2000-126178 | 9/2000 |
| JP | 2000-126181 | 9/2000 |
| JP | 2000-126182 | 9/2000 |
| WO | 01/35339 | 5/2001 |
| WO | 2009/032778 | 3/2009 |

OTHER PUBLICATIONS

Baker, A., et al., "Prediction of Non-Linear Propagation in Water Due to Diagnostic Medical Ultrasound Equipment", Phys. Med Biol., vol. 36, No. 11, pp. 1457-1464, 1991.

Barentsz et al., "Primary Staging of Urinary Bladder Carcinoma: the Role of MRI and a Comparison with CT," European Radiology vol. 6, pp. 129-133, 1996.

Besl, P., et al., "A Method for Registration of 3-D Shapes," IEEE Transaction on Pattern Analysis and Machine Intelligence, vol. 14, No. 2, pp. 239-256, Feb. 1992.

Birnholz, J., et al., "Amniotic Fluid Accumulation in the First Trimester," American Institute of Ultrasound in Medicine, Journal Ultrasound Medicine, vol. 14, pp. 597-602, 1995.

Bishop, S., et al., "Human Tissue-Temperature Rise During Ultrasound Treatments with the Aquaflex Gel Pad." Journal of Athletic Training, vol. 39, No. 2, pp. 126-131, 2004.

Bouakaz, A., et al., "Noninvasive Bladder Volume Measurements Based on Nonlinear Wave Distortion," Ultrasound in Medicine & Biology, vol. 30, No. 4, pp. 469-476, 2004.

Boyle, P., et al, "Prostate Volume Predicts Outcome of Treatment of Benign Prostatic Hyperplasia with Finasteride: Meta-Analysis of Randomized Clinical Trials," Urology, vol. 48, No. 3, pp. 398-405, 1996.

Cascione, C., et al., "Transabdominal Ultrasound Versus Excretory Urography in Preoperative Evaluation of Patients with Prostatism," The Journal of Urology, vol. 137, pp. 883-885, May 1987.

Chamberlain, P., "Amniotic Fluid Volume: Ultrasound Assessment and Clinical Significance," Seminars in Perinateology, vol. 9, No. 4, pp. 163-167, 1985.

Chamberlain, P. "Ultrasound Evaluation of Amniotic Fluid Volume," American Journal of Obstetrics and Gynaecology, vol. 150, No. 3, pp. 250-254, Oct. 1, 1984.

Cheng, X. et al., "Boundary Extraction Method for Three Dimensional Ultrasonic Echo Imaging Using Fuzzy Reasoning and Relaxation Techniques," IEEE, pp. 1610-1614, 1994.

Christensen, M., et al., "Clinical Manifestations of Benign Prostatic Hyperplasia and Indications for Therapeutic Intervention," Benign Prostatic Hyperplasia, Urologic Clinics of North America, vol. 17, No. 3, pp. 509-516, Aug. 1990.

Crowley, P., et al., "The Value of Ultrasound Measurement of Amniotic Fluid Volume in the Management of Prolonged Pregnancies," British Journal of Obstetrics and Gynaecology, vol. 91, pp. 444-448, May 1984.

Cvitkovic-Kuzmic, A., et al., "Sonographic Measurement of Detrusor Muscle Thickness in Healthy Children," Pedatric Nephrology, vol. 16, pp. 1122-1125, 2001.

Cvitkovic-Kuzmic, A., et al., "Ultrasound Assessment of Detrusor Muscle Thickness in Children with Non-Neuropathic Bladder/Sphincter Dysfunction," European Urology, Vo. 41, pp. 214-219, 2002.

Elliott, P., "Interactive Image Segmentation for Radiation Treatment Planning," IBM Systems Journal, vol. 31, No. 4, pp. 620-634, 1992.

Forbes, F., et al., "Bayesian Morphology: Fast Unsupervised Bayesian Image Analysis," Journal of the American Statistical Association, vol. 94, No. 446, pp. 555-568, Jun. 1999.

Gramellini, D., et al., "Sonographic Assessment of Amniotic Fluid Volume Between 11 and 24 Weeks of Gestation: Construction of Reference Intervals Related to Gestational Age," Ultrasound Obstetrics Gynaecology, vol. 17, pp. 410-415, 2001.

Grover, J., et al., "Three-Dimensional Method for Determination of Amniotic Fluid Volume in Intrauterine Pockets," vol. 90, No. 6, pp. 1007-1010, Dec. 1997.

Hakenberg, O., et al., "Bladder Wall Thickness in Normal Adults and Men with Mild Lower Urinary Tract Symptoms and Benign Prostatic Enlargement," Neurourology and Urodynamics, vol. 19, pp. 585-593, 2000.

Hakenberg, O., et al., "The Estimation of Bladder Volume by Sonocystrography," Journal of Urology, vol. 130, No. 2, pp. 249-251, Aug. 1983.

Hamilton, M., et al., "Nonlinear Acoustics," Copyright 1998 by Academic Press, Chapter 4, 'Progressive Waves in Lossless and Lossy Fluids,' pp. 65-150.

Holmes, J., et al., "Ultrasonic Studies of the Bladder," The Journal of Urology, vol. 91, pp. 654-663, 1967.

Jeng, C., et al., "Amniotic Fluid Index Measurement with the Four-Quadrant Technique During Pregnancy," The Journal of Reproductive Medicine, Inc., vol. 35, No. 7, pp. 674-677, Jul. 1990.

Jequier, S., et al., "Sonographic Measurements of the Normal Bladder Wall in Children," AJR, vol. 149, pp. 563-566, Sep. 1987.

Jong, et al., "Ultrasound Contrast Agents" ISBN 1-85317-858-4 chapter 3 "Contrast-Specific Imaging Methods".

Khullar, V., et al. "A Novel Technique for Measuring Bladder Wall Thickness in Women Using Transvaginal Ultrasound," Ultrasound Obestetrics and Gynaecology, vol. 4, pp. 220-223, 1994.

Khullar, V., et al., "Ultrasound: a Noninvasive Screening Test for Detrusor Instability," British Journal of Obstetrics and Gynaecology, vol. 103, pp. 904-908, Sep. 1996.

Kojima, M., et al., "Reversible Change of Bladder Hypertrophy Due to Benign Prostatic Hyperplasia After Surgical Relief of Obstruction," The Journal of Urology, vol. 158, pp. 89-93, Jul. 1997.

Kojima, M., et al., "Ultrasonic Estimation of Bladder Weight as a Measure of Bladder Hypertrophy in Men with Infravesical Obstruction: a Preliminary Report," Urology, vol. 47, No. 6, pp. 942-947, 1996.

Krenning, B., et al., "Assessment of Left Ventricular Function by Three-Dimensional Echocardiography," Cardiovascular Ultrasound, 7 pgs., 2003.

Kruczkowski et al., "A Non-Invasive Ultrasonic System to Determine Residual Bladder Volumes", IEEE Engineering in Medicine Biology Society 10th Ann Conf, pp. 1623-1624.

Lea, J., et al., "Registration and Immobilization in Robot-Assisted Surgery," Computer Aided Surgery, vol. 1, No. 2, pp. 80-87, 1995.

Lorensen, W., et al., "Marching Cubes: A High Resolution 3D Surface Construction Algorithm," ACM Siggraph Computer Graphics, vol. 21, No. 4, pp. 163-169, Jul. 1987.

Madsen, F., et al., "Clinical Manifestations of Benign Prostatic Hyperplasia," Advances in Benign Prostatic Hyperplasia, Urologic Clinics of North America, vol. 22, No. 2, pp. 291-298, May 1995.

Magann, E., et al., "Amniotic Fluid Volume Determination," American Journal of Obstetrics and Gyneacology, Vo. 169, No. 2, Part 1, pp. 435-437, 1999.

Magann, E., et al., "Measurement of Amniotic Fluid Volume: Accuracy of Ultrasonography Techniques," American Journal of Obstetrics and Gyneacology, vol. 167, No. 6, pp. 1533-1537, 1992.

Magann, E., et al., "Ultrasound Estimate of Amniotic Fluid Volume: Color Doppler Overdiagnosis of Oligohydramnios," Obstetrics & Gynecology, vol. 98, No. 1, pp. 71-74, Jul. 2001.

Magann, E., et al., "Ultrasound Estamation of Amniotic Fluid Volume Using the Largest Vertical Pocket Containing Umbilical Cord: Measure to or Through the Cord," Ultrasound Obstetrics and Gynecology, vol. 20, pp. 464-467, 2002.

Manieri, C., et al., "The Diagnosis of Bladder Outlet Obstruction in Men by Ultrasound Measurement of Bladder Wall Thickness," The Journal of Urology, vol. 159, 761-765, pp. 761-765, Mar. 1998.

Mann, S., et al., "Novel Technique for Assessing Amniotic Fluid Volume: use of a Three-Dimensional Bladder Scanner," The Journal of Maternal-Fetal Medicine, vol. 9, pp. 308-310, 2000.

Manning, F., et al., "Qualitative Amniotic Fluid Volume Determination by Ultrasound: Antepartum Detection of Intrauterine Growth Retardation," American Journal of Obstetrics and Gynecology, vol. 139, No. 3, pp. 254-258, Feb. 1, 1981.

Martan, A., et al., "Ultrasound Imaging of the Lower Urinary System in Women after Burch Colposuspension," Ultrasound Obstetrics and Gynecology, vol. 17, pp. 58-64, 2001.

Matthews, P. et al., "The Use of Ultrasound in the Investigation of Prostatism," British Journal of Urology, vol. 54, pp. 536-538, 1982.

Merks, E. et al., "Design of a Multilayer Transducer for Acoustic Bladder Volume Assessment," IEEE Transacations on Ultrasonics, Ferroelectrics and Frequency Control, vol. 53, No. 10, pp. 1730-1738, Oct. 2006.

Merks, E., et al., "A KLM-Circuit Model of a Multi-Layer Transducer for Acoustic Bladder Volume Measurements," Ultrasonics, vol. 44, pp. 705-710, Dec. 22, 2006.

Miyashita, H., et al., "Ultrasonic Measurement of Bladder Weight as a Possible Predictor of Acute Urinary Retention in Men with Lower Urinary Tract Symptoms Suggestive of Benign Prostatic Hyperplasia," Ultrasound in Medicine & Biology, vol. 28, No. 8, pp. 985-990, 2002.

Moore, T., "Superiority of the Four-Quadrant Sum Over the Single-Deepest-Pocket Technique in Ultrasonographic Identification of Abnormal Amniotic Fluid Volumes," American Journal of Obstetrics and Gynecology, vol. 163, No. 5, pp. 762-767, 1990.

Muller, L., et al., "Detrusor Thickness in Healthy Children Assessed by a Standardized Ultrasound Method," The Journal of Urology, vol. 166, pp. 2364-2367, Dec. 2001.

Muller, L., et al., "Standardized Ultrasound Method for Assessing Detrusor Muscle Thickness in Children," The Journal of Urology, vol. 164, pp. 134-138, Jul. 2000.

Myles, T., et al., "Four-Quadrant Assessment of Amniotic Fluid Volume: Distribution's Role in Predicting Fetal Outcome," Journal of Obstetrics and Gynecology, vol. 80, No. 5, pp. 769-774, Nov. 1992.

Naya, Y., et al., "Intraobserver and Interobserver Variance in the Measurement of Ultrasound-Estimated Bladder Weight," Ultrasound in Medicine and Biology, vol. 24, No. 5, pp. 771-773, 1998.

Oelke, M., et al., "Increase in Detrusor Wall Thickness Indicates Bladder Outlet Obstruction (BOO) in Men," World Journal of Urology, vol. 19, pp. 443-452, 2002.

Ohashit, G., et al., "Boundary Estimation for Ultrasonic 3-D Imaging," SPIE vol. 1898 Image Processing, pp. 480-486, 1993.

Oomen, JA, et al., "Towards Assessment of Regional Wall Stress of the Left Ventricle Using 3D Ultrasound Imaging," IEEE Computers in Cardiology, vol. 26, pp. 129-132, 1999.

Phelan, J., et al., Amniotic Fluid Volume Assessment with the Four-Quadrant Technique at 36-42 Weeks' Gestation, The Journal of Reproductive Medicine, vol. 32, No. 7, pp. 540-542, Jul. 1987.

Rutherford, S., et al., "The Four-Quadrant Assessment of Amniotic Fluid Volume: An Adjunct to Antepartum Fetal Heart Rate Testing," Journal of Obstetrics and Gynecology, vol. 70, No. 3, Part 1, pp. 353-356, Sep. 1987.

Sagiv, C., et al., "Application of a Semiautomatic Boundary Detection Algorithm for the Assessment of Amniotic Fluid Quantity Form Ultrasound Images," Ultrasound in Medicine and Biology, vol. 25, No. 4, pp. 515-526, 1999.

Sahin, B., et al., "Estimation of the Amniotic Fluid Volume Using the Cavalieri Method on Ultrasound Images," International Journal of Gynecology and Obstetrics, vol. 82, pp. 25-30, 2003.

Santilli, J., et al., "Diagnosis and Treatment of Abdominal Aortic Aneurysms," American Family Physician, vol. 56, No. 4, pp. 1081-1090, Sep. 1997.

Scheinerman, E., "Invitation to Dynamical Systems," Chapter 5, 'Fractals,' Prentice Hall pp. 231-315, 1996.

Schiff, E., et al., "Standardized Measurement of Amniotic Fluid Volume by Correlation of Sonography with Dye Dilution Technique," Obestetrics and Gynecology, vol. 76, No. 1, pp. 44-46, Jul. 1990.

Schrimmer, D., et al., "Sonographic Evaluation of Amniotic Fluid Volume," Clinical Obstetrics and Gynecology, vol. 45, No. 4, pp. 1026-1029, 2002.

Sepulveda W., et al., "Direct Volume Measurement at Midtrimester Amnioinfusion in Relation to Ultrasonographic Indexes of Amniotic Fluid Volume," American Journal of Obstetrics and Gynecology, vol. 170, No. 4, pp. 1160-1163, Apr. 1994.

Shiota, T., et al., "Real-time Three-Dimensional Echocardiography for Determining Right Ventricular Stroke Volume in an Animal Model of Chronic Right Ventricular Volume Overload," Circulation Journal of the American Heart Association, vol. 97, pp. 1897-1900, 1998.

Stangenberg, M., et al., "Amniotic Fluid Volumes in Pregnant Diabetics During the Last Trimester," Acta Obstetrics Gynecology Scand, vol. 61, pp. 313-316, 1982.

Szabo, T., et al., "Effects of Nonlinearity on the Estimation of in Situ Values of Acoustic Output Parameters," Journal of Ultrasound in Medicine, American Institute of of Ultrasound in Medicine, vol. 18, No. 1, pp. 33-41, 1999.

Weissman, A., et al., "Sonographic Measurement of Amniotic Fluid Volume in the First Trimester of Pregnancy," American Institute of Ultrasound in Medicine, vol. 15, pp. 771-774, 1996.

* cited by examiner

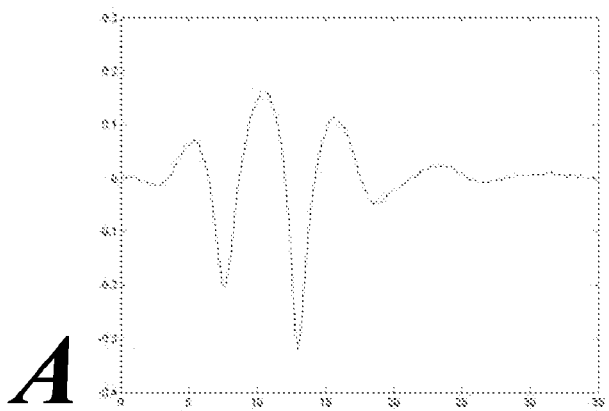
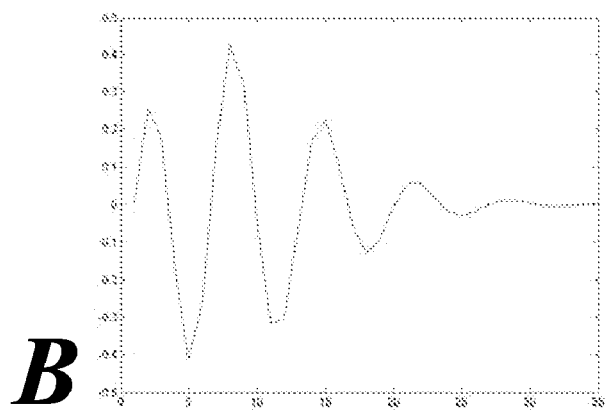
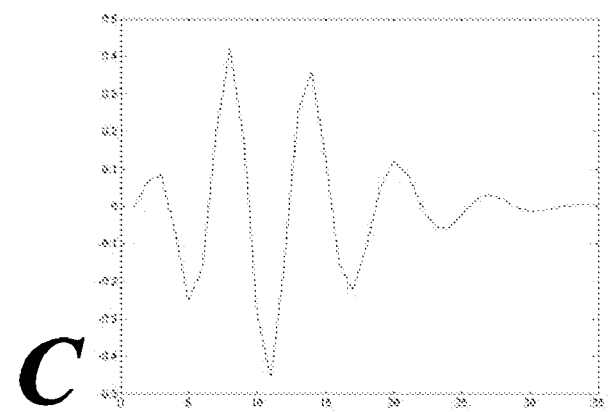
*Fig. 12A-C*

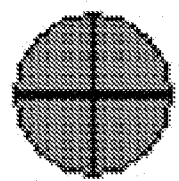 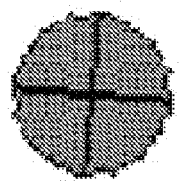 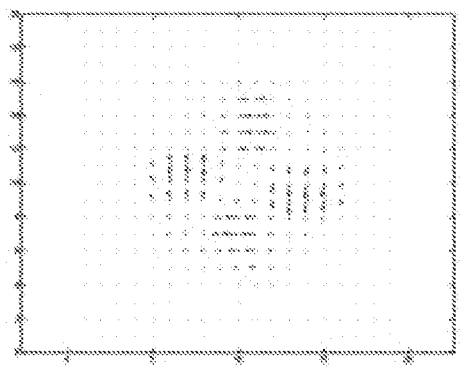
Time = t         Time = t + 1         Velocity Map
*Fig. 26*

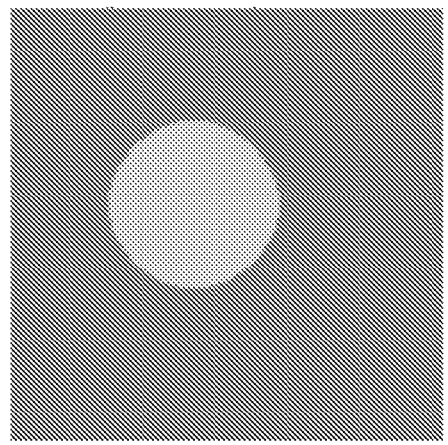
Time = t
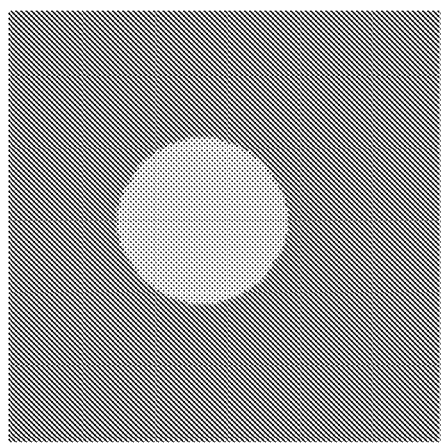
Time = t + 1
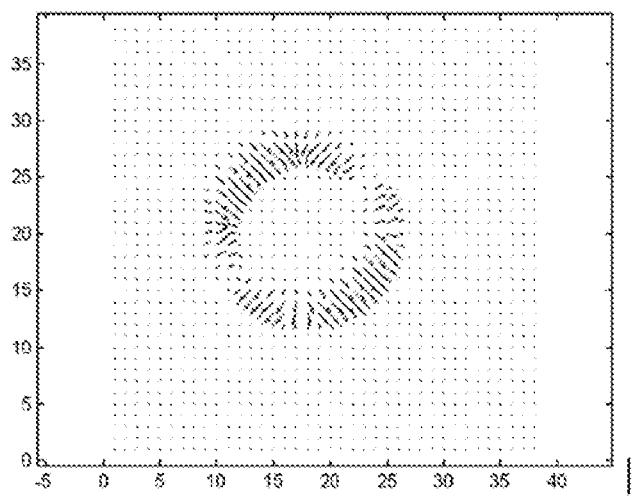
Velocity Map
*Fig. 27*

Optical vector value in 3D view:

Optical vector in x 3D view (phi direction):

1012-030d-7439 at time 1 and time 2
usOFy = 389.2912
usOFx = 2.1226e+003

Optical vector in y 3D view (radial)

After threshold on y (radial) at 0.6

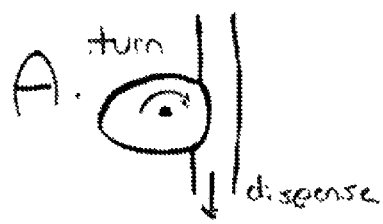
(A) peristaltic mechanism
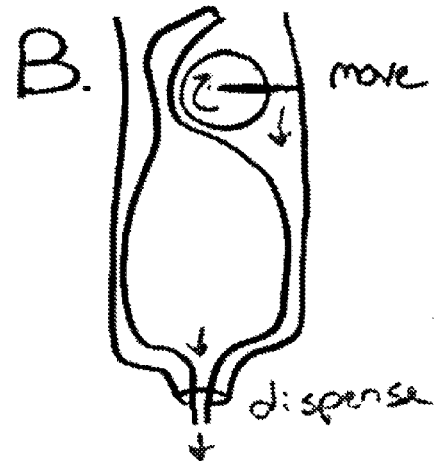
(B) progressively compressing a flexible bag
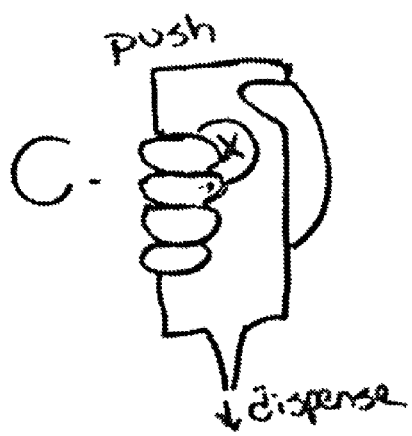
(C) grip dispenser
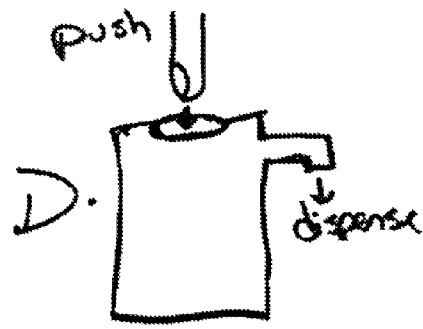
(D) button dispenser
*Figs. 36A-D*

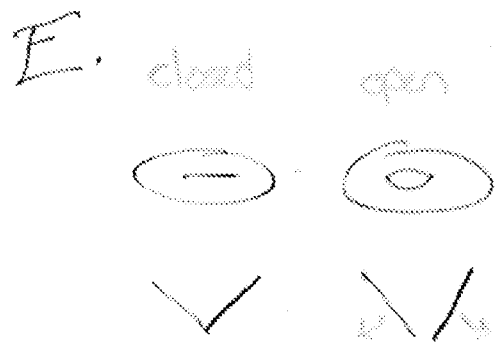
(E) valve to close off gel port after dispensing
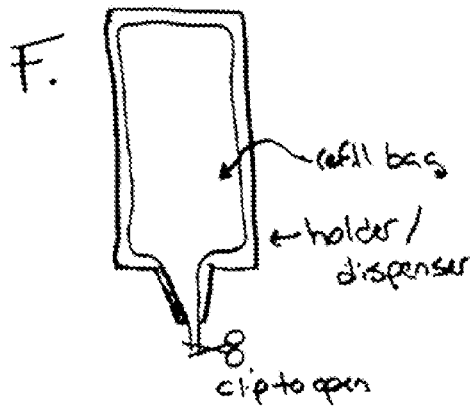
(F) pre-packaged gel bags fit into dispenser
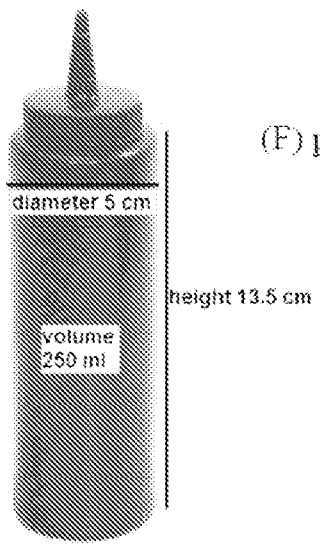
(G) appearance and dimensions of an 8-oz squeeze bottle
*Figs. 36E-G*

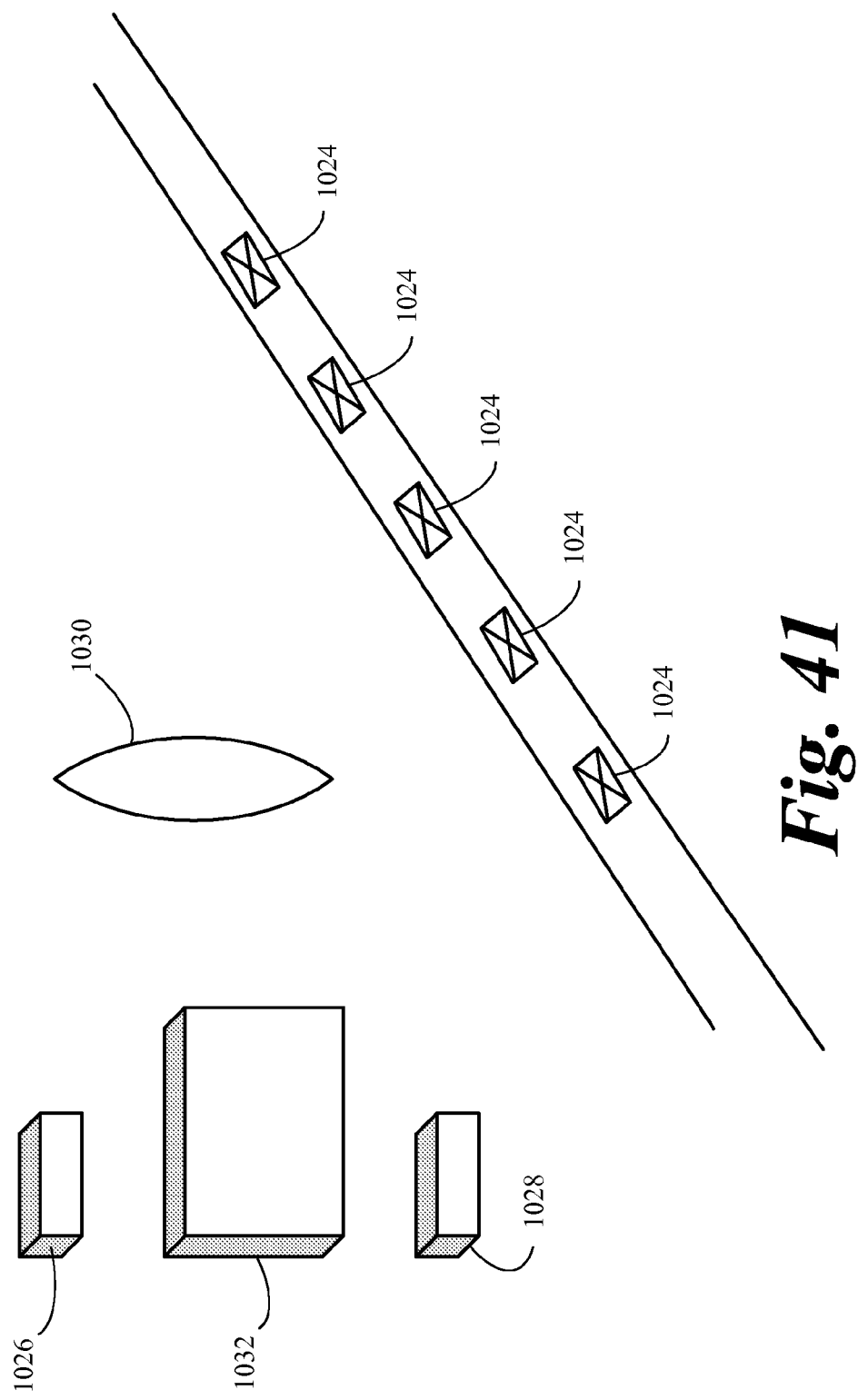

SYSTEMS AND METHODS TO IMPROVE CLARITY IN ULTRASOUND IMAGES

RELATED APPLICATIONS

This application incorporates by reference and claims priority to U.S. provisional patent application Ser. No. 11/625,805 filed Jan. 22, 2007.

This application incorporates by reference and claims priority to U.S. provisional patent application Ser. No. 60/882,888 filed Dec. 29, 2006.

This application incorporates by reference and claims priority to U.S. provisional patent application Ser. No. 60/828,614 filed Oct. 6, 2006.

This application incorporates by reference and claims priority to U.S. provisional patent application Ser. No. 60/760,677 filed Jan. 20, 2006.

This application incorporates by reference and claims priority to U.S. provisional patent application Ser. No. 60/778,634 filed Mar. 1, 2006.

This application is a continuation-in-part of and claims priority to U.S. patent application Ser. No. 11/213,284 filed Aug. 26, 2005.

This application claims priority to and is a continuation-in-part of U.S. patent application Ser. No. 11/119,355 filed Apr. 29, 2005, which claims priority to U.S. provisional patent application Ser. No. 60/566,127 filed Apr. 30, 2004. This application also claims priority to and is a continuation-in-part of U.S. patent application Ser. No. 10/701,955 filed Nov. 5, 2003, which in turn claims priority to and is a continuation-in-part of U.S. patent application Ser. No. 10/443,126 filed May 20, 2003.

This application claims priority to and is a continuation-in-part of U.S. patent application Ser. No. 11/061,867 filed Feb. 17, 2005, which claims priority to U.S. provisional patent application Ser. No. 60/545,576 filed Feb. 17, 2004 and U.S. provisional patent application Ser. No. 60/566,818 filed Apr. 30, 2004.

This application is also a continuation-in-part of and claims priority to U.S. patent application Ser. No. 11/222,360 filed Sep. 8, 2005.

This application is also a continuation-in-part of and claims priority to U.S. patent application Ser. No. 11/061,867 filed Feb. 17, 2005.

This application is also a continuation-in-part of and claims priority to U.S. patent application Ser. No. 10/704,966 filed Nov. 10, 2004.

This application claims priority to and is a continuation-in-part of U.S. patent application Ser. No. 10/607,919 filed Jun. 27, 2005.

This application is a continuation-in-part of and claims priority to PCT application serial number PCT/US03/24368 filed Aug. 1, 2003, which claims priority to U.S. provisional patent application Ser. No. 60/423,881 filed Nov. 5, 2002 and U.S. provisional patent application Ser. No. 60/400,624 filed Aug. 2, 2002.

This application is also a continuation-in-part of and claims priority to PCT Application Serial No. PCT/US03/14785 filed May 9, 2003, which is a continuation of U.S. patent application Ser. No. 10/165,556 filed Jun. 7, 2002.

This application is also a continuation-in-part of and claims priority to U.S. patent application Ser. No. 10/888,735 filed Jul. 9, 2004.

This application is also a continuation-in-part of and claims priority to U.S. patent application Ser. No. 10/633,186 filed Jul. 31, 2003 which claims priority to U.S. provisional patent application Ser. No. 60/423,881 filed Nov. 5, 2002 and to U.S. patent application Ser. No. 10/443,126 filed May 20, 2003 which claims priority to U.S. provisional patent application Ser. No. 60/423,881 filed Nov. 5, 2002 and to U.S. provisional application 60/400,624 filed Aug. 2, 2002. All of the above applications are incorporated by reference in their entirety as if fully set forth herein.

FIELD OF THE INVENTION

Embodiments of the invention pertain to the field of improving the clarity of ultrasound images. Other embodiments of this invention relate to visualization methods and systems, and more specifically to systems and methods for visualizing the trajectory of a cannula or needle being inserted in a biologic subject.

BACKGROUND OF THE INVENTION

The clarity of ultrasound acquired images is affected by motions of the examined subject, the motions of organs and fluids within the examined subject, the motion of the probing ultrasound transceiver, the coupling medium used transceiver and the examined subject, and the algorithms used for image processing. As regards image processing frequency domain approaches have been utilized in the literature including using Wiener filters that is implemented in the frequency domain and assumes that the point spread function (PSF) is fixed and known. This assumption conflicts with the observation that the received ultrasound signals are usually non-stationary and depth-dependent. Since the algorithm is implemented in the frequency domain, the error introduced in PSF will leak across the spatial domain. As a result, the performance of Wiener filtering is not ideal.

As regards prior uses of coupling mediums, the most common container for dispensing ultrasound coupling gel is an 8 oz. plastic squeeze bottle with an open, tapered tip. The tapered tip bottle is inexpensive and easy to refill from a larger reservoir in the form of a bag or pump-type and dispenses gel in a controlled manner. Other embodiments include the Sontac® ultrasound gel pad available from Verathon™ Medical, Bothell, Wash., USA is a pre-packaged, circular pad of moist, flexible coupling gel 2.5 inches in diameter and 0.06 inches thick and is advantageously used with the BladderScan devices. The Sontac pad is simple to apply and to remove, and provides adequate coupling for a one-position ultrasound scan in most cases. Yet others include the Aquaflex® gel pads perform in a similar manner to Sontac pads, but are larger and thicker (2 cm thick×9 cm diameter), and traditionally used for therapeutic ultrasound or where some distance between the probe and the skin surface ("stand-off") must be maintained.

The main purpose of an ultrasonic coupling medium is to provide an air-free interface between an ultrasound transducer and the body surface. Gels are used as coupling media since they are moist and deformable, but not runny: they wet both the transducer and the body surface, but stay where they are applied. The most common delivery method for ultrasonic coupling gel, the plastic squeeze bottle, has several disadvantages. First, if the bottle has been stored upright the gel will fall to the bottom of the bottle, and vigorous shaking is required to get the gel back to the bottle tip, especially if the gel is cold. This motion can be particularly irritating to sonographers, who routinely suffer from wrist and arm pain from ultrasound scanning. Second, the bottle tip is a two-way valve: squeezing the bottle releases gel at the tip, but releasing the bottle sucks air back into the bottle and into the gel. The presence of air bubbles in the gel may detract from its performance as a coupling medium. Third, there is no standard application amount: inexperienced users such as Diagnostic Ultrasound customers have to make an educated guess about how much gel to use. Fourth, when the squeeze bottle is nearly empty it is next to impossible to coax the final 5-10% of gel into the bottle's tip for dispensing. Finally, although refilling the bottle from a central source is not a particularly difficult task, it is non-sterile and potentially messy.

Sontac pads and other solid gel coupling pads are simpler to use than gel: the user does not have to guess at an appropriate application amount, the pad is sterile, and it can be simply lifted off the patient and disposed of after use. However, pads do not mold to the skin or transducer surface as well as the more liquefied coupling gels and therefore may not provide ideal coupling when used alone, especially on dry, hairy, curved, or wrinkled surfaces. Sontac pads suffer from the additional disadvantage that they are thin and easily damaged by moderate pressure from the ultrasound transducer. (See Bishop S, Draper D O, Knight K L, Feland J B, Eggett D. "Human tissue-temperature rise during ultrasound treatments with the Aquaflex gel pad." Journal of Athletic Training 39(2):126-131, 2004).

Relating to cannula insertion, unsuccessful insertion and/or removal of a cannula, a needle, or other similar devices into vascular tissue may cause vascular wall damage that may lead to serious complications or even death. Image guided placement of a cannula or needle into the vascular tissue reduces the risk of injury and increases the confidence of healthcare providers in using the foregoing devices. Current image guided placement methods generally use a guidance system for holding specific cannula or needle sizes. The motion and force required to disengage the cannula from the guidance system may, however, contribute to a vessel wall injury, which may result in extravasation. Complications arising from extravasation resulting in morbidity are well documented. Therefore, there is a need for image guided placement of a cannula or needle into vascular tissue while still allowing a health care practitioner to use standard "free" insertion procedures that do not require a guidance system to hold the cannula or needle.

SUMMARY OF THE PARTICULAR EMBODIMENTS

Systems, methods, and devices for image clarity of ultrasound-based images are described. Such systems, methods, and devices include improved transducer aiming and utilizing time-domain deconvolution processes upon the non-stationary effects of ultrasound signals. The processes deconvolution applies algorithms to improve the clarity or resolution of ultrasonic images by suppressed reverberation of ultrasound echoes. The initially acquired and distorted ultrasound image is reconstructed to a clearer image by countering the effect of distortion operators. An improved point spread function (PSF) of the imaging system is applied, utilizing a deconvolution algorithm, to improve the image resolution, and remove reverberations by modeling them as noise.

As regards improved transducer aiming particular embodiments employ novel applications of computer vision techniques to perform real time analysis. First, a computer vision method is introduced: optical flow, which is a powerful motion analysis technique and is applied in many different research or commercial fields. The optical flow is able to estimate the velocity field of image series and the velocity vector provides information of the contents inside the image series. In the current field, if the target is with very large motion and the motion is in a specific pattern, like moving orientation, the velocity information inside and around the target can be different from other parts in the field. Otherwise, there will be no valuable information in current field and the scanning has to be adjusted.

As regards analyzing the motions of organ movement and fluid flows within an examined subject, new optical-flow-based methods for estimating heart motion from two-dimensional echocardiographic sequences, an optical-flow guided active contour method for Myocardial tracking in contrast echocardiography, and a method for shape-driven segmentation and tracking of the left ventricle.

As regards cannula insertion, ultrasound motion of the cannula is configured by cannula fitted with echogenic ultrasound micro reflectors.

As regards sonic coupling gel media to improve ultrasound communication between a transducer and the examined subject, embodiments include an apparatus that: dispenses a metered quantity of ultrasound coupling gel and enables one-handed gel application. The apparatus also preserves the gel in a de-gassed state (no air bubbles), preserves the gel in a sterile state (no contact between gel applicator and patient), includes a method for easy container refill, and preserves the shape and volume of existing gel application bottles.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee. Embodiments for the system and method to develop, present, and use clarity enhanced ultrasound images is described below.

FIGS. 12A-C depict histogram waveform plots derived from water tank pulse-echo experiments undergoing parametric and non-parametric analysis;

FIG. 13 is an unprocessed image that will undergo image enhancement processing;

FIG. 14 illustrates an enclosed portion of a magnified region of FIG. 13;

FIG. 15 is the resultant image of FIG. 13 that has undergone image processing via nonparametric estimation under sub-algorithm 400A;

FIG. 16 is the resultant image of FIG. 13 that has undergone image processing via parametric estimation under sub-algorithm 400B;

FIG. 17 the resultant image of an alternate image processing embodiment using a Weiner filter.

FIG. 18 is another unprocessed image that will undergo image enhancement processing;

FIG. 19 illustrates an enclosed portion of a magnified region of FIG. 18;

FIG. 20 is the resultant image of FIG. 18 that has undergone image processing via nonparametric estimation under sub-algorithm 400A;

FIG. 21 is the resultant image of FIG. 18 that has undergone image processing via parametric estimation under sub-algorithm 400B;

FIG. 22 is another unprocessed image that will undergo image enhancement processing;

FIG. 23 illustrates an enclosed portion of a magnified region of FIG. 22;

FIG. 24 is the resultant image of FIG. 22 that has undergone image processing via nonparametric estimation under sub-algorithm 400A;

FIG. 25 is the resultant image of FIG. 22 that has undergone image processing via parametric estimation under sub-algorithm 400B;

FIG. 26 depicts a schematic example of a time velocity map derived from sub-algorithm 310;

FIG. 27 depicts another schematic example of a time velocity map derived from sub-algorithm 310;

FIGS. 36A-G depicts embodiments of the sonic gel dispenser;

FIG. 41 is a diagram showing imaging components for use with the needle shaft shown in FIG. 38;

DETAILED DESCRIPTION OF THE PARTICULAR EMBODIMENTS

Systems, methods, and devices for image clarity of ultrasound-based images are described and illustrated in the following figures. The clarity of ultrasound imaging requires the efficient coordination of ultrasound transfer or communication to and from an examined subject, image acquisition from the communicated ultrasound, and microprocessor based image processing. Oftentimes the examined subject moves while image acquisition occurs, the ultrasound transducer moves, and/or movement occurs within the scanned region of interest that requires refinements as described below to secure clear images.

The ultrasound transceivers or DCD devices developed by Diagnostic Ultrasound are capable of collecting in vivo three-dimensional (3-D) cone-shaped ultrasound images of a patient. Based on these 3-D ultrasound images, various applications have been developed such as bladder volume and mass estimation.

During the data collection process initiated by DCD, a pulsed ultrasound field is transmitted into the body, and the back-scattered "echoes" are detected as a one-dimensional (1-D) voltage trace, which is also referred to as a RF line. After envelope detection, a set of 1-D data samples is interpolated to form a two-dimensional (2-D) or 3-D ultrasound image.

FIGS. 1A-D depicts a partial schematic and a partial isometric view of a transceiver, a scan cone comprising a rotational array of scan planes, and a scan plane of the array of various ultrasound harmonic imaging systems 60A-D illustrated in FIGS. 3 and 4 below.

Figure 1:
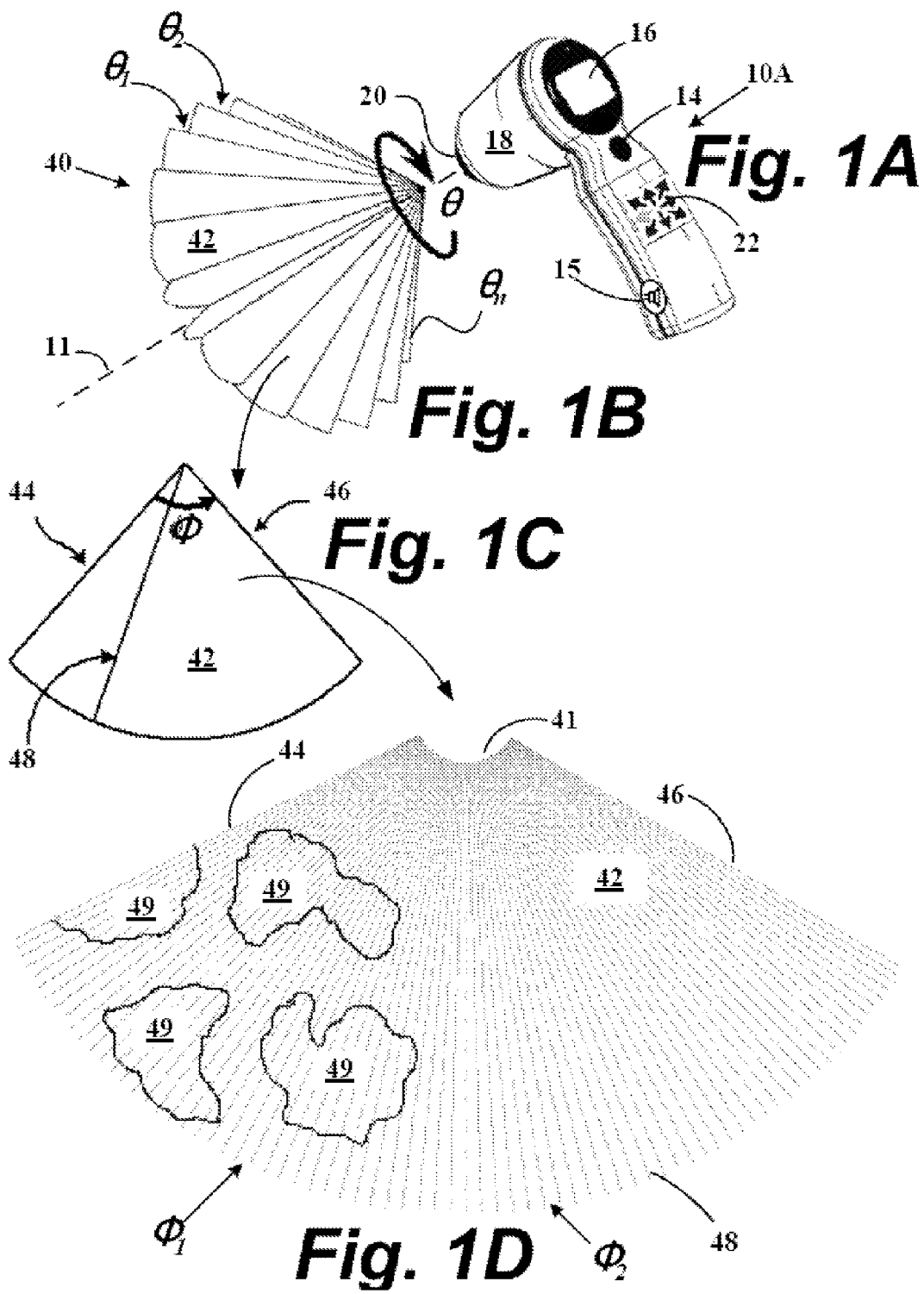
FIGS. 1A-D depicts a partial schematic and a partial isometric view of a transceiver, a scan cone comprising a rotational array of scan planes, and a scan plane of the array of an ultrasound harmonic imaging system.

FIG. 1A is a side elevation view of an ultrasound transceiver 10A that includes an inertial reference unit, according to an embodiment of the invention. The transceiver 10A includes a transceiver housing 18 having an outwardly extending handle 12 suitably configured to allow a user to manipulate the transceiver 10A relative to a patient. The handle 12 includes a trigger 14 that allows the user to initiate an ultrasound scan of a selected anatomical portion, and a cavity selector 16. The cavity selector 16 will be described in greater detail below. The transceiver 10A also includes a transceiver dome 20 that contacts a surface portion of the patient when the selected anatomical portion is scanned. The dome 20 generally provides an appropriate acoustical impedance match to the anatomical portion and/or permits ultrasound energy to be properly focused as it is projected into the anatomical portion. The transceiver 10A further includes one, or preferably an array of separately excitable ultrasound transducer elements (not shown in FIG. 1A) positioned within or otherwise adjacent with the housing 18. The transducer elements may be suitably positioned within the housing 18 or otherwise to project ultrasound energy outwardly from the dome 20, and to permit reception of acoustic reflections generated by internal structures within the anatomical portion. The one or more array of ultrasound elements may include a one-dimensional, or a two-dimensional array of piezoelectric elements that may be moved within the housing 18 by a motor. Alternately, the array may be stationary with respect to the housing 18 so that the selected anatomical region may be scanned by selectively energizing the elements in the array.

A directional indicator panel 22 includes a plurality of arrows that may be illuminated for initial targeting and guiding a user to access the targeting of an organ or structure within an ROI. In particular embodiments if the organ or structure is centered from placement of the transceiver 10A acoustically placed against the dermal surface at a first location of the subject, the directional arrows may be not illuminated. If the organ is off-center, an arrow or set of arrows may be illuminated to direct the user to reposition the transceiver 10A acoustically at a second or subsequent dermal location of the subject. The acrostic coupling may be achieved by liquid sonic gel applied to the skin of the patient or by sonic gel pads to which the transceiver dome 20 is placed against. The directional indicator panel 22 may be presented on the display 54 of computer 52 in harmonic imaging subsystems described in FIGS. 3 and 4 below, or alternatively, presented on the transceiver display 16.

Transceiver 10A includes an inertial reference unit that includes an accelerometer 22 and/or gyroscope 23 positioned preferably within or adjacent to housing 18. The accelerometer 22 may be operable to sense an acceleration of the transceiver 10A, preferably relative to a coordinate system, while the gyroscope 23 may be operable to sense an angular velocity of the transceiver 10A relative to the same or another coordinate system. Accordingly, the gyroscope 23 may be of conventional configuration that employs dynamic elements, or it may be an optoelectronic device, such as the known optical ring gyroscope. In one embodiment, the accelerometer 22 and the gyroscope 23 may include a commonly packaged and/or solid-state device. One suitable commonly packaged device may be the MT6 miniature inertial measurement unit, available from Omni Instruments, Incorporated, although other suitable alternatives exist. In other embodiments, the accelerometer 22 and/or the gyroscope 23 may include commonly packaged micro-electromechanical system (MEMS) devices, which are commercially available from MEMSense, Incorporated. As described in greater detail below, the accelerometer 22 and the gyroscope 23 cooperatively permit the determination of positional and/or angular changes relative to a known position that is proximate to an anatomical region of interest in the patient. Other configurations related to the accelerometer 22 and gyroscope 23 concerning transceivers 10A,B equipped with inertial reference units and the operations thereto may be obtained from copending U.S. patent application Ser. No. 11/222,360 filed Sep. 8, 2005, herein incorporated by reference.

The transceiver 10A includes (or if capable at being in signal communication with) a display 24 operable to view processed results from an ultrasound scan, and/or to allow an operational interaction between the user and the transceiver 10A. For example, the display 24 may be configured to display alphanumeric data that indicates a proper and/or an optimal position of the transceiver 10A relative to the selected anatomical portion. Display 24 may be used to view two- or three-dimensional images of the selected anatomical region. Accordingly, the display 24 may be a liquid crystal display (LCD), a light emitting diode (LED) display, a cathode ray tube (CRT) display, or other suitable display devices operable to present alphanumeric data and/or graphical images to a user.

Still referring to FIG. 1A, a cavity selector 16 may be operable to adjustably adapt the transmission and reception of ultrasound signals to the anatomy of a selected patient. In particular, the cavity selector 16 adapts the transceiver 10A to accommodate various anatomical details of male and female patients. For example, when the cavity selector 16 is adjusted to accommodate a male patient, the transceiver 10A may be suitably configured to locate a single cavity, such as a urinary bladder in the male patient. In contrast, when the cavity selector 16 is adjusted to accommodate a female patient, the transceiver 10A may be configured to image an anatomical portion having multiple cavities, such as a bodily region that includes a bladder and a uterus. Alternate embodiments of the transceiver 10A may include a cavity selector 16 configured to select a single cavity scanning mode, or a multiple cavity-scanning mode that may be used with male and/or female patients. The cavity selector 16 may thus permit a single cavity region to be imaged, or a multiple cavity region, such as a region that includes a lung and a heart to be imaged.

To scan a selected anatomical portion of a patient, the transceiver dome 20 of the transceiver 10A may be positioned against a surface portion of a patient that is proximate to the anatomical portion to be scanned. The user actuates the transceiver 10A by depressing the trigger 14. In response, the transceiver 10 transmits ultrasound signals into the body, and receives corresponding return echo signals that may be at least partially processed by the transceiver 10A to generate an ultrasound image of the selected anatomical portion. In a particular embodiment, the transceiver 10A transmits ultrasound signals in a range that extends from approximately about two megahertz (MHz) to approximately about ten MHz.

In one embodiment, the transceiver 10A may be operably coupled to an ultrasound system that may be configured to generate ultrasound energy at a predetermined frequency and/or pulse repetition rate and to transfer the ultrasound energy to the transceiver 10A. The system also includes a processor that may be configured to process reflected ultrasound energy that is received by the transceiver 10A to produce an image of the scanned anatomical region. Accordingly, the system generally includes a viewing device, such as a cathode ray tube (CRT), a liquid crystal display (LCD), a plasma display device, or other similar display devices, that may be used to view the generated image. The system may also include one or more peripheral devices that cooperatively assist the processor to control the operation of the transceiver 10A, such a keyboard, a pointing device, or other similar devices. In still another particular embodiment, the transceiver 10A may be a self-contained device that includes a microprocessor positioned within the housing 18 and software associated with the microprocessor to operably control the transceiver 10A, and to process the reflected ultrasound energy to generate the ultrasound image. Accordingly, the display 24 may be used to display the generated image and/or to view other information associated with the operation of the transceiver 10A. For example, the information may include alphanumeric data that indicates a preferred position of the transceiver 10A prior to performing a series of scans. In yet another particular embodiment, the transceiver 10A may be operably coupled to a general-purpose computer, such as a laptop or a desktop computer that includes software that at least partially controls the operation of the transceiver 10A, and also includes software to process information transferred from the transceiver 10A, so that an image of the scanned anatomical region may be generated. The transceiver 10A may also be optionally equipped with electrical contacts to make communication with receiving cradles 50 as discussed in FIGS. 3 and 4 below. Although transceiver 10A of FIG. 1A may be used in any of the foregoing embodiments, other transceivers may also be used. For example, the transceiver may lack one or more features of the transceiver 10A. For example, a suitable transceiver need not be a manually portable device, and/or need not have a top-mounted display, and/or may selectively lack other features or exhibit further differences.

Referring still to FIG. 1A is a graphical representation of a plurality of scan planes that form a three-dimensional (3D) array having a substantially conical shape. An ultrasound scan cone 40 formed by a rotational array of two-dimensional scan planes 42 projects outwardly from the dome 20 of the transceivers 10A. The other transceiver embodiments 10B-10E may also be configured to develop a scan cone 40 formed by a rotational array of two-dimensional scan planes 42. The pluralities of scan planes 40 may be oriented about an axis 11 extending through the transceivers 10A-10E. One or more, or preferably each of the scan planes 42 may be positioned about the axis 11, preferably, but not necessarily at a predetermined angular position θ. The scan planes 42 may be mutually spaced apart by angles $\theta_1$ and $\theta_2$. Correspondingly, the scan lines within each of the scan planes 42 may be spaced apart by angles $\phi_1$ and $\phi_2$. Although the angles $\theta_1$ and $\theta_2$ are depicted as approximately equal, it is understood that the angles $\theta_1$ and $\theta_2$ may have different values. Similarly, although the angles $\phi_1$ and $\phi_2$ are shown as approximately equal, the angles $\phi_1$ and $\phi_2$ may also have different angles. Other scan cone configurations are possible. For example, a wedge-shaped scan cone, or other similar shapes may be generated by the transceiver 10A, 10B and 10C.

FIG. 1B is a graphical representation of a scan plane 42. The scan plane 42 includes the peripheral scan lines 44 and 46, and an internal scan line 48 having a length r that extends outwardly from the transceivers 10A-10E. Thus, a selected point along the peripheral scan lines 44 and 46 and the internal scan line 48 may be defined with reference to the distance r and angular coordinate values φ and θ. The length r preferably extends to approximately 18 to 20 centimeters (cm), although any length is possible. Particular embodiments include approximately seventy-seven scan lines 48 that extend outwardly from the dome 20, although any number of scan lines is possible.

FIG. 1C a graphical representation of a plurality of scan lines emanating from a hand-held ultrasound transceiver forming a single scan plane 42 extending through a cross-section of an internal bodily organ. The number and location of the internal scan lines emanating from the transceivers 10A-10E within a given scan plane 42 may thus be distributed at different positional coordinates about the axis line 11 as required to sufficiently visualize structures or images within the scan plane 42. As shown, four portions of an off-centered region-of-interest (ROI) are exhibited as irregular regions 49. Three portions may be viewable within the scan plane 42 in totality, and one may be truncated by the peripheral scan line 44.

As described above, the angular movement of the transducer may be mechanically effected and/or it may be electronically or otherwise generated. In either case, the number of lines 48 and the length of the lines may vary, so that the tilt angle φ sweeps through angles approximately between −60° and +60° for a total arc of approximately 120°. In one particular embodiment, the transceiver 10 may be configured to generate approximately about seventy-seven scan lines between the first limiting scan line 44 and a second limiting scan line 46. In another particular embodiment, each of the scan lines has a length of approximately about 18 to 20 centimeters (cm). The angular separation between adjacent scan lines 48 (FIG. 1B) may be uniform or non-uniform. For example, and in another particular embodiment, the angular separation $\phi_1$ and $\phi_2$ (as shown in FIG. 5C) may be about 1.5°. Alternately, and in another particular embodiment, the angular separation $\phi_1$ and $\phi_2$ may be a sequence wherein adjacent angles may be ordered to include angles of 1.5°, 6.8°, 15.5°, 7.2°, and so on, where a 1.5° separation is between a first scan line and a second scan line, a 6.8° separation is between the second scan line and a third scan line, a 15.5° separation is between the third scan line and a fourth scan line, a 7.2° separation is between the fourth scan line and a fifth scan line, and so on. The angular separation between adjacent scan lines may also be a combination of uniform and non-uniform angular spacings, for example, a sequence of angles may be ordered to include 1.5°, 1.5°, 1.5°, 7.2°, 14.3°, 20.2°, 8.0°, 8.0°, 8.0°, 4.3°, 7.8°, and so on.

FIG. 1D is an isometric view of an ultrasound scan cone that projects outwardly from the transceivers of FIGS. 1A-E. Three-dimensional images of a region of interest may be presented within a scan cone 40 that comprises a plurality of 2D images formed in an array of scan planes 42. A dome cutout 41 that is the complementary to the dome 20 of the transceivers 10A-10E is shown at the top of the scan cone 40.

Figure 2:
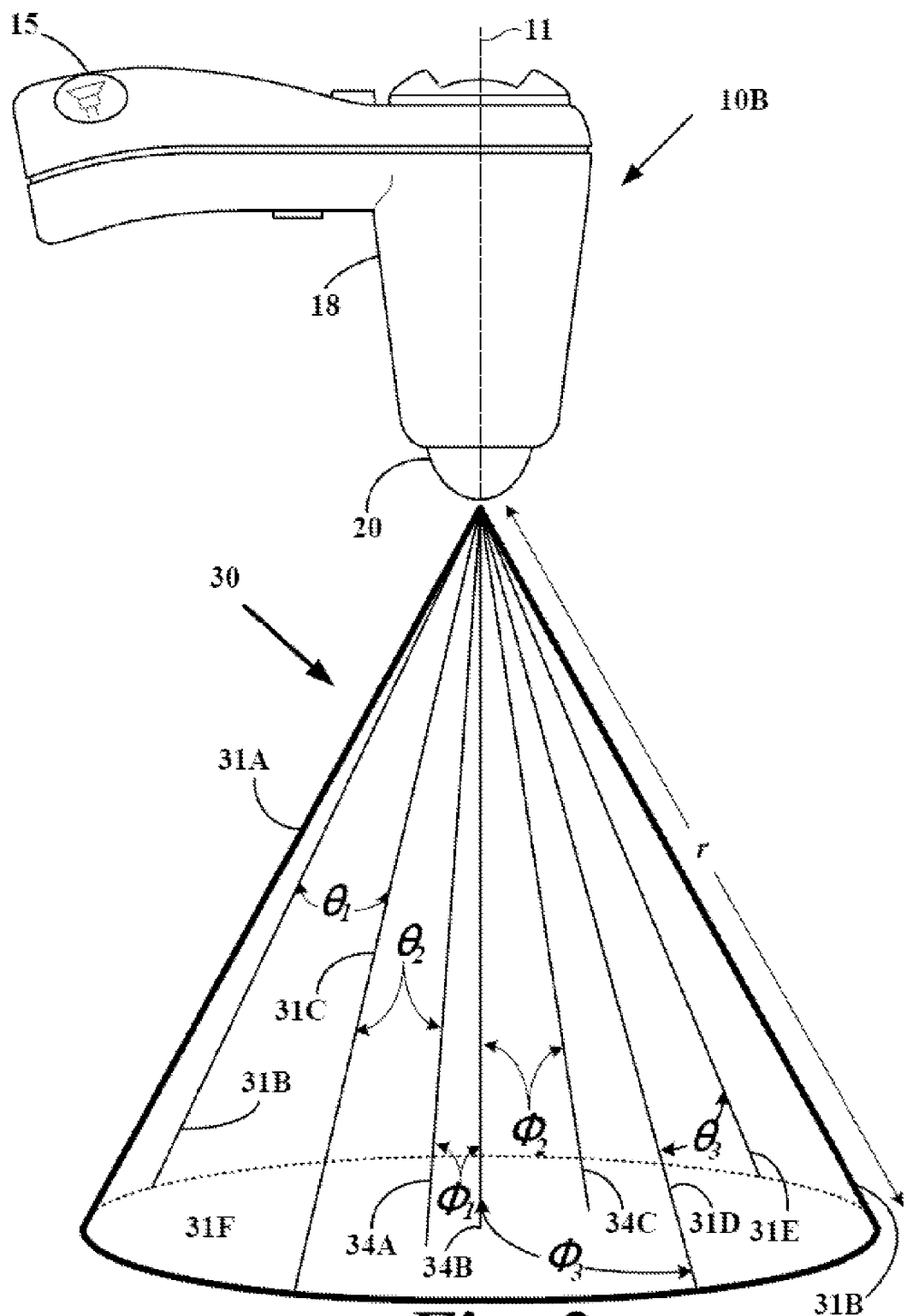
FIG. 2 depicts a partial schematic and partial isometric and side view of a transceiver, and a scan cone array comprised of 3D-distributed scan lines in alternate embodiment of an ultrasound harmonic imaging system.

FIG. 2 depicts a partial schematic and partial isometric and side view of a transceiver, and a scan cone array comprised of 3D-distributed scan lines in alternate embodiment of an ultrasound harmonic imaging system. A plurality of three-dimensional (3D) distributed scan lines emanating from a transceiver that cooperatively forms a scan cone 30. Each of the scan lines have a length r that projects outwardly from the transceivers 10A-10E of FIGS. 1A-1E. As illustrated the transceiver 10A emits 3D-distributed scan lines within the scan cone 30 that may be one-dimensional ultrasound A-lines. The other transceiver embodiments 10B-10E may also be configured to emit 3D-distributed scan lines. Taken as an aggregate, these 3D-distributed A-lines define the conical shape of the scan cone 30. The ultrasound scan cone 30 extends outwardly from the dome 20 of the transceiver 10A, 10B and 10C centered about an axis line 11. The 3D-distributed scan lines of the scan cone 30 include a plurality of internal and peripheral scan lines that may be distributed within a volume defined by a perimeter of the scan cone 30. Accordingly, the peripheral scan lines 31A-31F define an outer surface of the scan cone 30, while the internal scan lines 34A-34C may be distributed between the respective peripheral scan lines 31A-31F. Scan line 34B may be generally collinear with the axis 11, and the scan cone 30 may be generally and coaxially centered on the axis line 11.

The locations of the internal and peripheral scan lines may be further defined by an angular spacing from the center scan line 34B and between internal and peripheral scan lines. The angular spacing between scan line 34B and peripheral or internal scan lines may be designated by angle Φ and angular spacings between internal or peripheral scan lines may be designated by angle Ø. The angles $\Phi_1$, $\Phi_2$, and $\Phi_3$ respectively define the angular spacings from scan line 34B to scan lines 34A, 34C, and 31D. Similarly, angles $Ø_1$, $Ø_2$, and $Ø_3$ respectively define the angular spacings between scan line 31B and 31C, 31C and 34A, and 31D and 31E.

With continued reference to FIG. 2, the plurality of peripheral scan lines 31A-E and the plurality of internal scan lines 34A-D may be three dimensionally distributed A-lines (scan lines) that are not necessarily confined within a scan plane, but instead may sweep throughout the internal regions and along the periphery of the scan cone 30. Thus, a given point within the scan cone 30 may be identified by the coordinates r, Φ, and Ø whose values generally vary. The number and location of the internal scan lines emanating from the transceivers 10A-10E may thus be distributed within the scan cone 30 at different positional coordinates as required to sufficiently visualize structures or images within a region of interest (ROI) in a patient. The angular movement of the ultrasound transducer within the transceiver 10A-10E may be mechanically effected, and/or it may be electronically generated. In any case, the number of lines and the length of the lines may be uniform or otherwise vary, so that angle Φ sweeps through angles approximately between −60° between scan line 34B and 31A, and +60° between scan line 34B and 31B. Thus angle Φ in this example presents a total arc of approximately 120°. In one embodiment, the transceiver 10A, 10B and 10C may be configured to generate a plurality of 3D-distributed scan lines within the scan cone 30 having a length r of approximately 18 to 20 centimeters (cm).

Figure 3:
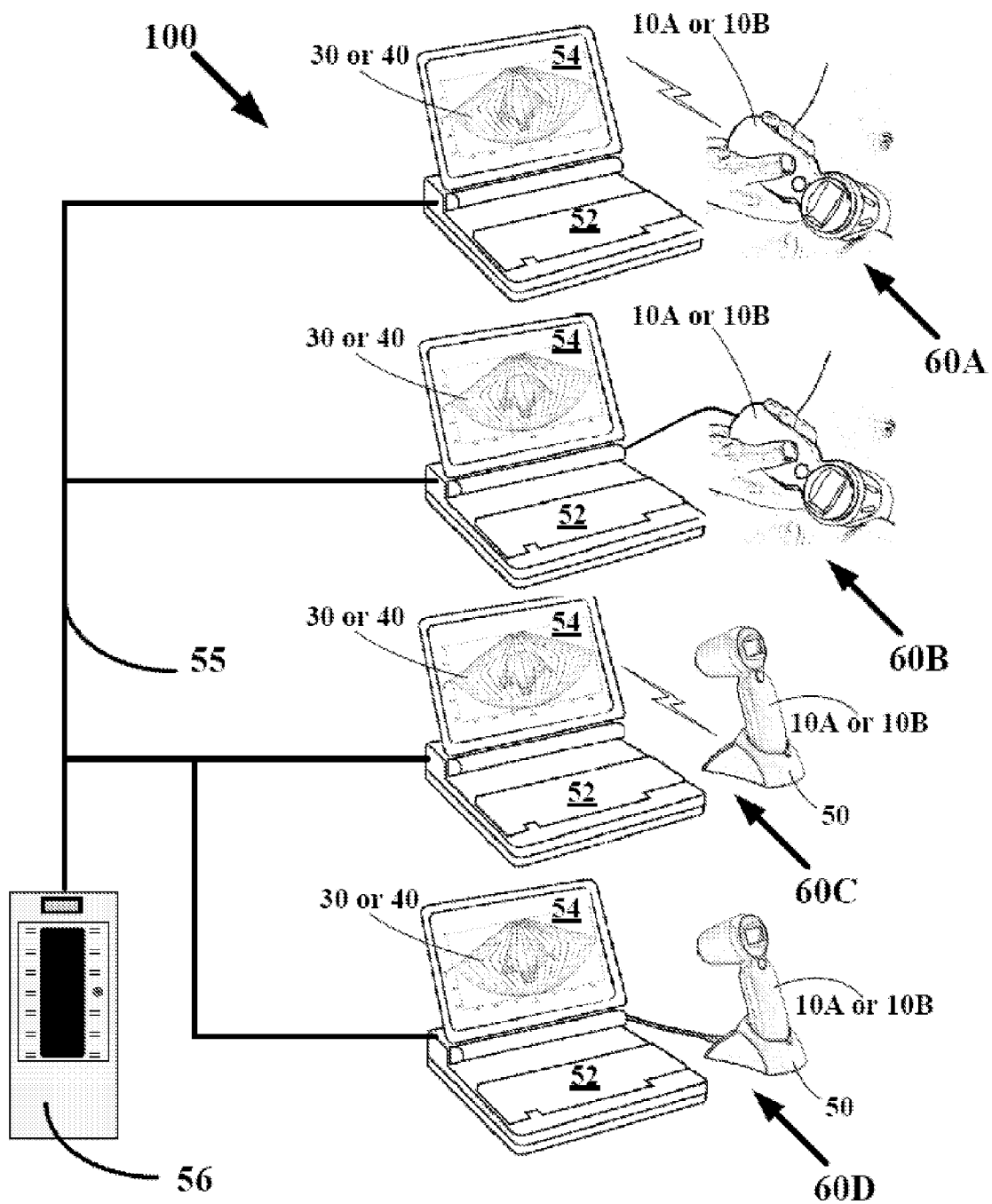
FIG. 3 is a schematic illustration of a server-accessed local area network in communication with a plurality of ultrasound harmonic imaging systems.

FIG. 3 is a schematic illustration of a server-accessed local area network in communication with a plurality of ultrasound harmonic imaging systems. An ultrasound harmonic imaging system 100 includes one or more personal computer devices 52 that may be coupled to a server 56 by a communications system 55. The devices 52 may be, in turn, coupled to one or more ultrasound transceivers 10A and/or 10B, for examples the ultrasound harmonic sub-systems 60A-60D. Ultrasound based images of organs or other regions of interest derived from either the signals of echoes from fundamental frequency ultrasound and/or harmonics thereof, may be shown within scan cone 30 or 40 presented on display 54. The server 56 may be operable to provide additional processing of ultrasound information, or it may be coupled to still other servers (not shown in FIG. 3) and devices. Transceivers 10A or 10B may be in wireless communication with computer 52 in sub-system 60A, in wired signal communication in sub-system 10B, in wireless communication with computer 52 via receiving cradle 50 in sub-system 10C, or in wired communication with computer 52 via receiving cradle 50 in sub-system 10D.

Figure 4:
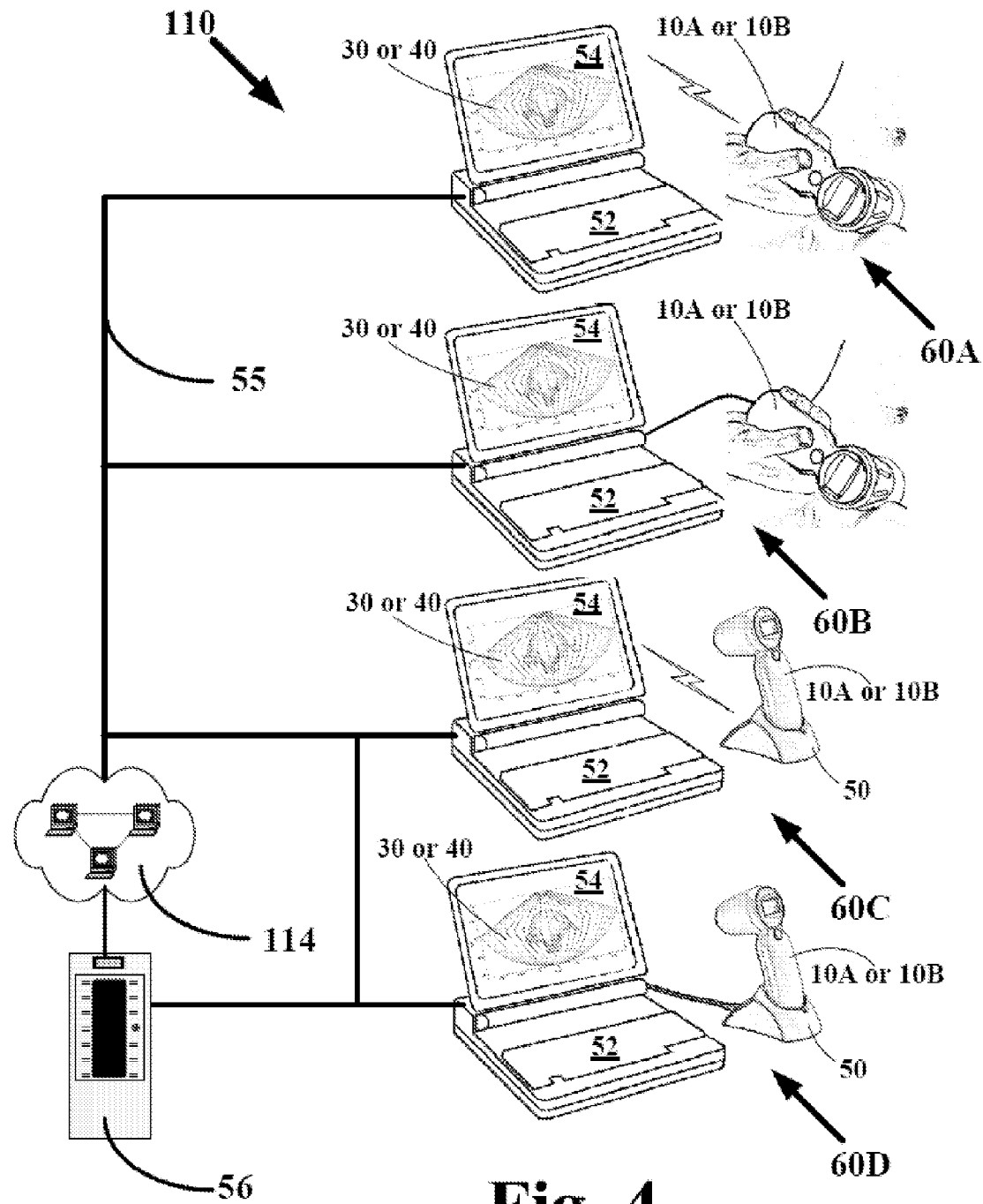
FIG. 4 is a schematic illustration of the Internet in communication with a plurality of ultrasound harmonic imaging systems.

FIG. 4 is a schematic illustration of the Internet in communication with a plurality of ultrasound harmonic imaging systems. An Internet system 110 may be coupled or otherwise in communication with the ultrasound harmonic sub-systems 60A-60D.

Figure 5:
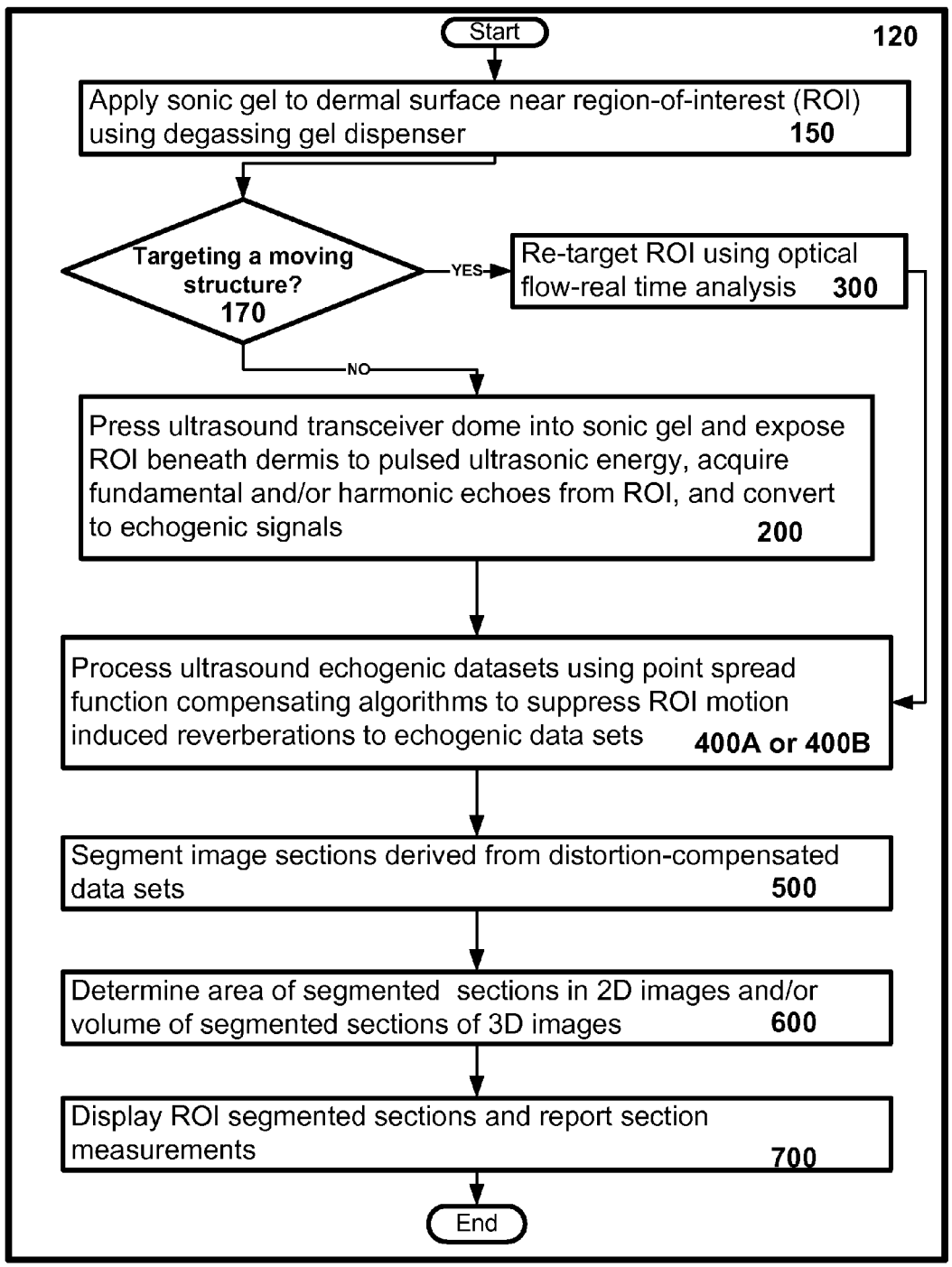
FIG. 5 schematically depicts a method flow chart algorithm 120 to acquire a clarity enhanced ultrasound image.

FIG. 5 schematically depicts a master method flow chart algorithm 120 to acquire a clarity enhanced ultrasound image. Algorithm 120 begins with process block 150, in which an acoustic coupling or sonic gel is applied to the dermal surface near the region-of-interest (ROI) using a degassing gel dispenser. Embodiments illustrating the degassing gel dispenser and its uses are depicted in FIGS. 36A-G below. After applying the sonic gel, decision diamond 170 is reached with the query "Targeting a moving structure?", and if negative to this query, algorithm 120 continues to process block 200. At process block 200, the ultrasound transceiver dome 20 of transceivers 10A,B are placed into the dermal residing sonic gel to and pulsed ultrasound energy is transmitted to the ROI. Thereafter, echoes of the fundamental ultrasound frequency and/or harmonics thereof are captured by the transceiver 10A,B and converted to echogenic signals. If the answer to decision diamond is affirmative for targeting a moving structure within the ROI, the ROI is re-targeted, at process block 300, using optical flow real-time analysis.

Whether receiving echogenic signals from non-moving targets within the ROI from processing block 200, or moving targets within the ROI from process block 300, algorithm 120 continues with processing blocks 400A or 400B. Processing blocks 400A and 400B process echogenic datasets of the echogenic signals from process blocks 200 and 300 using a point spread function algorithms to compensate or otherwise suppress motion induced reverberations within the ROI echogenic data sets. Processing block 400A employs non-parametric analysis, and processing block 400B employs parametric analysis and described in FIG. 9 below. Once motion artifacts are corrected, algorithm 120 continues with processing block 50 to segment image sections derived from the distortion-compensated data sets. At process block 600, areas of the segmented sections within 2D images and/or 3D volumes are determined. Thereafter, master algorithm 120 completes at process block 700 in which segmented structures within the static or moving ROI is displayed along with any segmented section area and/or volume measurements.

Figure 6:
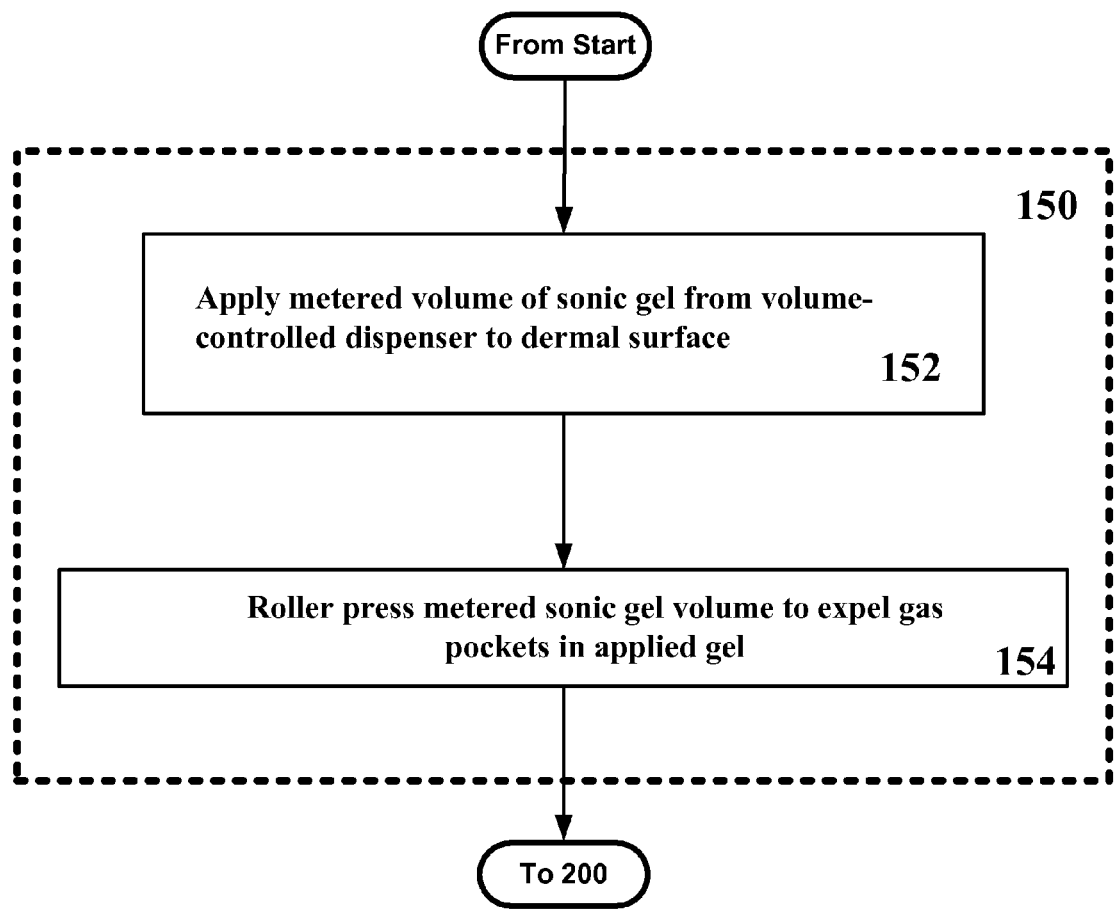
FIG. 6 is an expansion of sub-algorithm 150 of master algorithm 120 of FIG. 7.
Figure 7:
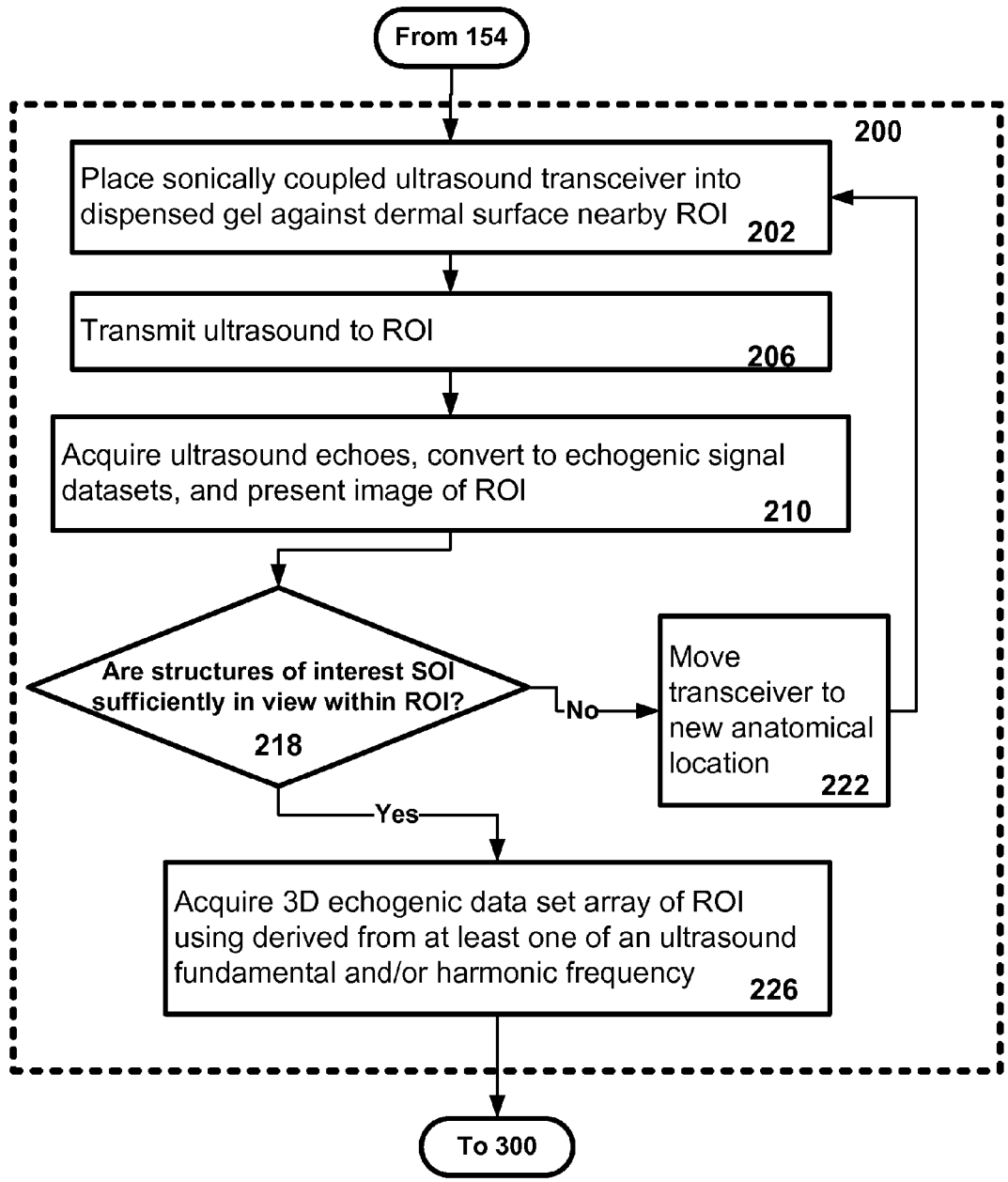
FIG. 7 is an expansion of sub-algorithms 200 of FIG. 5.

FIG. 6 is an expansion of sub-algorithm 150 of master algorithm 120 of FIG. 7. Beginning from the entry point of master algorithm 120, sub-algorithm 150 starts at process block 152 wherein a metered volume of sonic gel is applied from the volume-controlled dispenser to the dermal surface believed to overlap the ROI. Thereafter, at process block 154, any gas pockets within the applied gel are expelled by a roller pressing action. Sub-algorithm 150 is then completed and exits to sub-algorithm 200.

FIG. 7 is an expansion of sub-algorithms 200 of FIG. 5. Entering from process block 154, sub-algorithm 200 starts at process block 202 wherein the transceiver dome 20 of transceivers 10A,B are placed into the gas-purged sonic gel to get a firm sonic coupling, and then at process block 206, pulsed frequency ultrasound is transmitted to the underlying ROI. Thereafter, at process block 210, ultrasound echoes from the ROI and any intervening structure, is collected by the transceivers 10A,B and converted to the echogenic data sets for presentation of an image of the ROI. Once the image of the ROI is displayed, decision diamond 218 is reached with the query "Are structures of interest SOI sufficiently in view within ROI?", and if negative to this query, sub-algorithm 200 continues to process block 222 in which the transceiver is moved to a new anatomical location for re-routing to process block 202. At process block 200, the ultrasound transceiver dome 20 of transceivers 10A,B are placed into the dermal residing sonic gel to and pulsed ultrasound energy is transmitted to the ROI. If the answer to the decision diamond 218 is affirmative for a sufficiently viewed SOI, sub-algorithm 200 continues to process block 226 in which a 3D echogenic data set array of the ROI is acquired using at least one of an ultrasound fundamental and/or harmonic frequency. Sub-algorithm 200 is then completed and exits to sub-algorithm 300.

Figure 8:
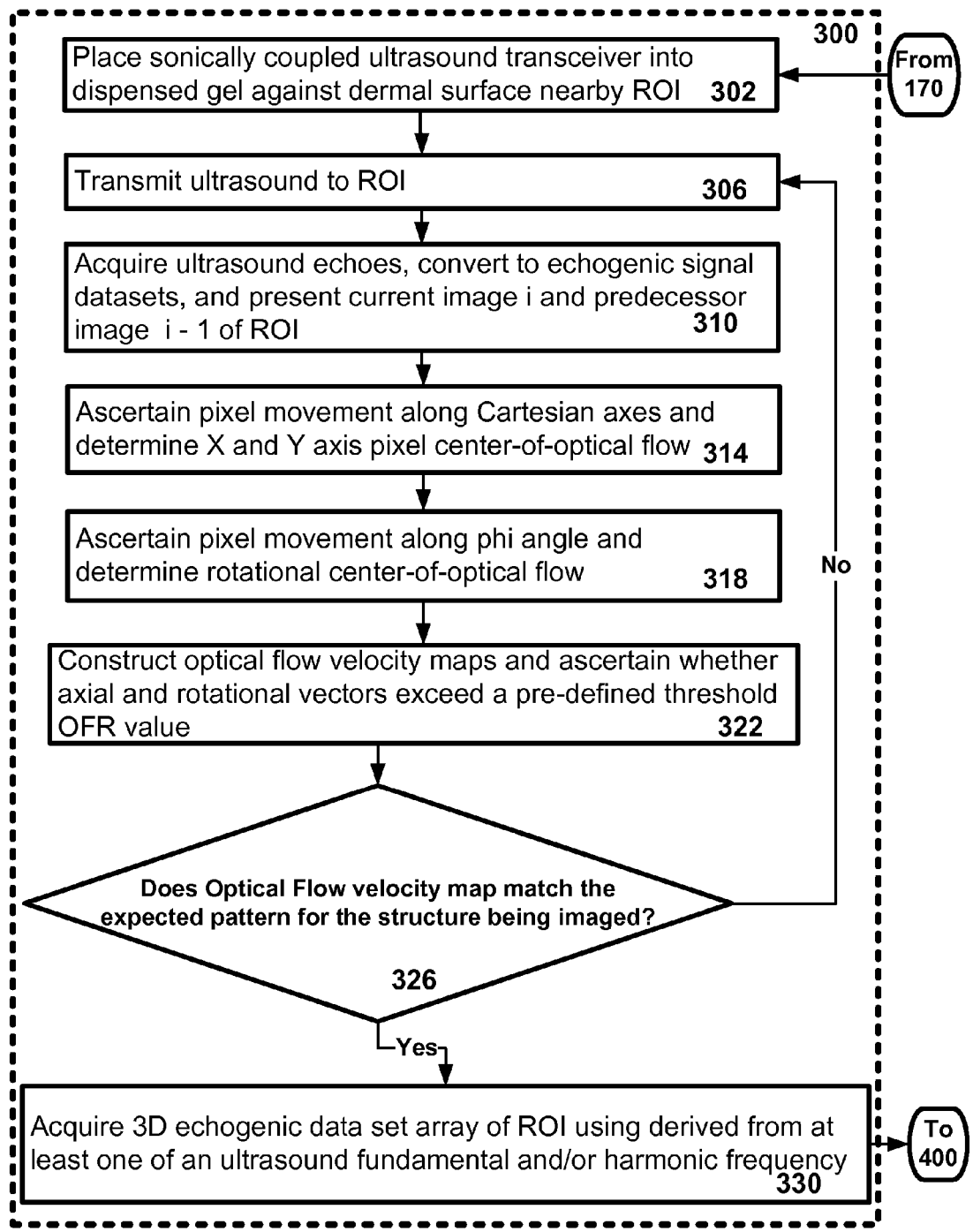
FIG. 8 is an expansion of sub-algorithm 300 of master algorithm illustrated in FIG. 5.

FIG. 8 is an expansion of sub-algorithm 300 of master algorithm illustrated in FIG. 5. Entering from process block 170, sub-algorithm 300 begins in processing block 302 by making a transceiver 10A,B-to-ROI sonic coupling similar to process block 202, transmitting pulse frequency ultrasound at process block 306, and thereafter, at processing block 310, acquire ultrasound echoes, convert to echogenic data sets, and present a currently displayed image "i" of the ROI and compare "i" with any predecessor image "i−1" of the ROI, if available. Thereafter, at process block 314, pixel movement along Cartesian axes is ascertained to determine X and Y-axis pixel center-of-optical flow, and similarly, followed by process block 318 pixel movement along the phi angle to ascertain a rotational center-of-optical flow. Thereafter, at process block 322, optical flow velocity maps to ascertain whether axial and rotational vectors exceed a pre-defined threshold OFR value. Once the velocity maps are obtained, decision diamond 326 is reached with the query "Does optical flow velocity map match the expected pattern for the structure being imaged?", and if negative, sub-algorithm re-routes to process block 306 for retransmission of ultrasound to the ROI via the sonically coupled transceiver 10A,B. If affirmative for a matched velocity map and expected pattern of the structure being imaged, sub-algorithm 300 continues with process block 330 in which a 3D echogenic data set array of the ROI is acquired using at least one of an ultrasound fundamental and/or harmonic frequency. Sub-algorithm 300 is then completed and exits to sub-algorithms 400A and 400B.

Figure 9:
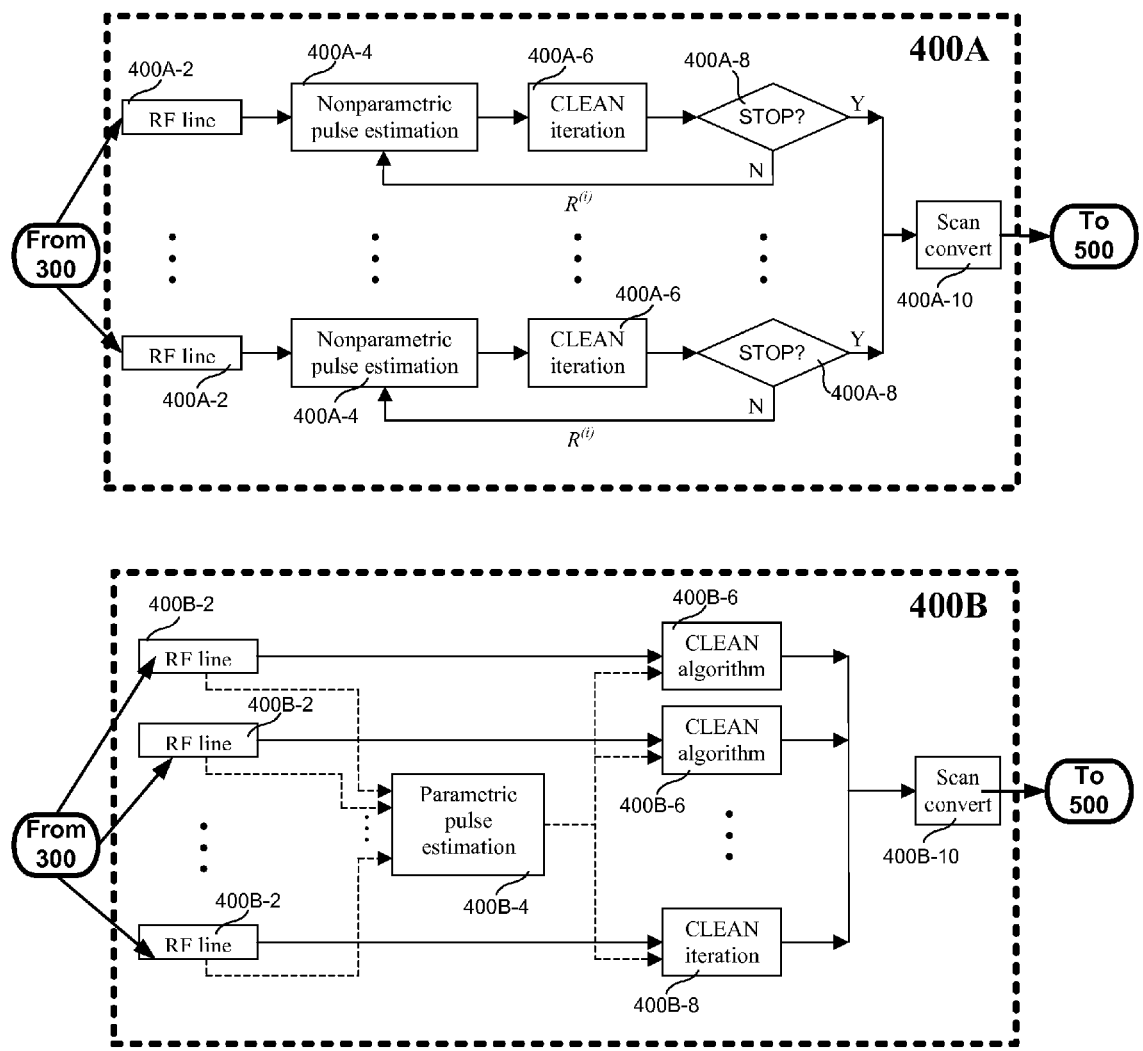
FIG. 9 is an expansion of sub-algorithms 400A and 400B of FIG. 5.

FIG. 9 depicts expansion of subalgorithms 400A and 400B of FIG. 5. Sub-algorithm 400A employs nonparametric pulse estimation and 400B employs parametric pulse estimation. Sub-algorithm 400A describes an implementation of the CLEAN algorithm for reducing reverberation and noise in the ultrasound signals and comprises an RF line processing block 400A-2, a non-parametric pulse estimation block 400A-4, a CLEAN iteration block 400A-6, a decision diamond block 400A-8 having the query "STOP?", and a Scan Convert processing block 400A-10. The same algorithm is applied to each RF line in a scan plane, but each RF line uses its own unique estimate of the point spread function of the transducer (or pulse estimate). The algorithm is iterative by re-routing to Non parametric pulse estimation block 400A-4 in that the point spread function is estimated, the CLEAN sub-algorithm applied and then the pulse is re-estimated from the output of the CLEAN sub-algorithm. The iterations are stopped after a maximum number of iterations is reached or the changes in the signal are sufficiently small. Thereafter, once the iteration has stopped, the signals are converted for presentation as part of a scan plane image at process block 400A-10. Sub-algorithm 400A is then completed and exits to sub-algorithms 500.

Referring to sub-algorithm 400B, parametric analysis employs an implementation of the CLEAN algorithm that is not iterative. Sub-algorithm 400B comprise comprises an RF line processing block 400B-2, a parametric pulse estimation block 400B-4, a CLEAN algorithm block 400B-6, a CLEAN iteration block 400B-8, and a Scan Convert processing block 400B-10. The point spread function of the transducer is estimated once and becomes a priori information used in the CLEAN algorithm. A single estimate of the pulse is applied to all RF lines in a scan plane and the CLEAN algorithm is applied once to each line. The signal output is then converted for presentation as part of a scan plane image at process block 400B-10. Sub-algorithm 400B is then completed and exits to sub-algorithms 500.

Figure 10:
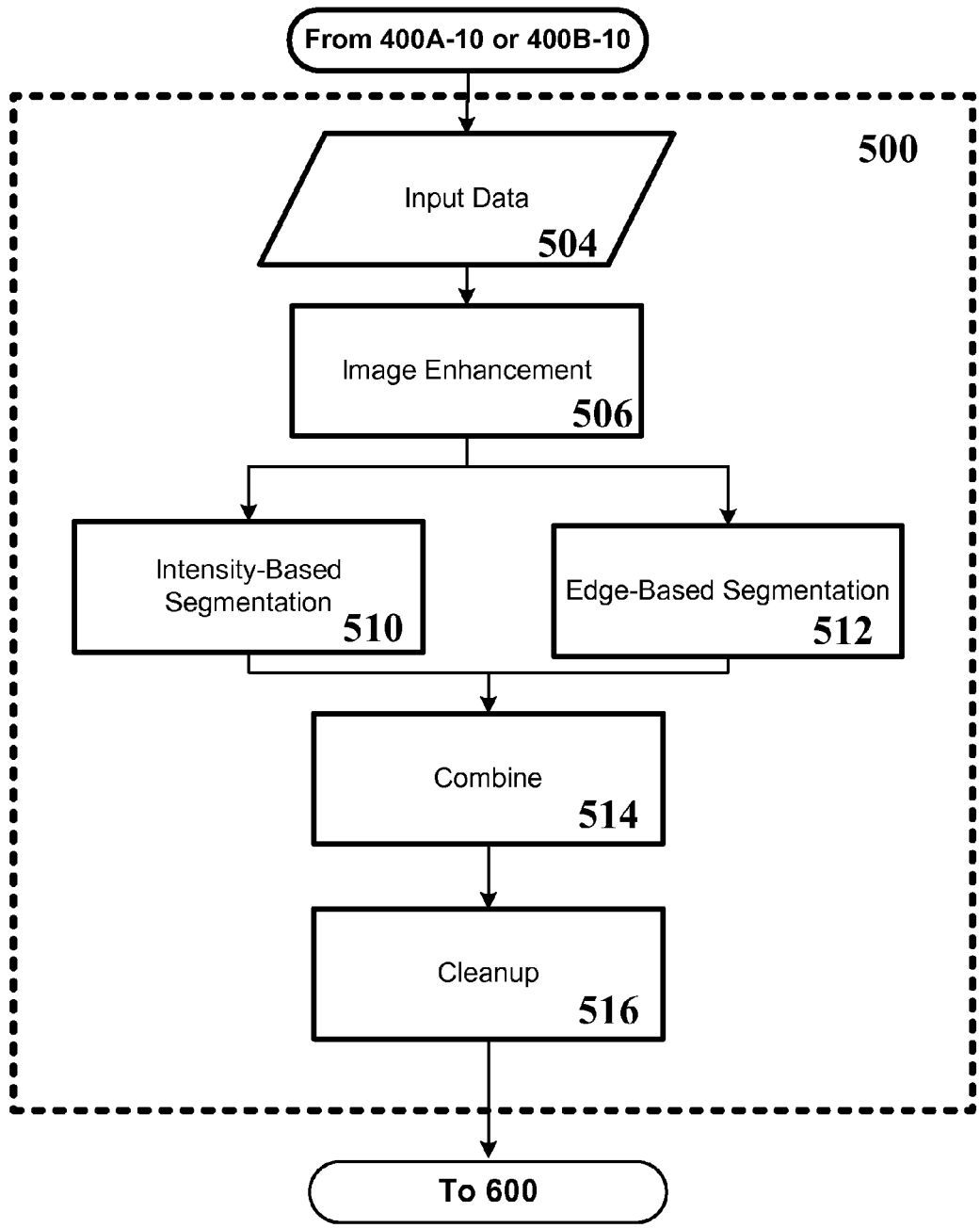
FIG. 10 is an expansion of sub-algorithm 500 of FIG. 5.

FIG. 10 is an expansion of sub-algorithm 500 of FIG. 5. 3D data sets from processing blocks 400A-10 or 400B-10 of sub-algorithms 400A or 400B are entered at input data process block 504 that then undergoes a 2-step image enhancement procedure at process block 506. The 2-step image enhancement includes performing a heat filter to reduce noise followed by a shock filter to sharpen edges of structures within the 3D data sets. The heat and shock filters are partial differential equations (PDE) defined respectively in Equations E1 and E2 below:

$E1:$ $$\frac{\partial u}{\partial t} = \frac{\partial^2 u}{\partial x^2} + \frac{\partial^2 u}{\partial y^2} \text{ (Heat Filter)}$$

$E2:$ $$\frac{\partial u}{\partial t} = -F(l(u))\|\nabla u\| \text{ (Shock Filter)}$$

Here u in the heat filter represents the image being processed. The image u is 2D, and is comprised of an array of pixels arranged in rows along the x-axis, and an array of pixels arranged in columns along the y-axis. The pixel intensity of each pixel in the image u has an initial input image pixel intensity (I) defined as $u_0$=I. The value of I depends on the application, and commonly occurs within ranges consistent with the application. For example, I can be as low as 0 to 1, or occupy middle ranges between 0 to 127 or 0 to 512. Similarly, I may have values occupying higher ranges of 0 to 1024 and 0 to 4096, or greater. For the shock filter u represents the image being processed whose initial value is the input image pixel intensity (I): $u_0$=I where the l(u) term is the Laplacian of the image u, F is a function of the Laplacian, and $\|\nabla u\|$ is the 2D gradient magnitude of image intensity defined by equation E3:

$$\|\nabla u\| = \sqrt{u_x^2 + u_y^2} \qquad E3$$

Where $u_x^2$=the square of the partial derivative of the pixel intensity (u) along the x-axis, $u_y^2$=the square of the partial derivative of the pixel intensity (u) along the y-axis, the Laplacian l(u) of the image, u, is expressed in equation E4:

$$l(u) = u_{xx}u_x^2 + 2u_{xy}u_xu_y + u_{yy}u_y^2 \qquad E4$$

Equation E9 relates to equation E6 as follows:

Ux is the first partial derivative $$\frac{\partial u}{\partial x}$$

of u along the x-axis,

Ux Uy is the first partial derivative $$\frac{\partial u}{\partial y}$$

of u along the y-axis,

Ux $U_x^2$ is the square of the first partial derivative $$\frac{\partial u}{\partial x}$$

of u along the x-axis,

Ux $U_y^2$ is the square of the first partial derivative $$\frac{\partial u}{\partial y}$$

of u along the y-axis,

Ux Uxx is the second partial derivative $$\frac{\partial^2 u}{\partial x^2}$$

of u along the x-axis,

Ux Uyy is the second partial derivative $$\frac{\partial^2 u}{\partial y^2}$$

of u along the y-axis,
Uxy is cross multiple first partial derivative $$\frac{\partial u}{\partial x \partial y}$$

of u along the x and y axes, and
Uxy the sign of the function F modifies the Laplacian by the image gradient values selected to avoid placing spurious edges at points with small gradient values:

$$F(l(u)) = 1, \quad \text{if } l(u) > 0 \text{ and } \|\nabla u\| > t$$
$$= -1, \quad \text{if } l(u) < 0 \text{ and } \|\nabla u\| > t$$
$$= 0, \text{ otherwise}$$

where t is a threshold on the pixel gradient value $\|\nabla u\|$.

The combination of heat filtering and shock filtering produces an enhanced image ready to undergo the intensity-based and edge-based segmentation algorithms as discussed below. The enhanced 3D data sets are then subjected to a parallel process of intensity-based segmentation at process block 510 and edge-based segmentation at process block 512. The intensity-based segmentation step uses a "k-means" intensity clustering technique where the enhanced image is subjected to a categorizing "k-means" clustering algorithm. The "k-means" algorithm categorizes pixel intensities into white, gray, and black pixel groups. Given the number of desired clusters or groups of intensities (k), the k-means algorithm is an iterative algorithm comprising four steps: Initially determine or categorize cluster boundaries by defining a minimum and a maximum pixel intensity value for every white, gray, or black pixels into groups or k-clusters that are equally spaced in the entire intensity range. Assign each pixel to one of the white, gray or black k-clusters based on the currently set cluster boundaries. Calculate a mean intensity for each pixel intensity k-cluster or group based on the current assignment of pixels into the different k-clusters. The calculated mean intensity is defined as a cluster center. Thereafter, new cluster boundaries are determined as mid points between cluster centers. The fourth and final step of intensity-based segmentation determines if the cluster boundaries significantly change locations from their previous values. Should the cluster boundaries change significantly from their previous values, iterate back to step 2, until the cluster centers do not change significantly between iterations. Visually, the clustering process is manifest by the segmented image and repeated iterations continue until the segmented image does not change between the iterations.

The pixels in the cluster having the lowest intensity value—the darkest cluster—are defined as pixels associated with internal cavity regions of bladders. For the 2D algorithm, each image is clustered independently of the neighboring images. For the 3D algorithm, the entire volume is clustered together. To make this step faster, pixels are sampled at 2 or any multiple sampling rate factors before determining the cluster boundaries. The cluster boundaries determined from the down-sampled data are then applied to the entire data.

The edge-based segmentation process block 512 uses a sequence of four sub-algorithms. The sequence includes a spatial gradients algorithm, a hysteresis threshold algorithm, a Region-of-Interest (ROI) algorithm, and a matching edges filter algorithm. The spatial gradient algorithm computes the x-directional and y-directional spatial gradients of the enhanced image. The hysteresis threshold algorithm detects salient edges. Once the edges are detected, the regions defined by the edges are selected by a user employing the ROI algorithm to select regions-of-interest deemed relevant for analysis.

Since the enhanced image has very sharp transitions, the edge points can be easily determined by taking x- and y-derivatives using backward differences along x- and y-directions. The pixel gradient magnitude $\|\nabla I\|$ is then computed from the x- and y-derivative image in equation E5 as:

$$\|\nabla I\| = \sqrt{I_x^2 + I_y^2} \qquad E5$$

Where $I_x^2$=the square of x-derivative of intensity and $I_y^2$=the square of y-derivative of intensity along the y-axis.

Significant edge points are then determined by thresholding the gradient magnitudes using a hysteresis thresholding operation. Other thresholding methods could also be used. In hysteresis thresholding, two threshold values, a lower threshold and a higher threshold, are used. First, the image is thresholded at the lower threshold value and a connected component labeling is carried out on the resulting image. Next, each connected edge component is preserved which has at least one edge pixel having a gradient magnitude greater than the upper threshold. This kind of thresholding scheme is good at retaining long connected edges that have one or more high gradient points.

In the preferred embodiment, the two thresholds are automatically estimated. The upper gradient threshold is estimated at a value such that at most 97% of the image pixels are marked as non-edges. The lower threshold is set at 50% of the value of the upper threshold. These percentages could be different in different implementations. Next, edge points that lie within a desired region-of-interest are selected. This region of interest algorithm excludes points lying at the image boundaries and points lying too close to or too far from the transceivers 10A,B. Finally, the matching edge filter is applied to remove outlier edge points and fill in the area between the matching edge points.

The edge-matching algorithm is applied to establish valid boundary edges and remove spurious edges while filling the regions between boundary edges. Edge points on an image have a directional component indicating the direction of the gradient. Pixels in scanlines crossing a boundary edge location can exhibit two gradient transitions depending on the pixel intensity directionality. Each gradient transition is given a positive or negative value depending on the pixel intensity directionality. For example, if the scanline approaches an echo reflective bright wall from a darker region, then an ascending transition is established as the pixel intensity gradient increases to a maximum value, i.e., as the transition ascends from a dark region to a bright region. The ascending transition is given a positive numerical value. Similarly, as the scanline recedes from the echo reflective wall, a descending transition is established as the pixel intensity gradient decreases to or approaches a minimum value. The descending transition is given a negative numerical value.

Valid boundary edges are those that exhibit ascending and descending pixel intensity gradients, or equivalently, exhibit paired or matched positive and negative numerical values.

The valid boundary edges are retained in the image. Spurious or invalid boundary edges do not exhibit paired ascending-descending pixel intensity gradients, i.e., do not exhibit paired or matched positive and negative numerical values. The spurious boundary edges are removed from the image.

For bladder cavity volumes, most edge points for blood fluid surround a dark, closed region, with directions pointing inwards towards the center of the region. Thus, for a convex-shaped region, the direction of a gradient for any edge point, the edge point having a gradient direction approximately opposite to the current point represents the matching edge point. Those edge points exhibiting an assigned positive and negative value are kept as valid edge points on the image because the negative value is paired with its positive value counterpart. Similarly, those edge point candidates having unmatched values, i.e., those edge point candidates not having a negative-positive value pair, are deemed not to be true or valid edge points and are discarded from the image.

The matching edge point algorithm delineates edge points not lying on the boundary for removal from the desired dark regions. Thereafter, the region between any two matching edge points is filled in with non-zero pixels to establish edge-based segmentation. In a preferred embodiment of the invention, only edge points whose directions are primarily oriented co-linearly with the scanline are sought to permit the detection of matching front wall and back wall pairs of a bladder cavity, for example the left or right ventricle.

Referring again to FIG. 10, results from the respective segmentation procedures are then combined at process block 514 and subsequently undergoes a cleanup algorithm process at process block 516. The combining process of block 214 uses a pixel-wise Boolean AND operator step to produce a segmented image by computing the pixel intersection of two images. The Boolean AND operation represents the pixels of each scan plane of the 3D data sets as binary numbers and the corresponding assignment of an assigned intersection value as a binary number 1 or 0 by the combination of any two pixels. For example, consider any two pixels, say $pixel_A$ and $pixel_B$, which can have a 1 or 0 as assigned values. If $pixel_A$'s value is 1, and $pixel_B$'s value is 1, the assigned intersection value of $pixel_A$ and $pixel_B$ is 1. If the binary value of $pixel_A$ and $pixel_B$ are both 0, or if either $pixel_A$ or $pixel_B$ is 0, then the assigned intersection value of $pixel_A$ and $pixel_B$ is 0. The Boolean AND operation takes the binary any two digital images as input, and outputs a third image with the pixel values made equivalent to the intersection of the two input images.

After combining the segmentation results, the combined pixel information in the 3D data sets In a fifth process is cleaned at process block 516 to make the output image smooth and to remove extraneous structures not relevant to bladder cavities. Cleanup 516 includes filling gaps with pixels and removing pixel groups unlikely to be related to the ROI undergoing study, for example pixel groups unrelated to bladder cavity structures. Sub-algorithm 500 is then completed and exits to sub-algorithm 600.

Figure 11:
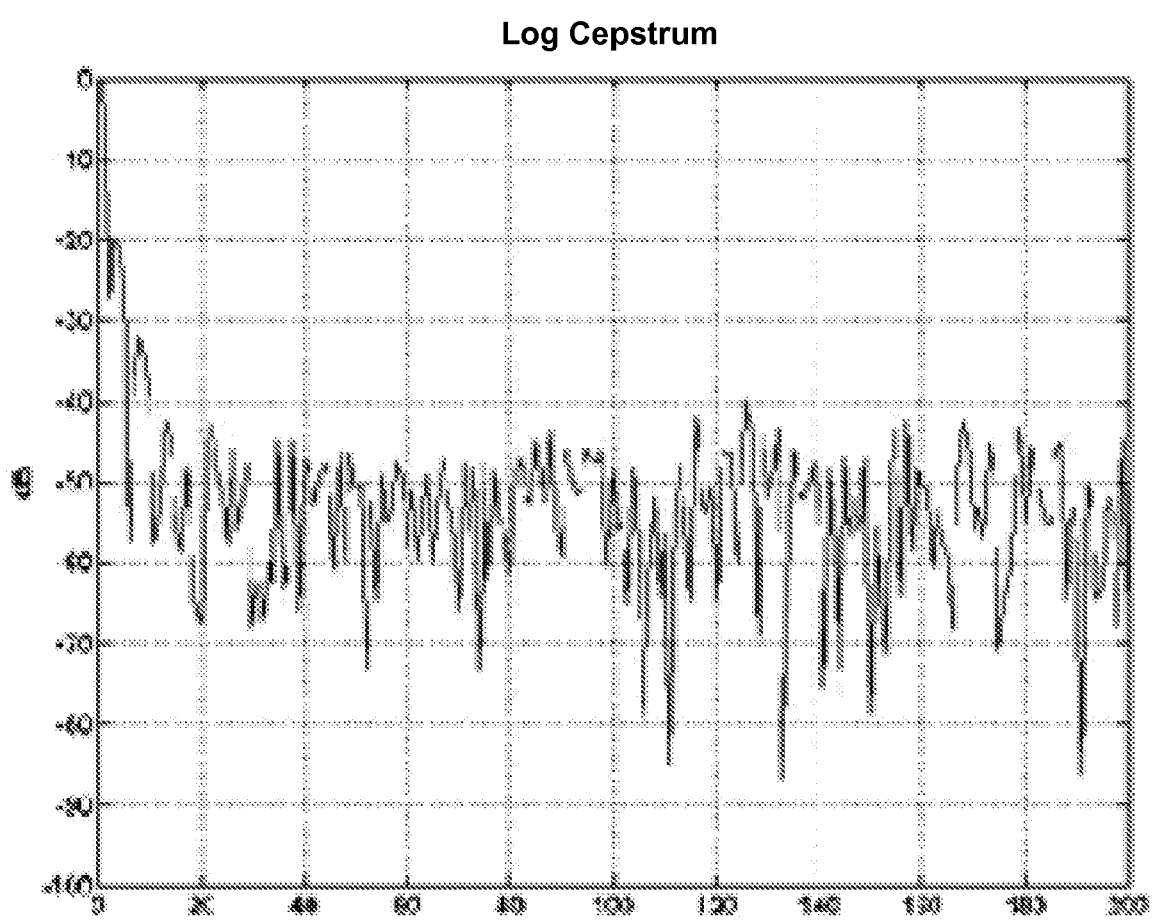
FIG. 11 depicts a logarithm of a Cepstrum.

FIG. 11 depicts a logarithm of a Cepstrum. The Cepstrum is used in sub-algorithm 400A for the pulse estimation via application of point spread functions to the echogenic data sets generated by the transceivers 10A,B.

FIGS. 12A-C depict histogram waveform plots derived from water tank pulse-echo experiments undergoing parametric and non-parametric analysis. FIG. 12A is a measure plot. FIG. 12B is a nonparametric pulse estimated pattern derived from sub-algorithm 400A. FIG. 12c is a parametric pulse estimated pattern derived from sub-algorithm 400B.

FIGS. 13-25 are bladder sonograms that depict image clarity after undergoing image enhancement processing by algorithms described in FIGS. 5-10.

Figure 13:
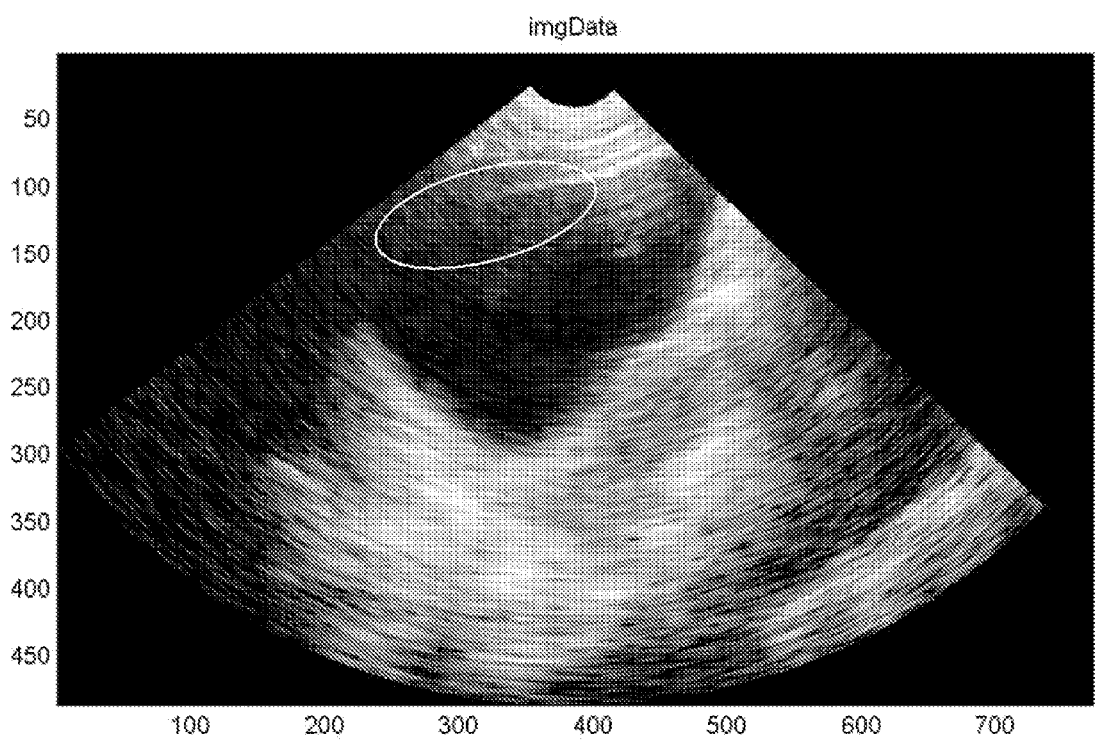
FIGS. 13-25 are bladder sonograms that depict image clarity after undergoing image enhancement processing by algorithms described in FIGS. 5-10.

FIG. 13 is an unprocessed image that will undergo image enhancement processing.

Figure 14:
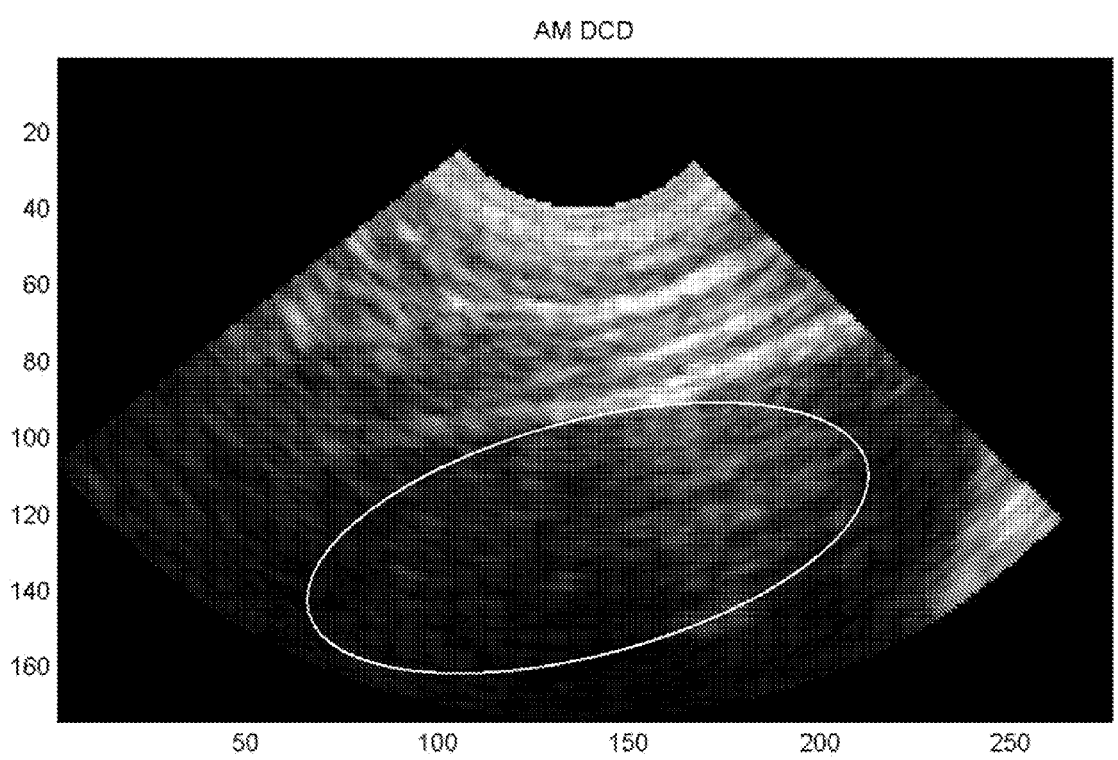

FIG. 14 illustrates an enclosed portion of a magnified region of FIG. 13.

Figure 15:
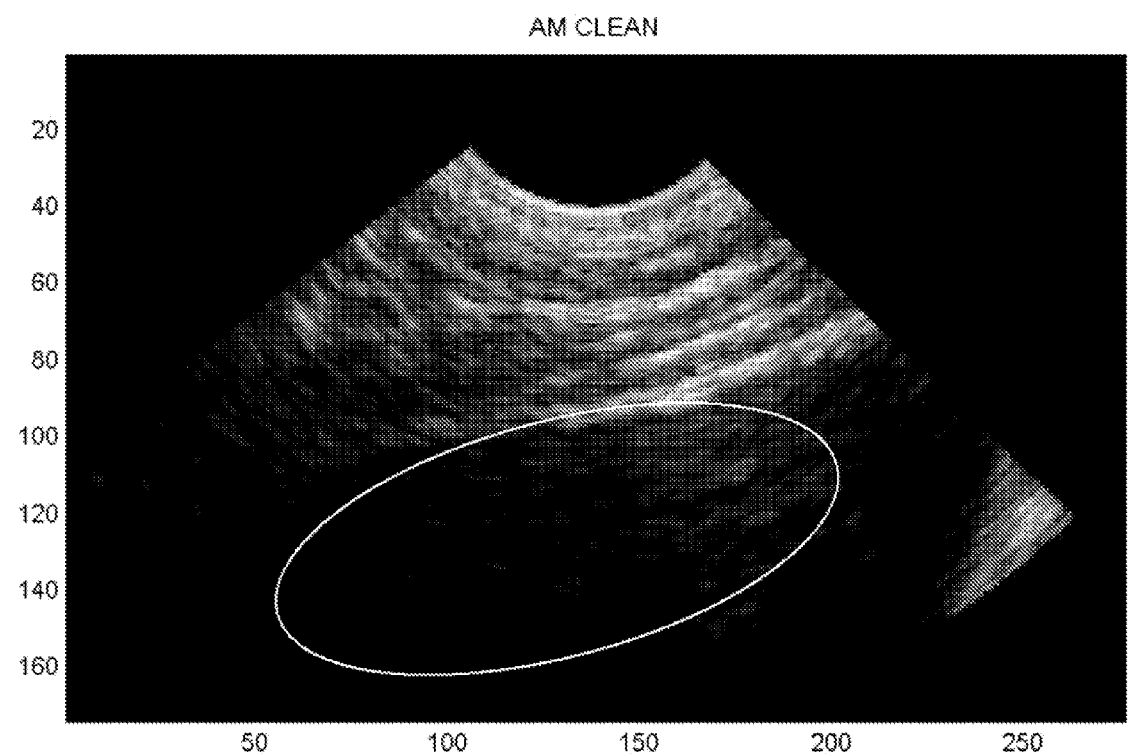

FIG. 15 is the resultant image of FIG. 13 that has undergone image processing via nonparametric estimation under sub-algorithm 400A. The low echogenic region within the circle inset has more contrast than the unprocessed image of FIGS. 13 and 14.

Figure 16:
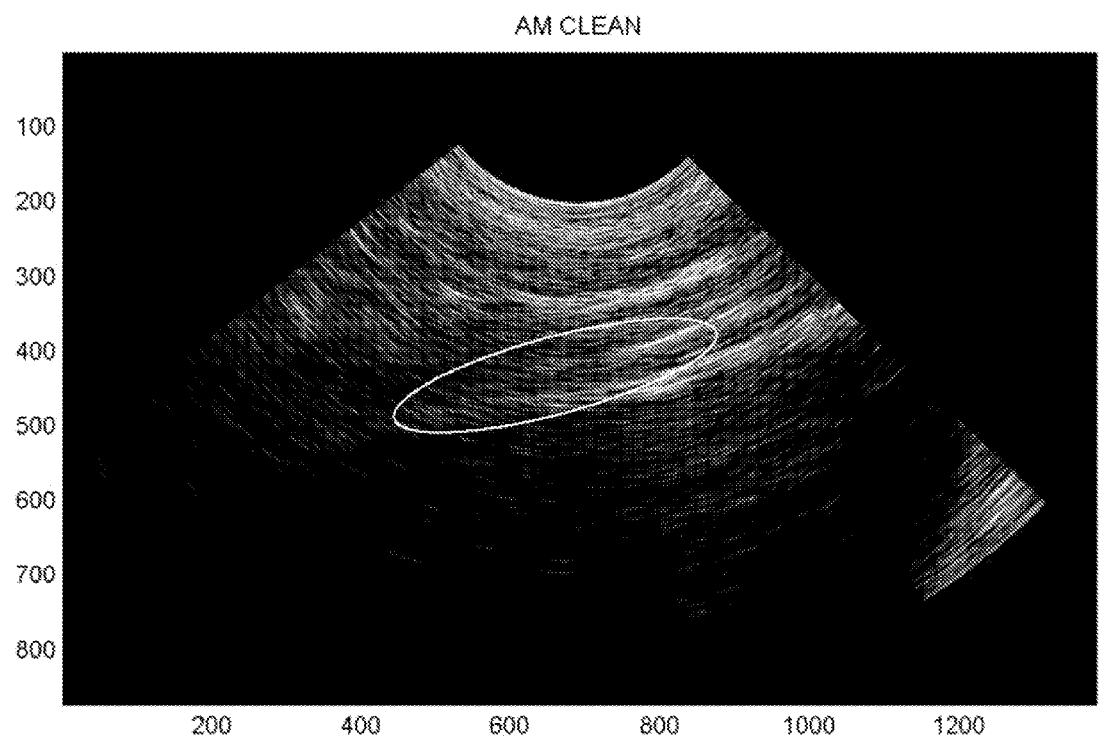

FIG. 16 is the resultant image of FIG. 13 that has undergone image processing via parametric estimation under sub-algorithm 400B. Here the circle inset is in the echogenic musculature region encircling the bladder and is shown with enhanced contrast and clarity than the magnified, unprocessed image of FIG. 14.

Figure 17:
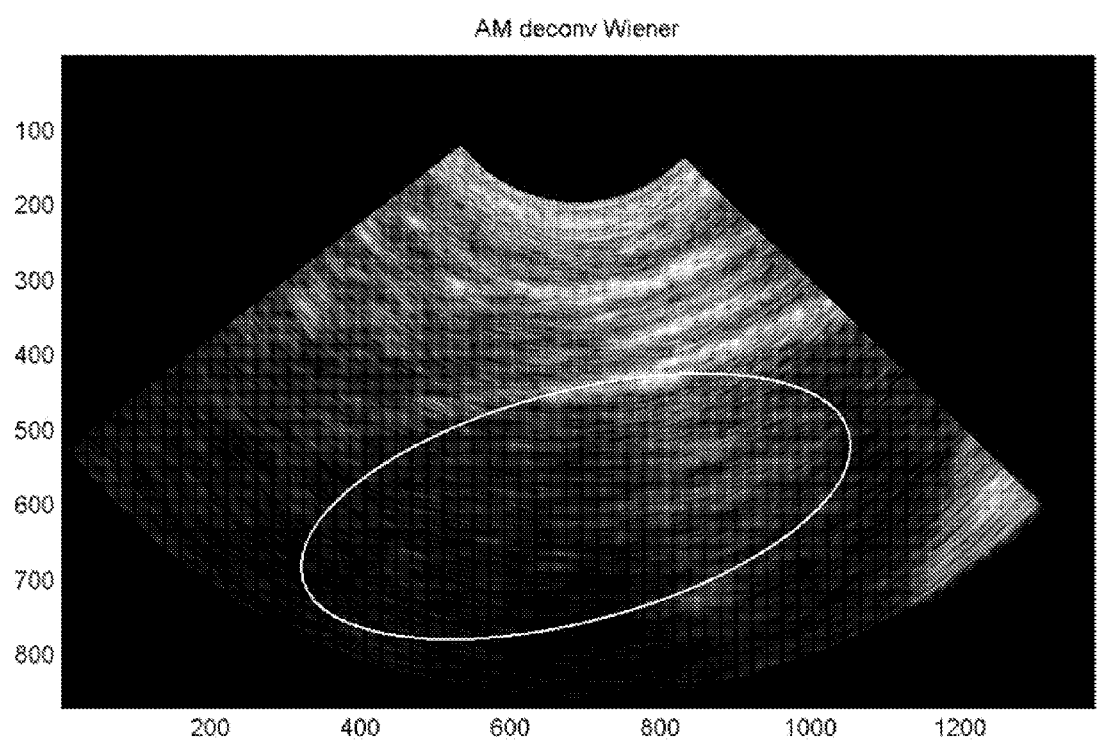

FIG. 17 the resultant image of an alternate image-processing embodiment using a Weiner filter. Weiner filtration image does not have the clarity nor the contrast in the low echogenic bladder region of FIG. 15 (compare circle insets).

Figure 18:
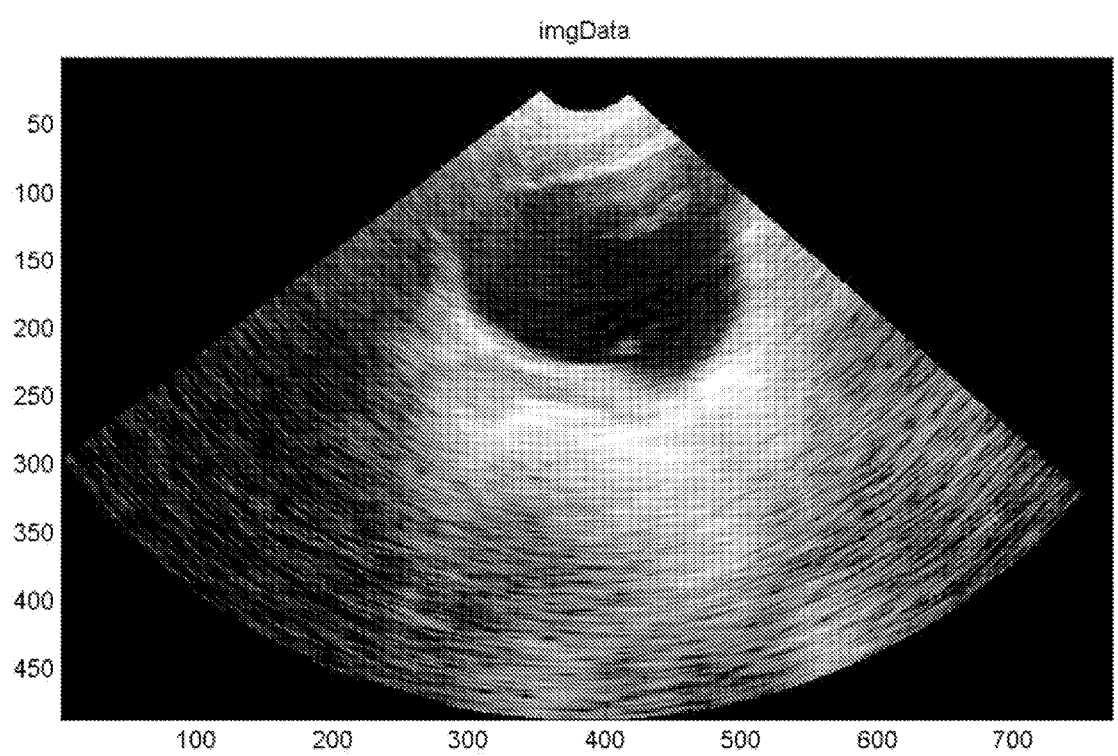

FIG. 18 is another unprocessed image that will undergo image enhancement processing.

Figure 19:
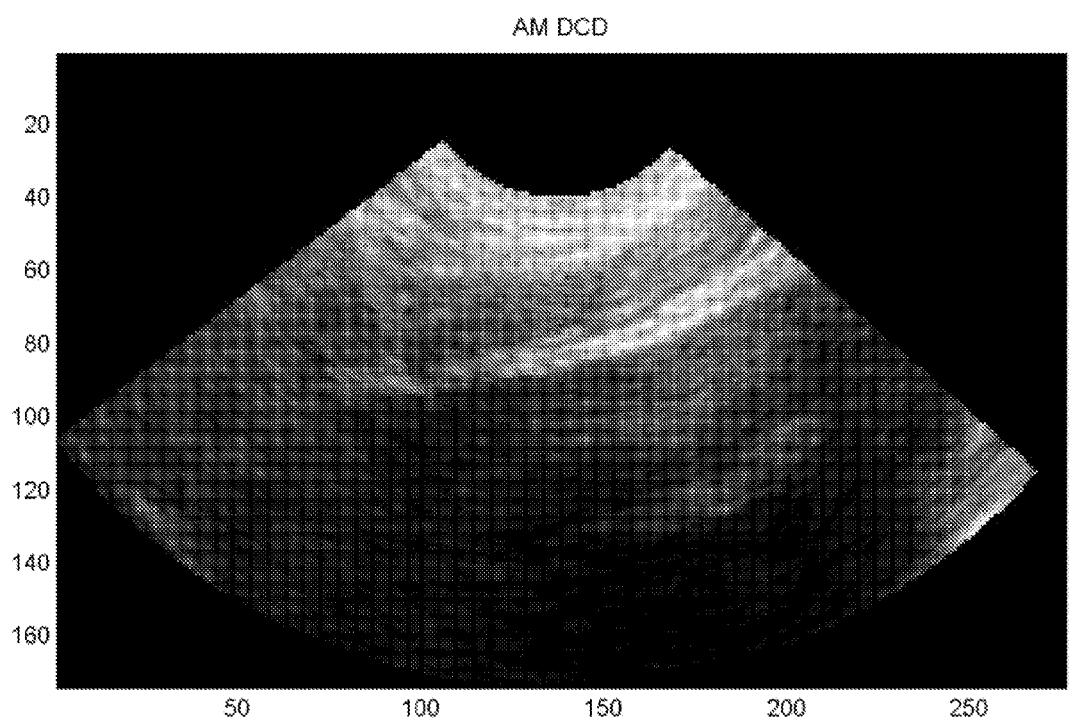

FIG. 19 illustrates an enclosed portion of a magnified region of FIG. 18.

Figure 20:
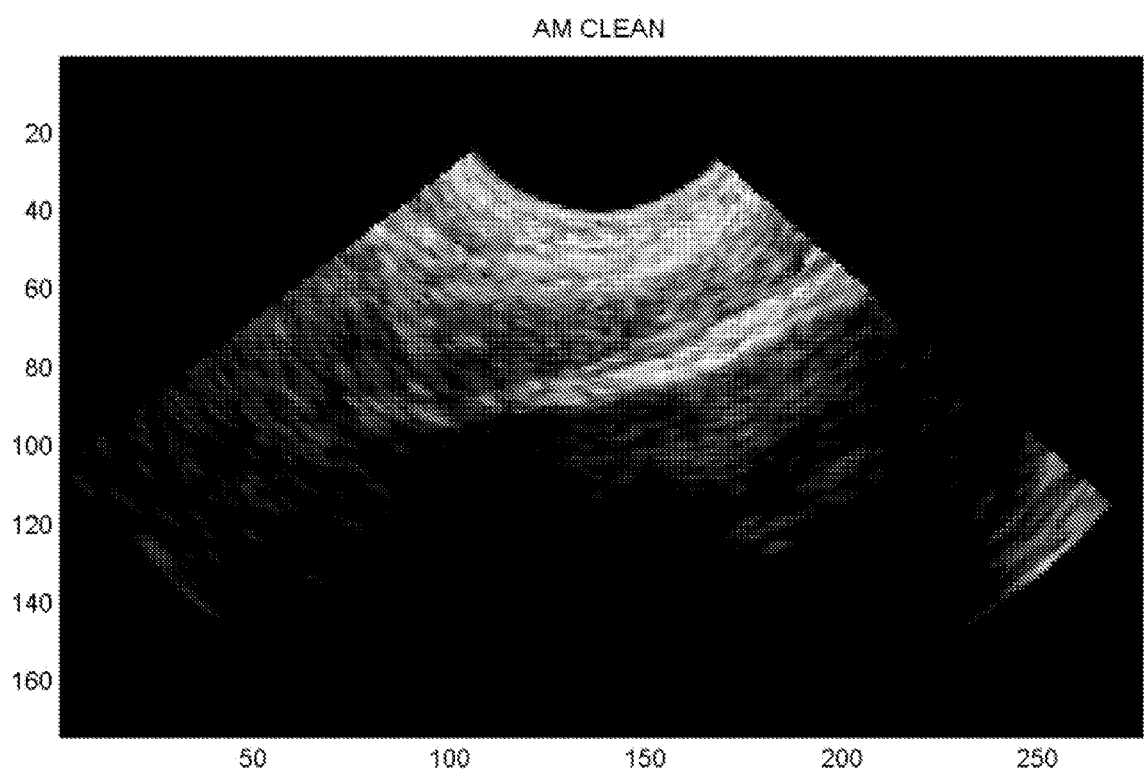

FIG. 20 is the resultant image of FIG. 18 that has undergone image processing via nonparametric estimation under sub-algorithm 400A. The low echogenic region is darker and the echogenic regions are brighter with more contrast than the magnified, unprocessed image of FIG. 19.

Figure 21:
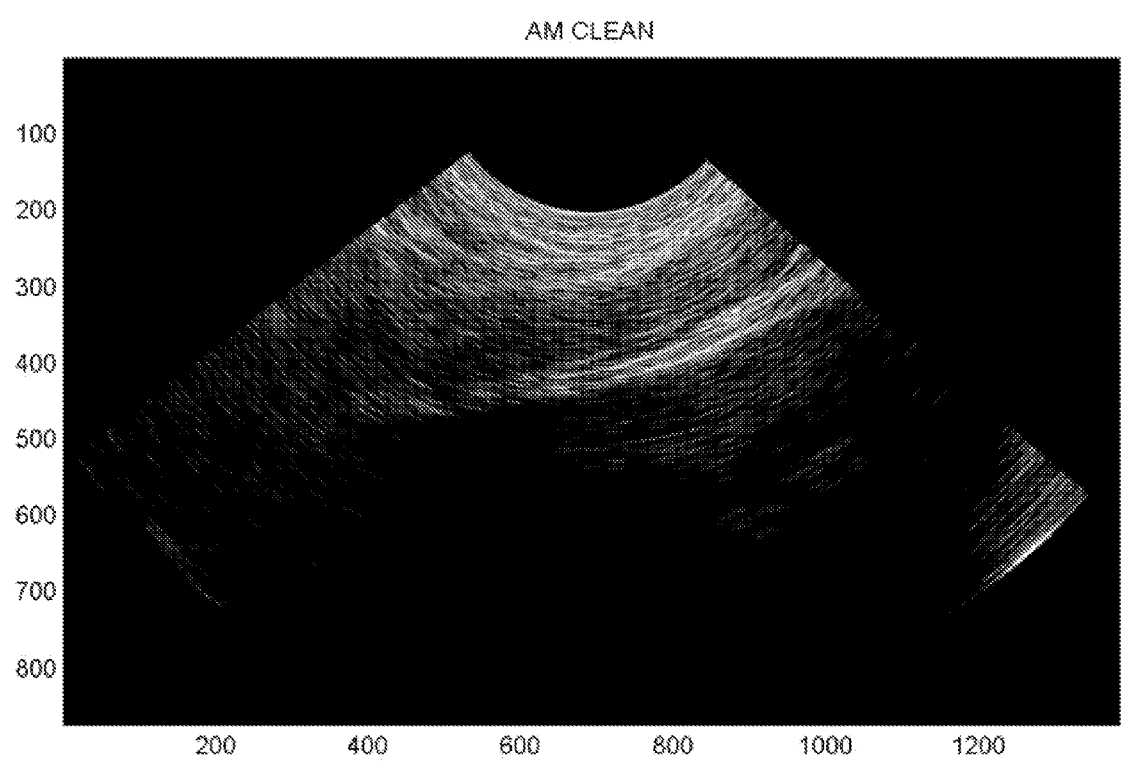

FIG. 21 is the resultant image of FIG. 18 that has undergone image processing via parametric estimation under sub-algorithm 400B. The low echogenic region is darker and the echogenic regions are brighter with enhanced contrast and clarity than the magnified, unprocessed image of FIG. 19.

Figure 22:
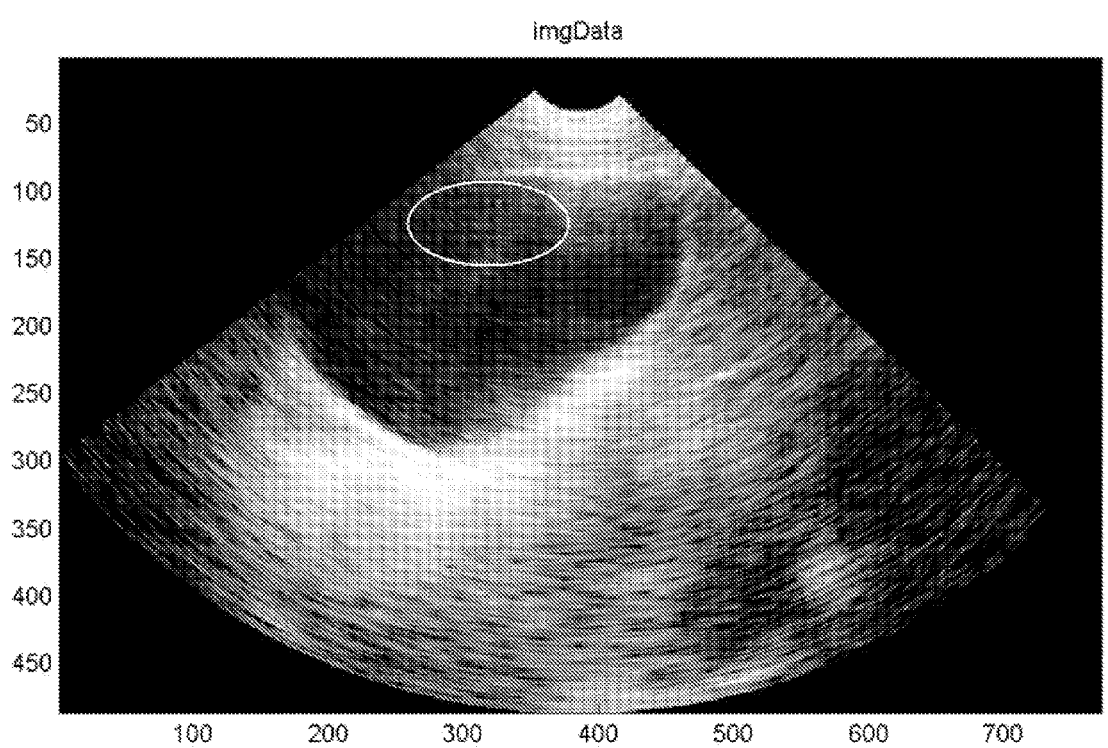

FIG. 22 is another unprocessed image that will undergo image enhancement processing.

Figure 23:
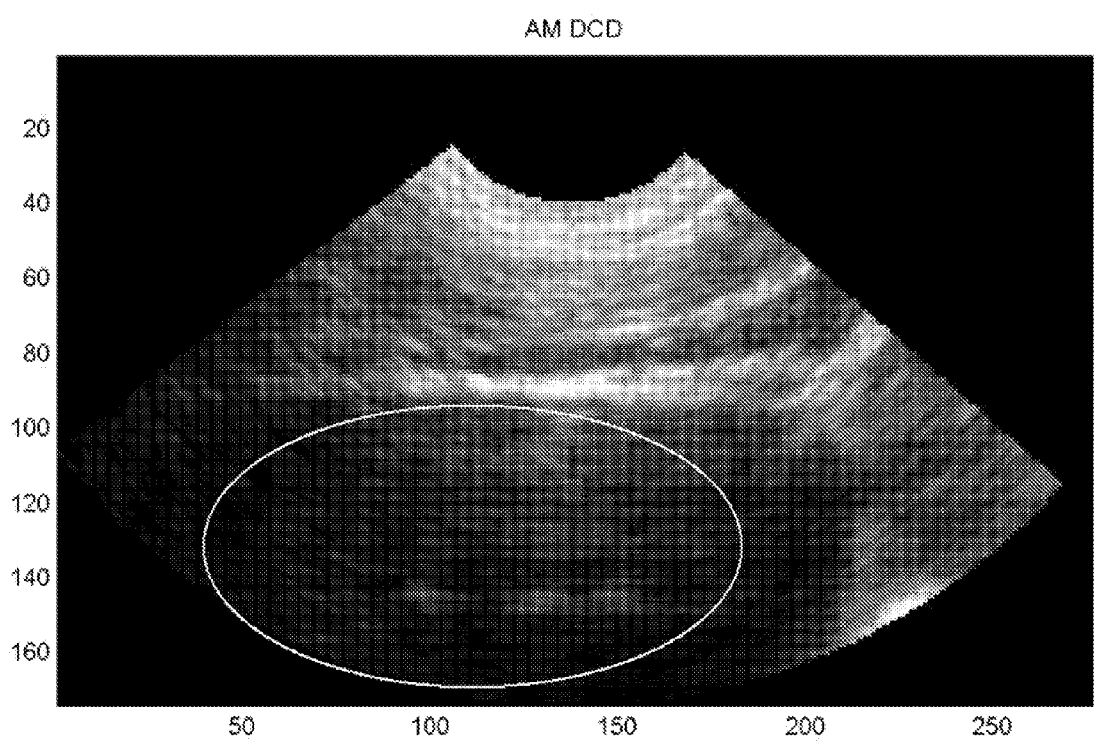

FIG. 23 illustrates an enclosed portion of a magnified region of FIG. 22.

Figure 24:
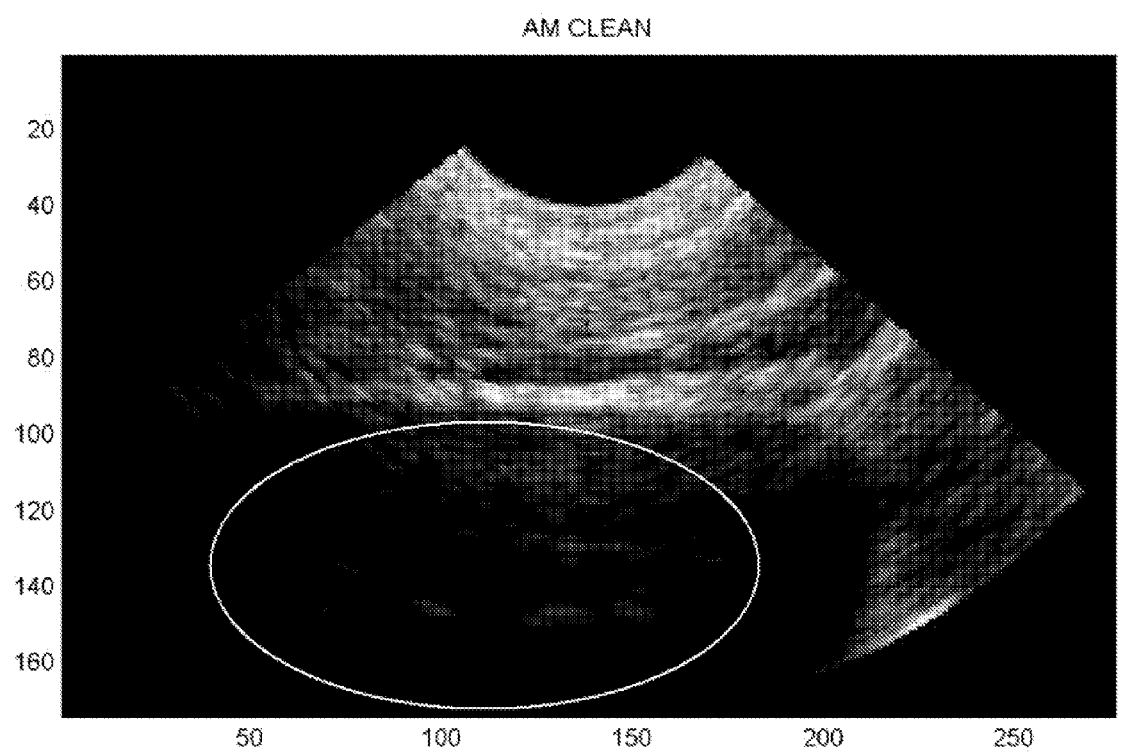

FIG. 24 is the resultant image of FIG. 22 that has undergone image processing via nonparametric estimation under sub-algorithm 400A. The low echogenic region is darker and the echogenic regions are brighter with more contrast than the magnified, unprocessed image of FIG. 23.

Figure 25:
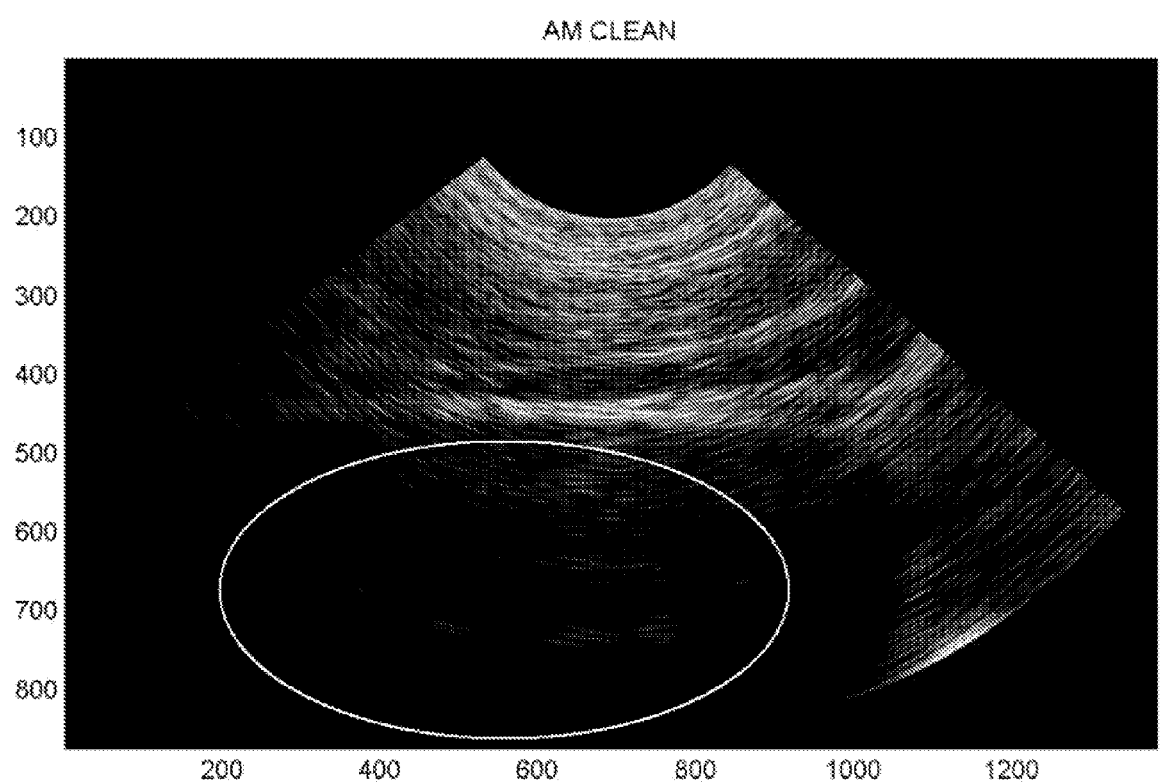

FIG. 25 is the resultant image of FIG. 22 that has undergone image processing via parametric estimation under sub-algorithm 400B. The low echogenic region is darker and the echogenic regions are brighter with enhanced contrast and clarity than the magnified, unprocessed image of FIG. 23.

FIG. 26 depicts a schematic example of a time velocity map derived from sub-algorithm 310.

FIG. 27 depicts another schematic example of a time velocity map derived from sub-algorithm 310.

Figure 28:
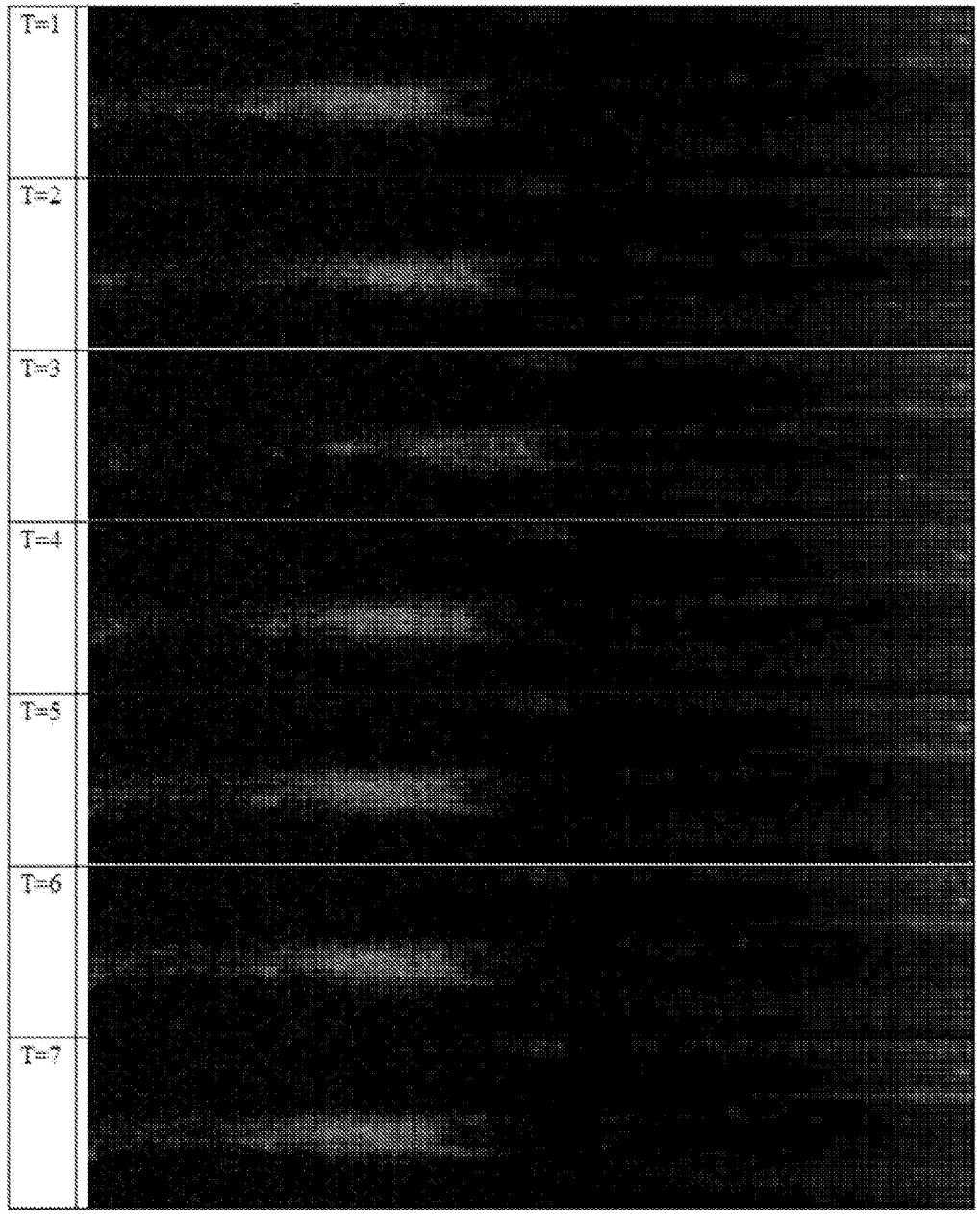
FIG. 28 illustrates a seven panel image series of a beating heart ventricle that will undergo the optical flow processes of sub-algorithm 300 in which at least two images are required.

FIG. 28 illustrates a seven panel image series of a beating heart ventricle that will undergo the optical flow processes of sub-algorithm 300 in which at least two images are required.

Figure 29:
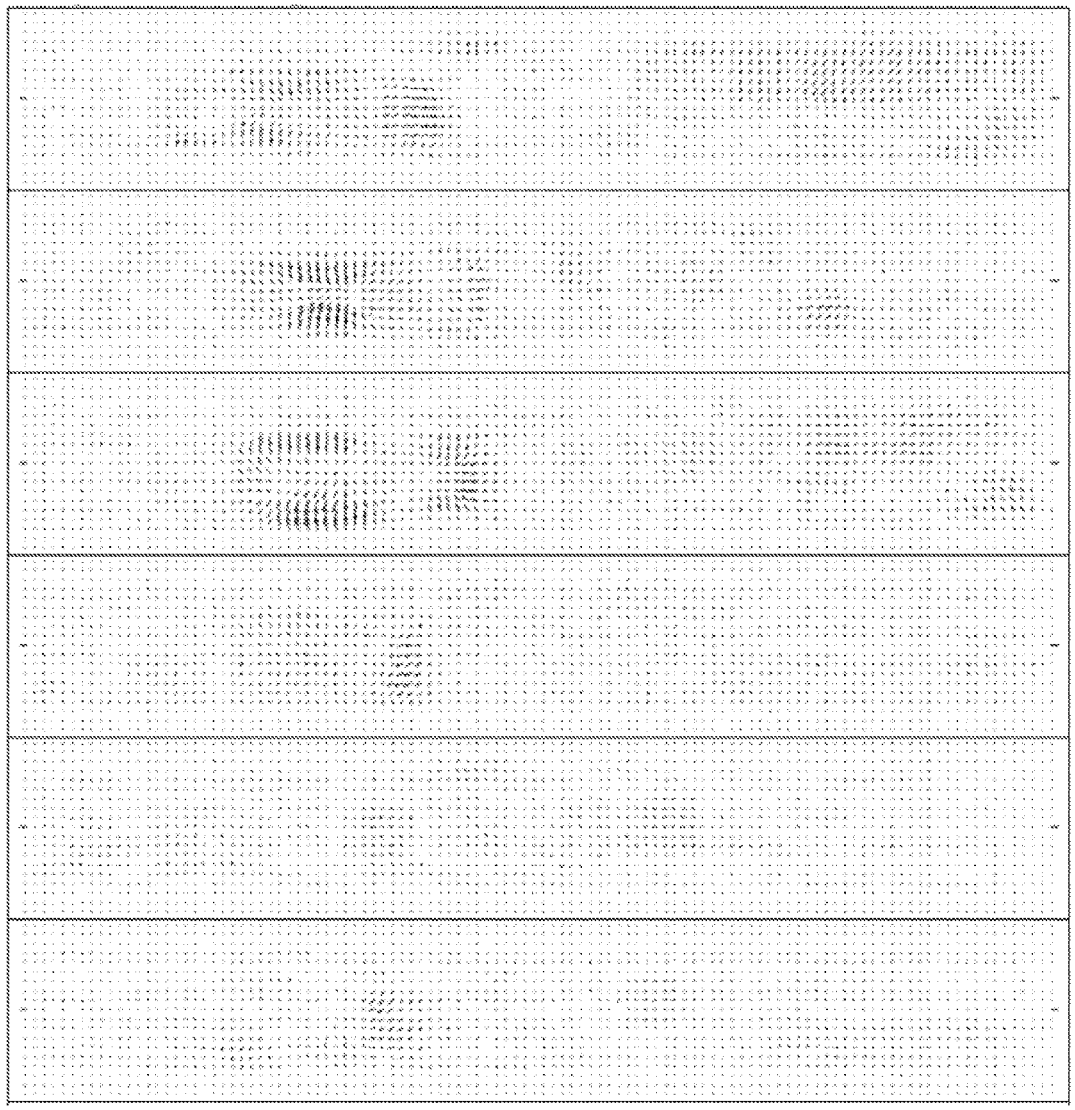
FIG. 29 illustrates an optical flow velocity map plot of the seven panel image series of FIG. 28 presented in a 2D flow pattern after undergoing sub-algorithm 310.

FIG. 29 illustrates an optical flow velocity map plot of the seven panel image series of FIG. 28 presented in a 2D flow pattern after undergoing sub-algorithm 310.

Figure 30:
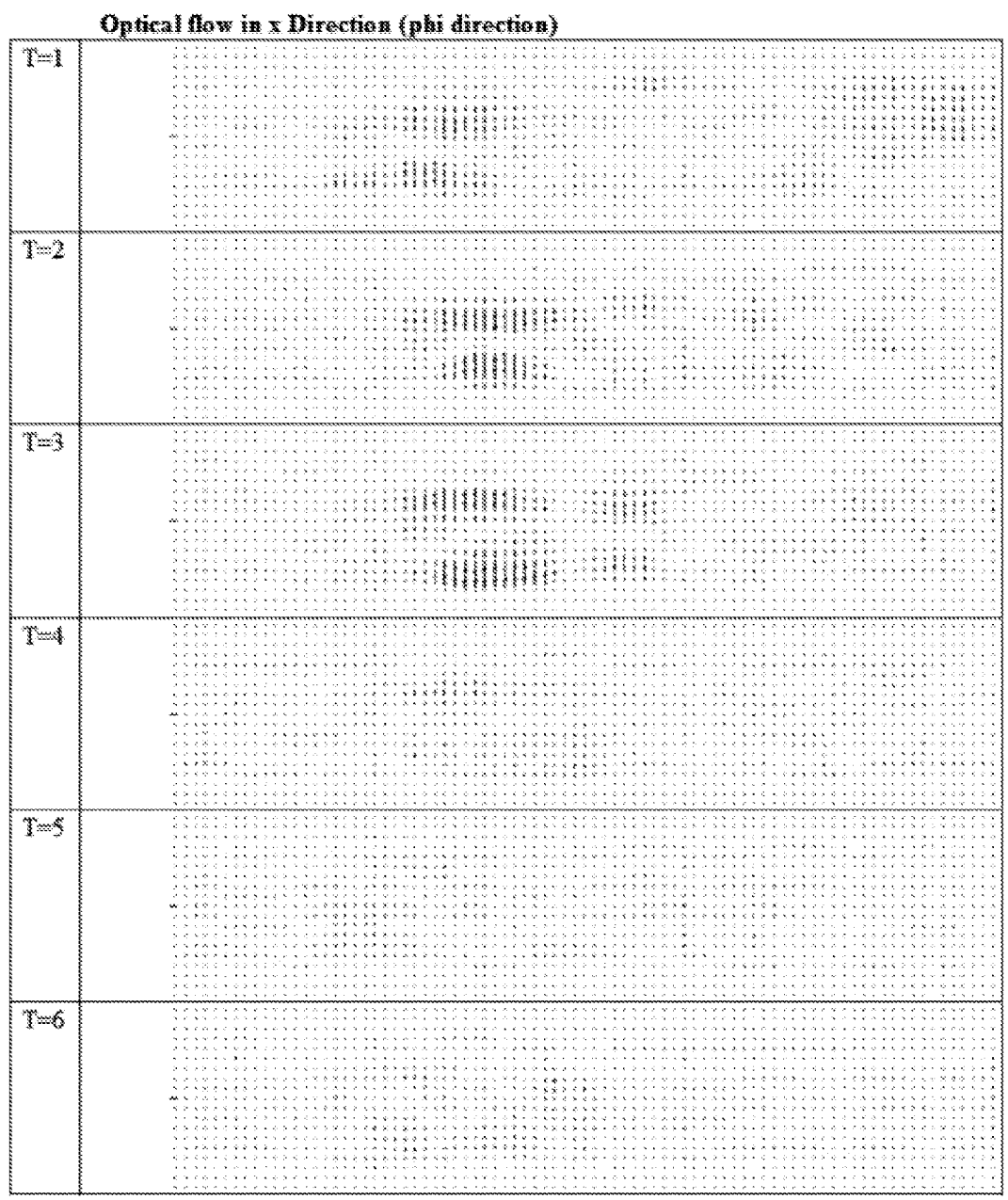
FIG. 30 illustrates an optical flow velocity map plot of the seven panel image series of FIG. 28 along the X-axis direction or phi direction after undergoing sub-algorithm 310.

FIG. 30 illustrates an optical flow velocity map plot of the seven panel image series of FIG. 28 along the X-axis direction or phi direction after undergoing sub-algorithm 310.

Figure 31:
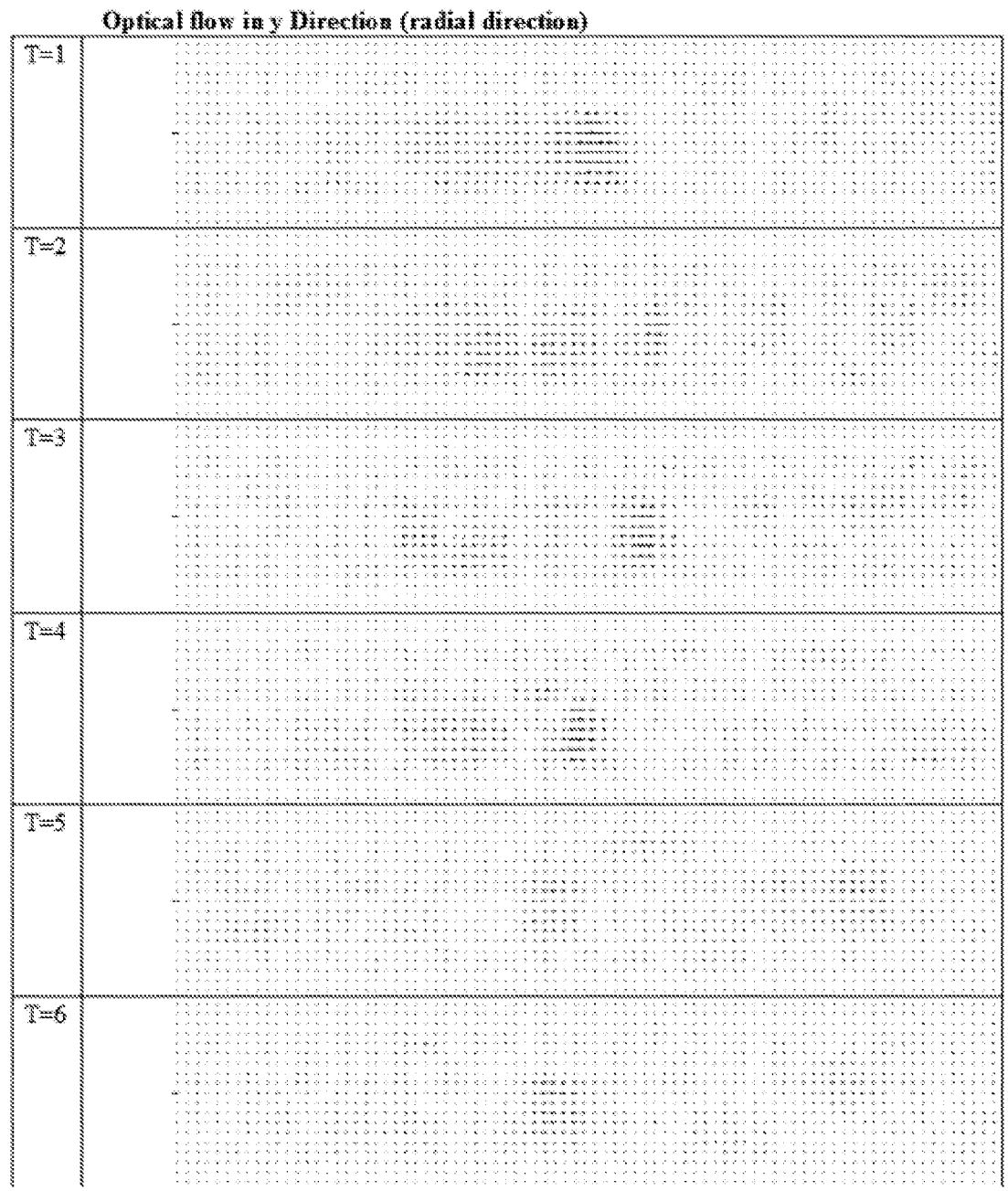
FIG. 31 illustrates an optical flow velocity map plot of the seven panel image series of FIG. 28 along the Y-axis direction radial direction after undergoing sub-algorithm 310.

FIG. 31 illustrates an optical flow velocity map plot of the seven panel image series of FIG. 28 along the Y-axis direction radial direction after undergoing sub-algorithm 310.

Figure 32:
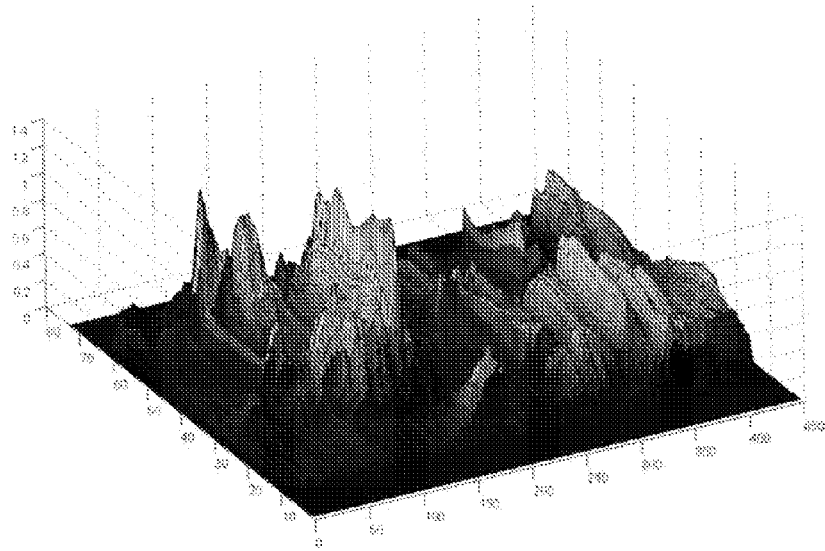
FIG. 32 illustrates a 3D optical vector plot after undergoing sub-algorithm 310 and corresponds to the top row of FIG. 29.

FIG. 32 illustrates a 3D optical vector plot after undergoing sub-algorithm 310 and corresponds to the top row of FIG. 29.

Figure 33:
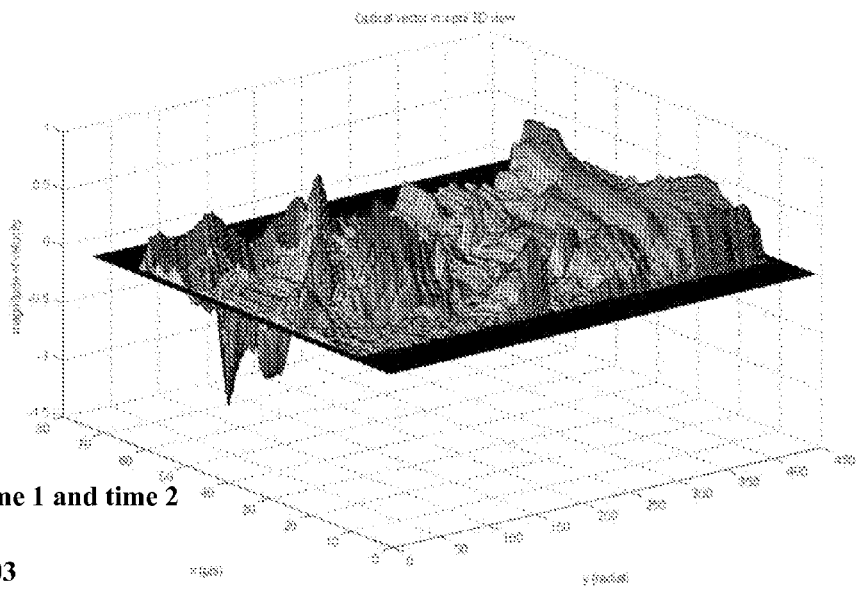
FIG. 33 illustrates a 3D optical vector plot in the phi direction after undergoing sub-algorithm 310 and corresponds to FIG. 30 at T=1.

FIG. 33 illustrates a 3D optical vector plot in the phi direction after undergoing sub-algorithm 310 and corresponds to FIG. 30 at threshold value T=1.

Figure 34:
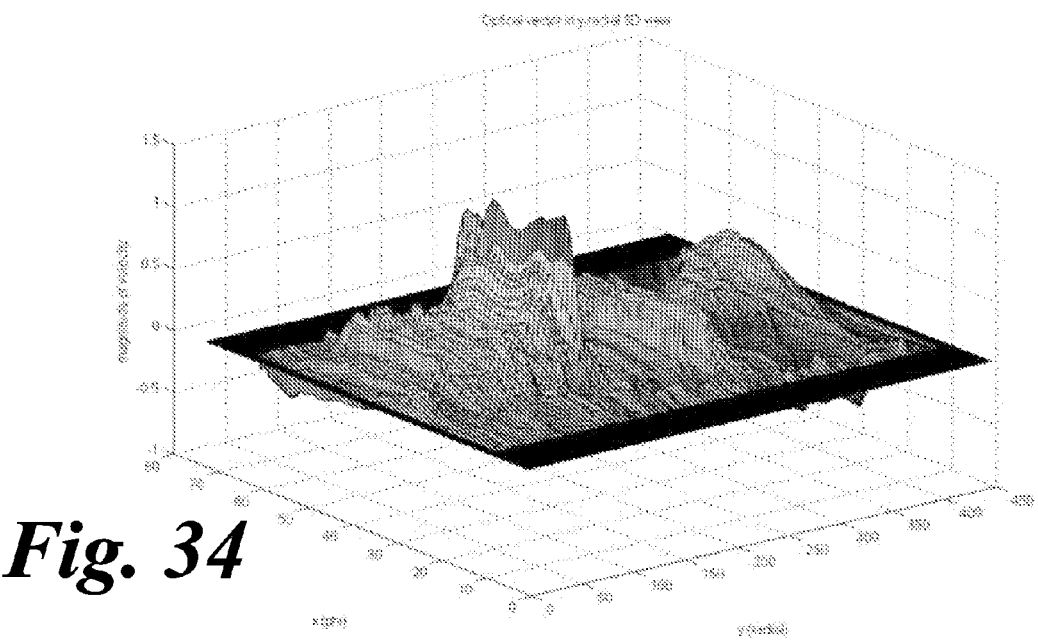
FIG. 34 illustrates a 3D optical vector plot in the radial direction after undergoing sub-algorithm 310 and corresponds to FIG. 31 at T=1.

FIG. 34 illustrates a 3D optical vector plot in the radial direction after undergoing sub-algorithm 310 and corresponds to FIG. 31 at T=1.

Figure 35:
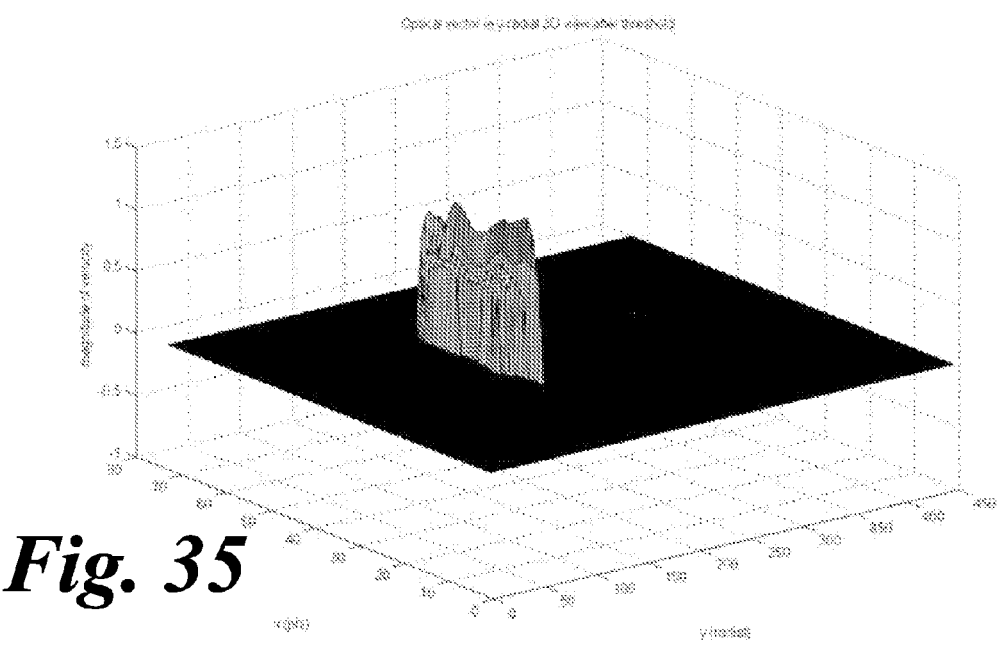
FIG. 35 illustrates a 3D optical vector plot in the radial direction above a Y-axis threshold setting of 0.6 after undergoing sub-algorithm 310 and corresponds to FIG. 34 the threshold T that are less than 0.6 are set to 0.

FIG. 35 illustrates a 3D optical vector plot in the radial direction above a Y-axis threshold setting of 0.6 after undergoing sub-algorithm 310 and corresponds to FIG. 34 the threshold T that are less than 0.6 are set to 0.

FIGS. 36A-G depicts embodiments of the sonic gel dispenser.

FIG. 36A illustrates the metered dispensing of sonic gel by calibrated rotation of a compressing wheel. The peristaltic mechanism using the compressing wheel is shown in partial a side view compressing wheel mechanism.

FIG. 36B illustrates in cross-section the inside the dispenser showing a collapsible bag that is engaged by the compressing wheel. As more rotation action is conveyed the compressing wheel, the bag progressively collapses.

FIG. 36C illustrates an alternative embodiment employing compression by hand gripping.

FIG. 36D illustrates an alternative embodiment employing push button or lever compression to dispense metered quantities of sonic gel.

FIG. 36E illustrates an alternative embodiment employing air valves to limit re-gassing of internal sonic gel volume stores within the sonic gel dispenser. The value is pinched closed while when the gripping or compressing wheel pressure is lessened and spring opens when the gripping or compressing wheel pressure is increased to allow sonic gel to be dispensed.

FIG. 36F illustrates a side, cross-sectional view of the gel dispensing system that includes a pre-packaged collapsible bottle with a refill bag, a bottle holder that positions the pre-packaged bottle for use, and a sealed tip that may be clipped open.

FIG. 36G illustrate a side view of the pre-packaged collapsible bottle of FIG. 36F. A particular embodiment includes eight ounce squeeze bottle.

FIGS. 37-46 concern insertion viewed by ultrasonic systems in which the optimization of cannula motion detection during insertion is enhanced with method algorithms directed to detect moving cannula fitted with echogenic ultrasound micro reflectors.

An embodiment related to cannula insertion generally includes an ultrasound probe attached to a first camera and a second camera and a processing and display generating system that is in signal communication with the ultrasound probe, the first camera, and/or the second camera. A user of the system scans tissue containing a target vein using the ultrasound probe and a cross-sectional image of the target vein is displayed. The first camera records a first image of a cannula in a first direction and the second camera records a second image of the cannula in a second direction orthogonal to the first direction. The first and/or the second images are processed by the processing and display generating system along with the relative positions of the ultrasound probe, the first camera, and/or the second camera to determine the trajectory of the cannula. A representation of the determined trajectory of the cannula is then displayed on the ultrasound image.

Figure 37:
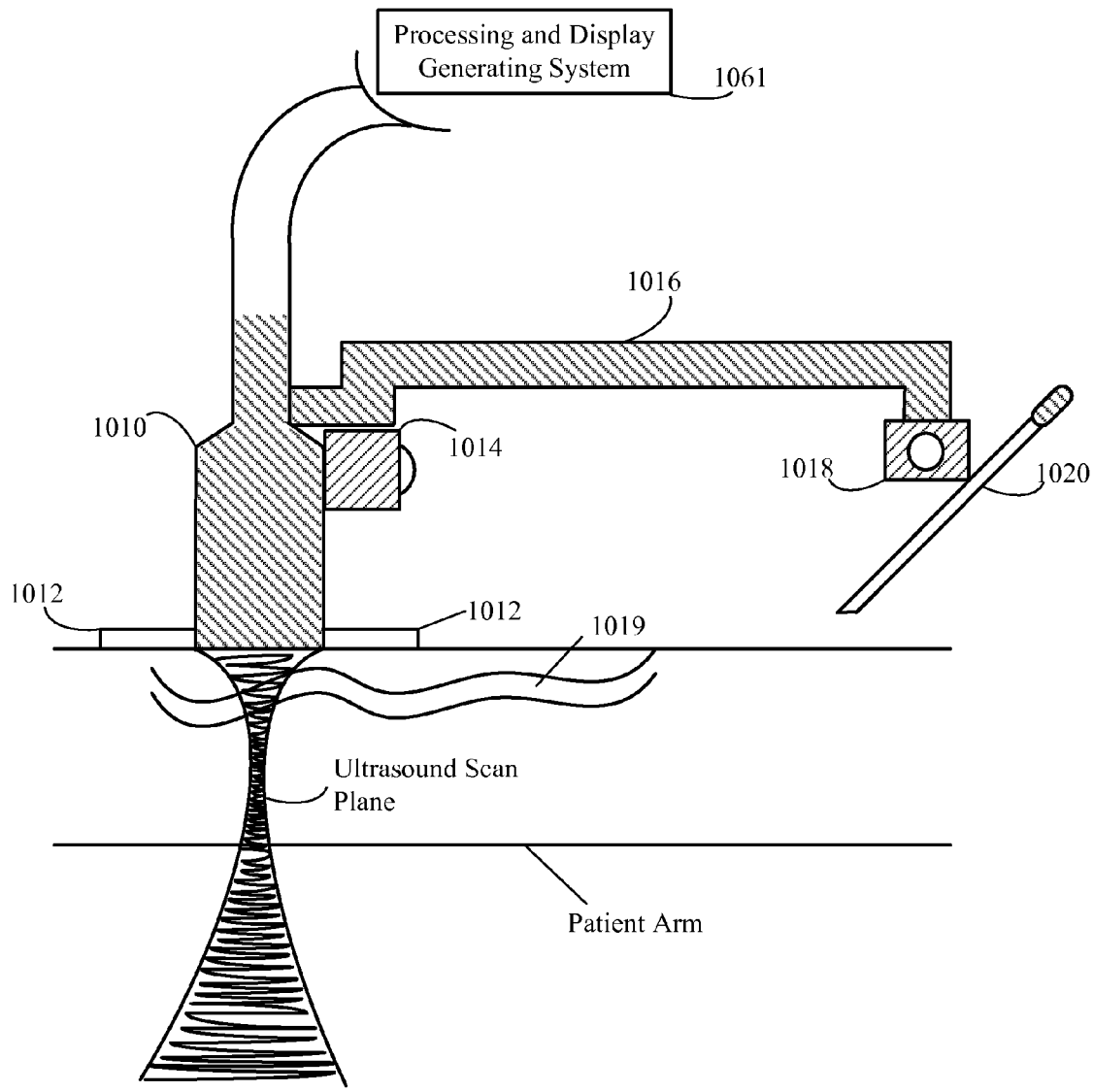
FIGS. 37 and 38 are diagrams showing one embodiment of the present invention.

FIG. 37 is a diagram illustrating a side view of one embodiment of the present invention. A two-dimensional (2D) ultrasound probe 1010 is attached to a first camera 1014 that takes images in a first direction. The ultrasound probe 1010 is also attached to a second camera 1018 via a member 1016. In other embodiments, the member 1016 may link the first camera 1014 to the second camera 1018 or the member 1016 may be absent, with the second camera 1018 being directly attached to a specially configured ultrasound probe. The second camera 1018 is oriented such that the second camera 1018 takes images in a second direction that is orthogonal to the first direction of the images taken by the first camera 1014. The placement of the cameras 1014, 1018 may be such that they can both take images of a cannula 1020 when the cannula 1020 is placed before the cameras 1014, 1018. A needle may also be used in place of a cannula. The cameras 1014, 1018 and the ultrasound probe 1010 are geometrically interlocked such that the cannula 1020 trajectory can be related to an ultrasound image. In FIG. 37, the second camera 1018 is behind the cannula 1020 when looking into the plane of the page. The cameras 1014, 1018 take images at a rapid frame rate of approximately 1030 frames per second. The ultrasound probe 1010 and/or the cameras 1014, 1018 are in signal communication with a processing and display generating system 1061.

First, a user employs the ultrasound probe 1010 and the processing and display generating system 1061 to generate a cross-sectional image of a patient's arm tissue containing a vein to be cannulated ("target vein") 1019. This could be done by one of the methods disclosed in the related patents and/or patent applications which are herein incorporated by reference, for example. The user then identifies the target vein 1019 in the image using methods such as simple compression which differentiates between arteries and/or veins by using the fact that veins collapse easily while arteries do not. After the user has identified the target vein 1019, the ultrasound probe 1010 is affixed to the patient's arm over the previously identified target vein 19 using a magnetic tape material 1012. The ultrasound probe 1010 and the processing and display generating system 1061 continue to generate a 2D cross-sectional image of the tissue containing the target vein 1019. Images from the cameras 1014, 1018 are provided to the processing and display generating system 1061 as the cannula 1020 is approaching and/or entering the arm of the patient.

The processing and display generating system 1061 locates the cannula 1020 in the images provided by the cameras 1014, 1018 and determines the projected location at which the cannula 1020 will penetrate the cross-sectional ultrasound image being displayed. The trajectory of the cannula 1020 is determined in some embodiments by using image processing to identify bright spots corresponding to micro reflectors previously machined into the shaft of the cannula 1020 or a needle used alone or in combination with the cannula 1020. Image processing uses the bright spots to determine the angles of the cannula 1020 relative to the cameras 1014, 1018 and then generates a projected trajectory by using the determined angles and/or the known positions of the cameras 1014, 1018 in relation to the ultrasound probe 10. In other embodiments, determination of the cannula 1020 trajectory is performed using edge-detection algorithms in combination with the known positions of the cameras 1014, 1018 in relation to the ultrasound probe 1010, for example.

The projected location may be indicated on the displayed image as a computer-generated cross-hair 1066, the intersection of which is where the cannula 1020 is projected to penetrate the image. When the cannula 1020 does penetrate the cross-sectional plane of the scan produced by the ultrasound probe 1010, the ultrasound image confirms that the cannula 1020 penetrated at the location of the cross-hair 1066. This gives the user a real-time ultrasound image of the target vein 1019 with an overlaid real-time computer-generated image of the position in the ultrasound image that the cannula 1020 will penetrate. This allows the user to adjust the location and/or angle of the cannula 1020 before and/or during insertion to increase the likelihood they will penetrate the target vein 1019. Risks of pneumothorax and other adverse outcomes should be substantially reduced since a user will be able to use normal "free" insertion procedures but have the added knowledge of knowing where the cannula 1020 trajectory will lead.

Figure 38:
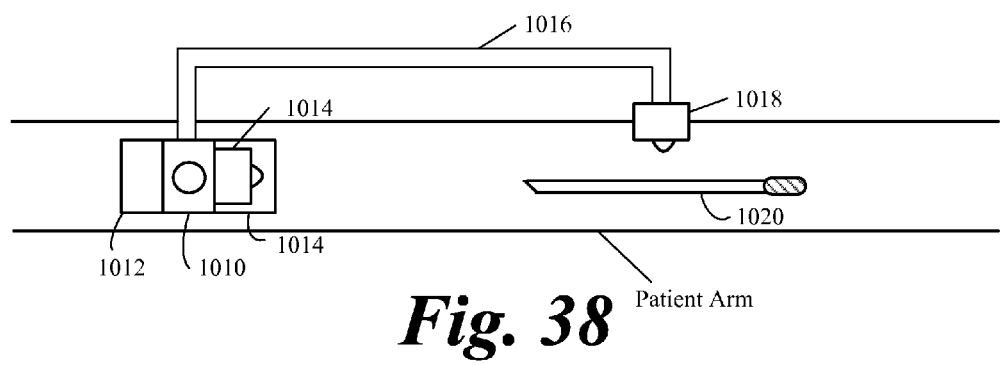

FIG. 38 is a diagram illustrating a top view of the embodiment shown in FIG. 37. It is more easily seen from this view that the second camera 1018 is positioned behind the cannula 1020. The positioning of the cameras 1014, 1018 relative to the cannula 1020 allows the cameras 1014, 1018 to capture images of the cannula 1020 from two different directions, thus making it easier to determine the trajectory of the cannula 1020.

Figure 39:
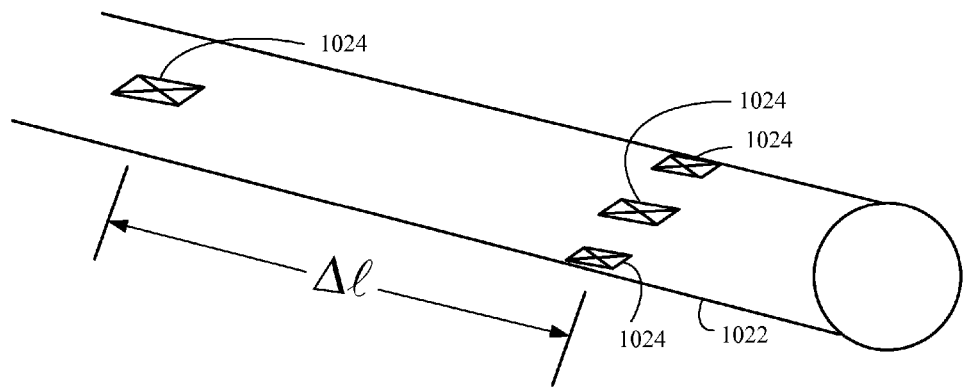
FIG. 39 is diagram showing additional detail for a needle shaft to be used with one embodiment of the invention.

FIG. 39 is diagram showing additional detail for a needle shaft 1022 to be used with one embodiment of the invention. The needle shaft 1022 includes a plurality of micro corner reflectors 1024. The micro corner reflectors 1024 are cut into the needle shaft 1022 at defined intervals Δl in symmetrical patterns about the circumference of the needle shaft 1022. The micro corner reflectors 1024 could be cut with a laser, for example.

Figure 40A:
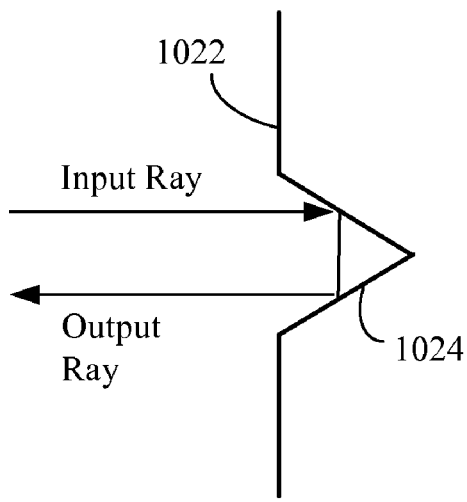
FIGS. 40A and 40B are diagrams showing close-up views of surface features of the needle shaft shown in FIG. 38.
Figure 40B:
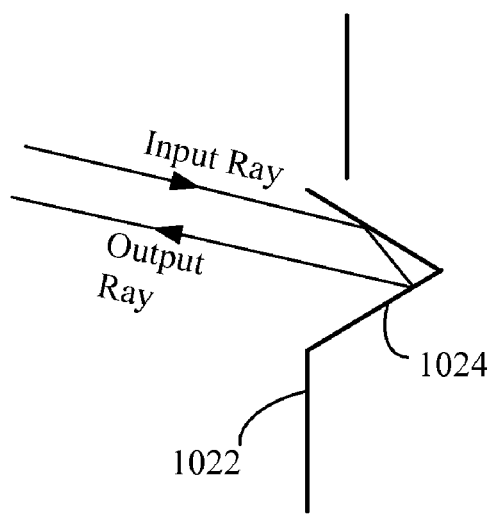

FIGS. 40A and 40B are diagrams showing close-up views of surface features of the needle shaft 1022 shown in FIG. 39. FIG. 40A shows a first input ray with a first incident angle of approximately 90° striking one of the micro corner reflectors 1024 on the needle shaft 1022. A first output ray is shown exiting the micro corner reflector 1024 in a direction toward the source of the first input ray. FIG. 40B shows a second input ray with a second incident angle other than 90° striking a micro corner reflector 1025 on the needle shaft 1022. A second output ray is shown exiting the micro corner reflector 1025 in a direction toward the source of the second input ray. FIGS. 40A and 40B illustrate that the micro corner reflectors 1024, 1025 are useful because they tend to reflect an output ray in the direction from which an input ray originated.

FIG. 41 is a diagram showing imaging components for use with the needle shaft 1022 shown in FIG. 39 in accordance with one embodiment of the invention. The imaging components are shown to include a first light source 1026, a second light source 1028, a lens 1030, and a sensor chip 1032. The first and/or second light sources 1026, 1028 may be light emitting diodes (LEDs), for example. In an example embodiment, the light sources 1026, 1028 are infra-red LEDs. Use of an infra-red source is advantageous because it is not visible to the human eye, but when an image of the needle shaft 1022 is recorded, the image will show strong bright dots where the micro corner reflectors 1024 are located because silicon sensor chips are sensitive to infra-red light and the micro corner reflectors 1024 tend to reflect output rays in the direction from which input rays originate, as discussed with reference to FIGS. 40A and 40B. In alternative embodiments, a single light source may be used. Although not shown, the sensor chip 1032 is encased in a housing behind the lens 1030 and the sensor chip 1032 and light sources 1026, 1028 are in electrical communication with the processing and display generating system 1061. The sensor chip 1032 and/or the lens 1030 form a part of the first and second cameras 1014, 1018 in some embodiments. In an example embodiment, the light sources 1026, 1028 are pulsed on at the time the sensor chip 1032 captures an image. In other embodiments, the light sources 1026, 1028 are left on during video image capture.

Figure 42:
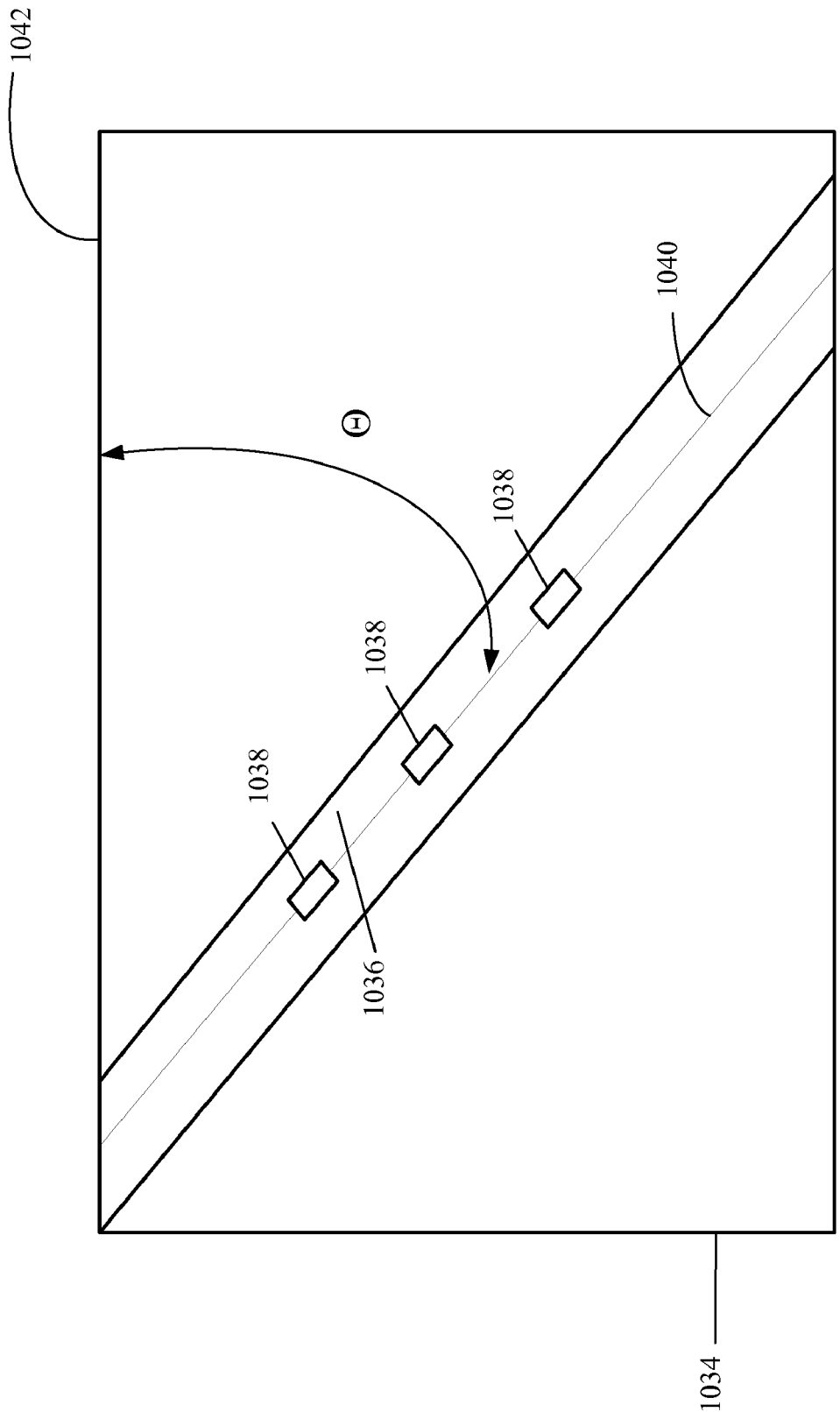
FIG. 42 is a diagram showing a representation of an image produced by the imaging components shown in FIG. 41.

FIG. 42 is a diagram showing a representation of an image 1034 produced by the imaging components shown in FIG. 41. The image 34 may include a needle shaft image 1036 that corresponds to a portion of the needle shaft 1022 shown in FIG. 41. The image 1034 also may include a series of bright dots 1038 running along the center of the needle shaft image 1036 that correspond to the micro corner reflectors 1024 shown in FIG. 41. A center line 1040 is shown in FIG. 42 to illustrate how an angle theta (θ) could be obtained by image processing to recognize the bright dots 1038 and determine a line through them. The angle theta represents the degree to which the needle shaft 1022 is inclined with respect to a reference line 1042 that is related to the fixed position of the sensor chip 1032.

Figure 43:
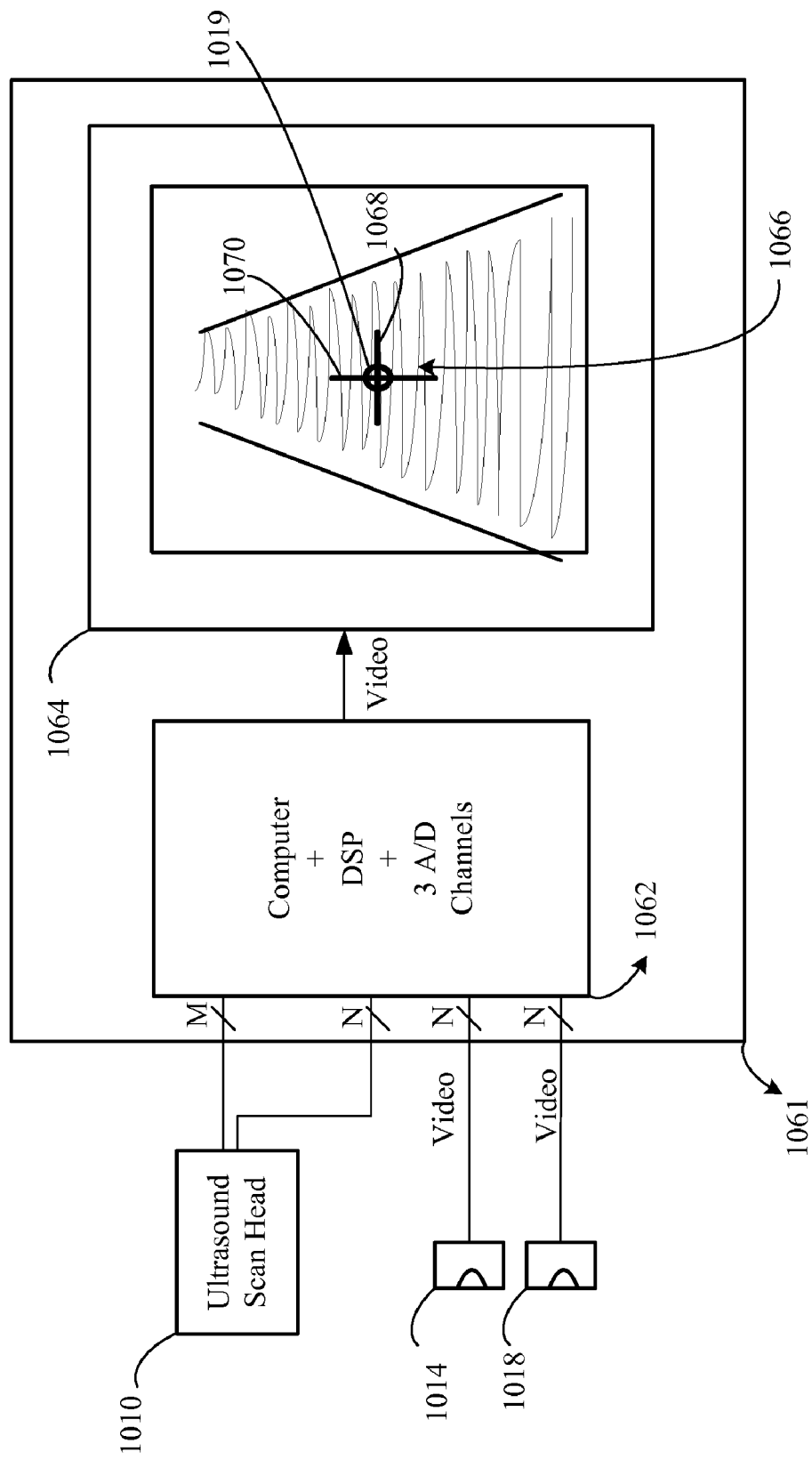
FIG. 43 is a system diagram of an embodiment of the present invention.

FIG. 43 is a system diagram of an embodiment of the present invention and shows additional detail for the processing and display generating system 1061 in accordance with an example embodiment of the invention. The ultrasound probe 1010 is shown connected to the processing and display generating system via M control lines and N data lines. The M and N variables are for convenience and appear simply to indicate that the connections may be composed of one or more transmission paths. The control lines allow the processing and display generating system 61 to direct the ultrasound probe 1010 to properly perform an ultrasound scan and the data lines allow responses from the ultrasound scan to be transmitted to the processing and display generating system 1061. The first and second cameras 1014, 1018 are also each shown to be connected to the processing and display generating system 1061 via N lines. Although the same variable N is used, it is simply indicating that one or more lines may be present, not that each device with a label of N lines has the same number of lines.

The processing and display generating system 1061 is composed of a display 1064 and a block 1062 containing a computer, a digital signal processor (DSP), and analog to digital (A/D) converters. As discussed for FIG. 37, the display 1064 will display a cross-sectional ultrasound image. The computer-generated cross hair 66 is shown over a representation of a cross-sectional view of the target vein 1019 in FIG. 43. The cross hair 1066 consists of an x-crosshair 1068 and a z-crosshair 1070. The DSP and the computer in the block 1062 use images from the first camera 1014 to determine the plane in which the cannula 1020 will penetrate the ultrasound image and then write the z-crosshair 1070 on the ultrasound image provided to the display 1064. Similarly, the DSP and the computer in the block 1062 use images from the second camera 1018, which are orthogonal to the images provided by the first camera 1014 as discussed for FIG. 37, to write the x-crosshair 1068 on the ultrasound image.

Figure 44:
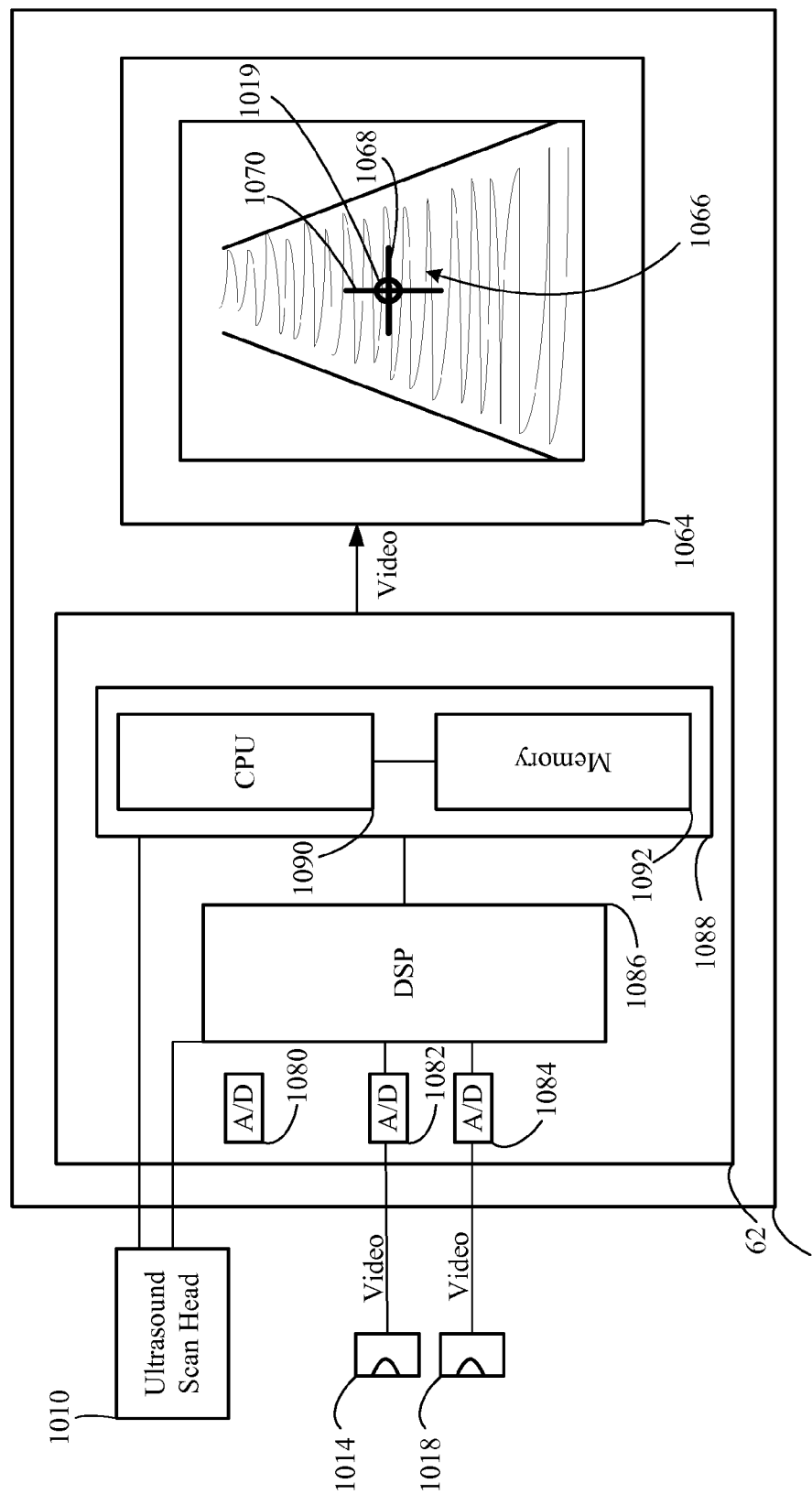
FIG. 44 is a system diagram of an example embodiment showing additional detail for one of the components shown in FIG. 38.

FIG. 44 is a system diagram of an example embodiment showing additional detail for the block 1062 shown in FIG. 39. The block 1062 includes a first A/D converter 1080, a second A/D converter 1082, and a third A/D converter 1084. The first A/D converter 1080 receives signals from the ultrasound probe 1010 and converts them to digital information that is provided to a DSP 1086. The second and third A/D converters 1082, 1084 receive signals from the first and second cameras 1014, 1018 respectively and convert the signals to digital information that is provided to the DSP 1086. In alternative embodiments, some or all of the A/D converters are not present. For example, video from the cameras 1014, 1018 may be provided to the DSP 1086 directly in digital form rather than being created in analog form before passing through A/D converters 1082, 1084. The DSP 1086 is in data communication with a computer 1088 that includes a central processing unit (CPU) 1090 in data communication with a memory component 1092. The computer 1088 is in signal communication with the ultrasound probe 1010 and is able to control the ultrasound probe 1010 using this connection. The computer 1088 is also connected to the display 64 and produces a video signal used to drive the display 1064.

Figure 45:
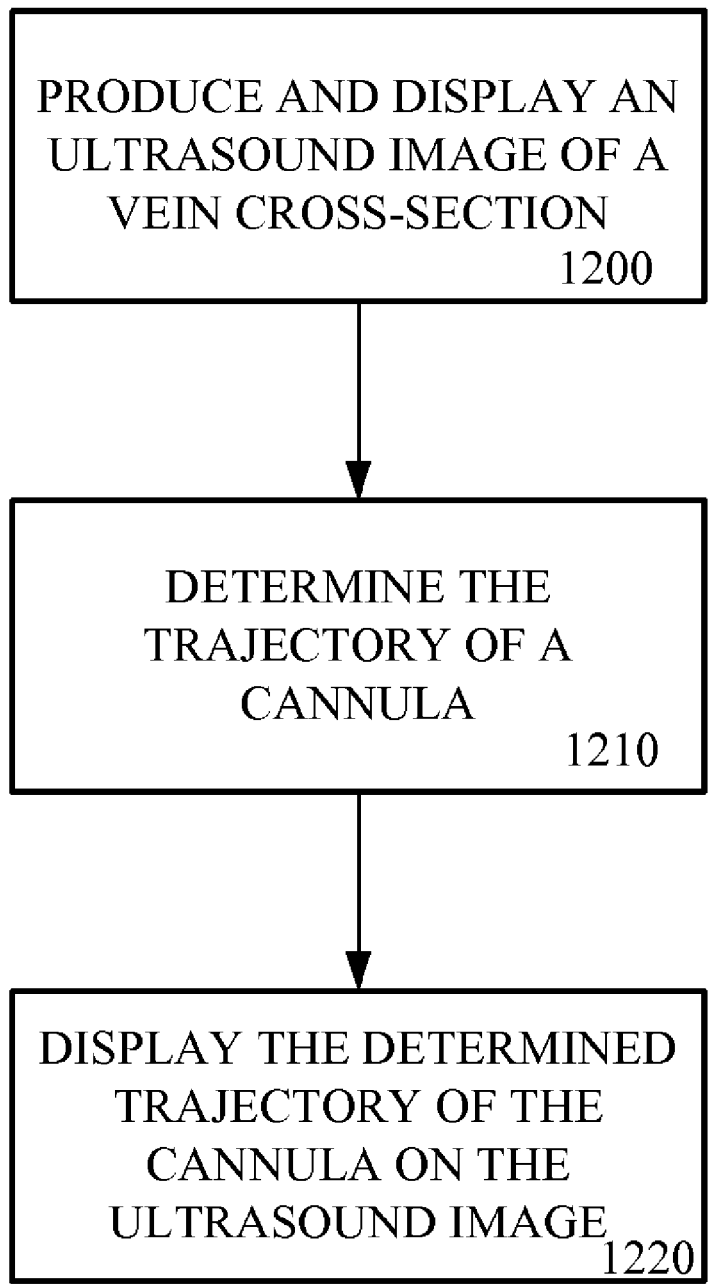
FIGS. 45 and 46 are flowcharts of a method of displaying the trajectory of a cannula in accordance with an embodiment of the present invention.

FIG. 45 is a flowchart of a method of displaying the trajectory of a cannula in accordance with an embodiment of the present invention. First, at a block 1200, an ultrasound image of a vein cross-section is produced and/or displayed. Next, at a block 1210, the trajectory of a cannula is determined. Then, at a block 1220, the determined trajectory of the cannula is displayed on the ultrasound image.

Figure 46:
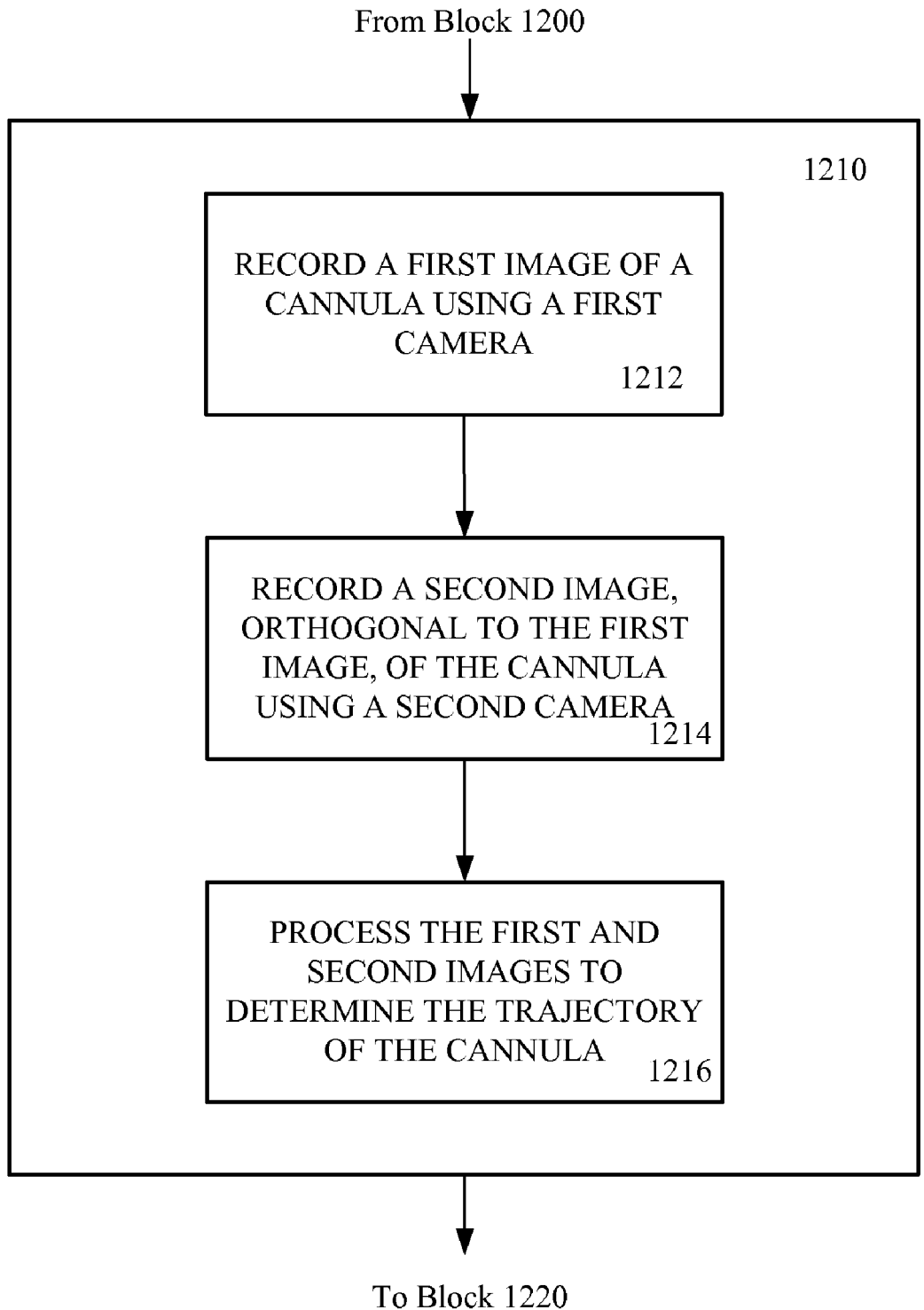

FIG. 46 is a flowchart showing additional detail for the block 1210 depicted in FIG. 45. The block 1210 includes a block 1212 where a first image of a cannula is recorded using a first camera. Next, at a block 1214, a second image of the cannula orthogonal to the first image of the cannula is recorded using a second camera. Then, at a block 1216, the first and second images are processed to determine the trajectory of the cannula.

While the preferred embodiment of the invention has been illustrated and described, as noted above, many changes can be made without departing from the spirit and scope of the invention. For example, a three dimensional ultrasound system could be used rather than a 2D system. In addition, different numbers of cameras could be used along with image processing that determines the cannula 1020 trajectory based on the number of cameras used. The two cameras 1014, 1018 could also be placed in a non-orthogonal relationship so long as the image processing was adjusted to properly determine the orientation and/or projected trajectory of the cannula 1020. Also, an embodiment of the invention could be used for needles and/or other devices which are to be inserted in the body of a patient. Additionally, an embodiment of the invention could be used in places other than arm veins. Regions of the patient's body other than an arm could be used and/or biological structures other than veins may be the focus of interest. As regards ultrasound-based algorithms, alternate embodiments may be configured to image acquisitions other than ultrasound, for example X-ray, visible and infrared light acquired images. Accordingly, the scope of the invention is not limited by the disclosure of the preferred embodiment.

The embodiments of the invention in which an exclusive property or privilege is claimed are defined as follows:

1. A system to improve image clarity in ultrasound images comprising:
   an ultrasound transducer connected with a microprocessor configured to collect and process signals of at least one of a fundamental and harmonic ultrasound echoes returning from at least two ultrasound-based images from a scanned region-of-interest based upon a change in pixel movement revealed by information contained in optical flow velocity maps pertaining to the scanned region-of-interest between the at least two ultrasound images, and
   a computer executable point spread function algorithm having instructions configured to suppress motion induced reverberations attributable to the change in pixel movement,
   wherein motion sections are compensated with the stationary sections within the scanned region of interest.

2. A method to improve image clarity in ultrasound images comprising:
   acquiring at least two ultrasound images from a region of interest of a subject derived from at least one of a fundamental and harmonic ultrasound echoes;
   segmenting the region of interest;
   determining the motion and still sections of the region of interest; and
   compensating for the motion section within the region of interest based upon applying a point spread function algorithm having computer executable instructions to suppress induced reverberations attributable to a change in pixel movement revealed by information contained in optical flow velocity maps pertaining to the region-of-interest between the at least two ultrasound images.

* * * * *